(12) United States Patent
Makielski et al.

(10) Patent No.: US 7,485,455 B2
(45) Date of Patent: Feb. 3, 2009

(54) NUCLEIC ACID ENCODING SODIUM CHANNEL SUBUNIT

(75) Inventors: Jonathan C. Makielski, Fitchburg, WI (US); Bin Ye, Madison, WI (US); Michael J. Ackerman, Rochester, MN (US)

(73) Assignees: Wisconsin Alumni Research Foundation, Madison, WI (US); Mayo Clinic Health Solutions, Rochester, MN (US)

( * ) Notice: Subject to any disclaimer, the term of this patent is extended or adjusted under 35 U.S.C. 154(b) by 546 days.

(21) Appl. No.: 10/632,342

(22) Filed: Aug. 1, 2003

(65) Prior Publication Data

US 2004/0126787 A1   Jul. 1, 2004

Related U.S. Application Data

(60) Provisional application No. 60/401,018, filed on Aug. 2, 2002.

(51) Int. Cl.
*C12N 15/12* (2006.01)
*C12N 5/10* (2006.01)
*C12N 15/63* (2006.01)

(52) U.S. Cl. .................. 435/320.1; 435/325; 536/23.1; 536/23.5; 536/24.1

(58) Field of Classification Search .................. None
See application file for complete search history.

(56) References Cited

U.S. PATENT DOCUMENTS

| | | |
|---|---|---|
| 5,380,836 A | 1/1995 | Rogart |
| 5,599,673 A | 2/1997 | Keating et al. |
| 5,892,018 A | 4/1999 | Welsh et al. |
| 6,030,810 A | 2/2000 | Delgado et al. |
| 6,991,910 B2 * | 1/2006 | Adorante et al. ............. 435/7.2 |

FOREIGN PATENT DOCUMENTS

WO   WO 96/28537   9/1996

OTHER PUBLICATIONS

Baroudi, et al., "Novel Mechanism for Brugada Syndome: Defective Surface Localization of an SCN5A mutant (R1432G)," Circ. Res. 2001; 88; 78-83.
Hartmann, et al., "Effects of III-IV Linker Mutations on Human Heart Na+ channel inactivation gating," Circ. Res. 1994; 75; 114-122.
Ye, et al., "Third Complete Sequence of Human Cardiac Sodium Channel α Subunit hH1b Reveals Polymorphism in Domain I and II," Biophys. J. Mtg. Abst. (2001).
Gellens, et al., "Primary structure and functional expression of hte human cardiac tetrodotxin-insensitive voltage-dependent sodium channel," Proc. Natl. Acad. Sci USA 89;554-558, Jan. 1992.
GenBank Accession No. AY038064 (available starting Aug. 1, 2001).
Chen Q, et al., "Genetic basis and molecular mechanism for idiopathic ventricular fibrillation," Nature 392:293-296 (1998).
Deschênes I, et al., "Electrophysiological characterization of SCN5A mutations causing long QT (E1784K) and Brugada (R1512W and R1432G) syndromes," Cardiovasc. Res. 46:55-65 (2000).

* cited by examiner

*Primary Examiner*—Michael Pak
(74) *Attorney, Agent, or Firm*—Quarles & Brady LLP

(57) ABSTRACT

The present invention discloses four groups of SCN5A variants that represent the most common SCN5A variants in humans. A specific mutation in one of the variants has been shown to display a different phenotype in relation to a human heart disease than other variants and known human sodium channel α subunits with corresponding mutations. The present invention provides new tools to study mutations and to design or identify new diagnostic and treatment strategies or agents for sodium channel related diseases or conditions.

6 Claims, 6 Drawing Sheets

NUCLEIC ACID ENCODING SODIUM CHANNEL SUBUNIT

CROSS-REFERENCE TO RELATED APPLICATIONS

This application claims priority to U.S. provisional application Ser. No. 60/401,018, filed on Aug. 2, 2002, which is incorporated by reference in its entirety.

STATEMENT REGARDING FEDERALLY SPONSORED RESEARCH OR DEVELOPMENT

This invention was made with United States government support awarded by the following agency: NIH, Grant No. HL56441. The United States government has certain rights in this invention.

BACKGROUND OF THE INVENTION

Sodium channel proteins embedded in cellular membranes of muscle cells, neurons and other excitable cells help produce and propagate electrical impulses and are implicated in many human diseases and conditions. Sodium channels are often composed of a pore-forming α subunit, having four homologous domains DI-DIV and six transmembrane regions S1-S6 per domain, and at least three auxiliary subunits β1, β2 and β3. The α subunit is sufficient to form a functional channel for generating sodium current flow across cellular membranes. An extensive review of cardiac ion channels published in Annual Review of Physiology 64:431-75 (2002) is incorporated by reference in its entirety as if set forth herein.

Human cardiac sodium channels play a critical role in cardiac excitation. hNa$_v$1.5, a human cardiac sodium channel α subunit encoded by the SCN5A gene forms a functioning monomeric sodium channel that carries the inward Na current ($I_{Na}$) in the heart. The $I_{Na}$ current is vital for excitation and conduction in working myocardium and in specialized conduction tissue such as Purkinje fibers.

Three distinct full-length polymorphic SCN5A clones that encode the hNav1.5 human cardiac sodium channel (designated SCN5A hH1, SCN5A hH1a, and SCN5A hH1b (or simply hH1, hH1a, and hH1b, respectively) have been isolated from human cardiac cDNA libraries (Gellens, M. E. et al., "primary structure and functional expression of the human cardiac tetrodotoxin-insensitive voltage-dependent sodium channel," *Proc. Natl. Acad. Sci. U.S.A.* 89, 554-558 (1992); Hartmann, H. A. et al., Effects of III-IV linker mutations on human heart Na$^+$ channel inactivation gating. *Circ. Res.* 75, 114-122 (1994), Ye, B. and J. Makielski, Third Complete Sequence of Human Cardiac Sodium Channel α Subunit Reveals Polymorphism in Domain I and II, Biophys. J. 80(1):225c (2001), each incorporated by reference herein as if set forth in its entirety.).

Subsequent to the publication of the hH1b sequence by Ye and Makielski, the authors determined errors in the published SCN5A hH1 protein sequence. The true polymorphisms among hH1, hH1a and hH1b are reflected in Table 1, infra. The amino acid numbering follows that of the original hH1 clone which contains 2016 amino acids. All of the differences are confined to the cytoplasmic linkers between DI-II and between DII-III. Briefly, hH1 and hH1a differ by just 3 amino acids—T559 vs. A559, Q1027 vs. R1027, and Q1077 vs. Q1077del (hH1 vs. hH1a, respectively)—over a total length of 2016/2015 amino acids, respectively. The hH1b protein also differs from either hH1 or hH1a at positions 559, 1027 and 1077, as well as at positions 558 and 618. The arginine at position 558 in hH1b is consistent with a previously characterized histidine-to-arginine polymorphism (Iwasa, et al., "Twenty single nucleotide polymorphisms (SNPs) and their allelic frequencies in four genes that are responsible for familial long QT syndrome in the Japanese population," *J. Hum. Genet.* 45, 182-183). The isoleucine at position 618 is consistent with a known high-frequency spontaneous conservative leucine-to-isoleucine substitution.

The significance of polymorphisms in the sodium channel is still unknown. For example, it is not known how such polymorphisms affect the mutation phenotype of SCN5A. Nonetheless, identified polymorphisms can help identify disease-associated mutations in SCN5A. For example, various SCN5A mutations are associated with congenital Long QT syndrome, idiopathic ventricular fibrillation and the Brugada syndrome (Keating and Sanguinetti 2001).

In separate studies, the two known polymorphic forms showed only minor kinetic differences that can be attributed to different expression systems and study techniques including solutions, temperature, and protocols. (Gellens, M. E. et al., supra; Hartmann et. al., supra; and Wattanasirichaigoon et. al. 1999). Subtle differences in kinetics such as decay rates, inactivation midpoints, and late $I_{Na}$, however, may be important in controlling repolarization.

Sodium channel α subunits encoded by an SCN5A hH1a clone carrying an arrhythmogenic missense methionine-to-leucine mutation at amino acid 1766 (M1766L) further exhibit a significant inward sodium current level drop, relative to the current level in channels encoded by a wild type hH1a clone. Recently, M1766L in the hH1a background was shown to have a trafficking defect and to cause QT prolongation and ventricular arrhythmia. These conditions can be rescued by low temperature, antiarrhythmic drugs and the β1 subunit. Valdivia et. al., C. R. et al., A Novel SCN5A Arrhythmia Mutation M1766L with Expression Defect Rescued by Mexiletine," *Cardiovasc. Res.* 54(3):624-9 (2002).

In another aspect, drugs that can alter sodium channel activities can relieve or prevent symptoms of certain conditions such as cardiac arrhythmias. Cardiac arrhythmias are abnormalities in the rate, regularity, or site of origin of the cardiac impulse, or a disturbance in conduction of the impulse that alters the normal sequence of atrial or ventricular activation. One known way to treat cardiac arrhythmias is to block the activity of a cardiac sodium channel. Sodium channel blockers used to treat cardiac arrhythmias include: Quinidine, Lidocaine, Procainamide, Mexiletine, Flecainide, Moricizine, and Disopyramide. Identifying other polymorphic forms of human cardiac sodium channel will advance our understanding of sodium channel-related heart problems and provide new tools for developing diagnostic, prophylactic and therapeutic strategies.

The art is uncertain as to whether any of the three polymorphic SCN5A isolates encodes a standard or reference hNa$_v$1.5 protein. This uncertainty precludes a well-reasoned analysis of mutations at particular amino acid residues in a consistent background. It is important to employ channel proteins having a suitable genetic background when evaluating one or more mutations of interest so that the actual effect of the mutations is noted. In addition, when studying possible direct and indirect drug interactions with cardiac channels, it is important to assess those interactions in the proper context. The full import of the genetic background of mutations in hNa$_v$1.5 has not heretofore been understood.

BRIEF SUMMARY OF THE INVENTION

The present invention relates to novel hNa$_v$1.5 sodium channel α subunit polypeptides designated as SCN5A variants [H558;Q1077], [H558R], [Q1077del] and [H558R; Q1077del], as well as polynucleotides that encode the polypeptides. The novel hNa$_v$1.5 polypeptides differ from the previously reported hH1, hH1a and hH1b sequences at amino acid positions 559, 618 and 1027.

The present invention is of particular interest in that the art has heretofore presumed that hH1, hH1a or hH1b encoded the "wild-type" or "reference" background sequence against which the effects of various SCN5A mutations should be judged. It is disclosed herein, however, that the disclosed sequences are observed in hundreds of individuals tested, establishing that they are the true standard background sequences in humans. The impact of selecting a proper background sequence when evaluating cardiac sodium channels is demonstrated herein in the Example below by showing the differential effect of a single amino acid change placed upon the background peptides of the invention as opposed to the same change placed upon the prior hNa$_v$1.5 peptides.

The present invention also includes various related nucleic acid molecules and polypeptides that are useful in various applications such as detecting the subunit and generating antibodies to the subunit. The present invention also relates to cloning and expression vectors and cells containing same. In addition, the present invention includes methods for screening for an agent for altering (increasing or reducing) sodium channel activities. Furthermore, methods of using the nucleic acids and polypeptides to detect the SCN5A variants disclosed herein and to generate antibodies to detect and purify the variants are also included in the present invention. New diagnostic and treatment strategies for various sodium channel-related diseases and conditions are also enabled by the present invention. The polypeptides of the SCN5A variants find particular application for use as a background into which putative disease causing mutations are introduced for functional analyses, where the background is more representative of the population than prior human cardiac sodium channels, particularly more representative than hH1, which has been considered a de facto standard channel, even though the inventors have determined that it is not widely distributed in the population at large.

It is an object of the present invention to identify some of the most common forms of a human cardiac sodium channel.

It is another object of the present invention to provide new tools for designing diagnostic and treatment strategies for sodium channel related diseases and conditions.

It is an advantage of the present invention that the SCN5A amino acid sequences are common in the human population.

It is a feature of the present invention that an SCN5A polypeptide of the invention has a threonine at amino acid position 559, a leucine at amino acid position 618, an arginine at amino acid position 1027 and a histidine or arginine at amino acid position 558, and either has a glutamine at amino acid position 1077 or misses the glutamine at the 1077 position due to alternative mRNA splicing. Examples of the polypeptides of the present invention include but are not limited to SEQ ID NO:2, 4, 6 and 8. It is further understood by the inventors that the polypeptides of the invention represent suitable background protein sequences upon which one or more further mutations can be introduced using standard methods known in the art and that use of a polypeptide comprising 20 or fewer amino acid differences from SEQ ID NO:2, 4, 6 or 8 over the length of SEQ ID NO:2, 4, 6 or 8, is within the scope of the invention. More preferably the altered polypeptide comprises 10 or fewer differences, or 5 or fewer, and most preferably a single difference, from SEQ ID NO:2, 4, 6 or 8.

An additional set of polypeptides of the invention further comprise a leucine at position 1766, but otherwise retain the amino acid sequences of the aforementioned set of polypeptides.

In a related aspect, the invention also relates to an isolated polynucleotide that encodes any of the aforementioned polypeptides of the invention. A polynucleotide of the invention can be an isolated nucleic acid molecule such as an mRNA molecule, a single or double stranded DNA molecule or a cDNA molecule, whether or not provided on a cloning vector or expression vector, as well as the complement of any of the foregoing. If the polynucleotide is a nucleic acid molecule provided on an expression vector, it can contain such upstream and/or downstream regulatory elements as are needed to support transcription and translation of the polynucleotide of the invention.

Other objects, advantages and features of the present invention will become apparent from the following specifications and claims.

DETAILED DESCRIPTION OF THE INVENTION

Figure 1:
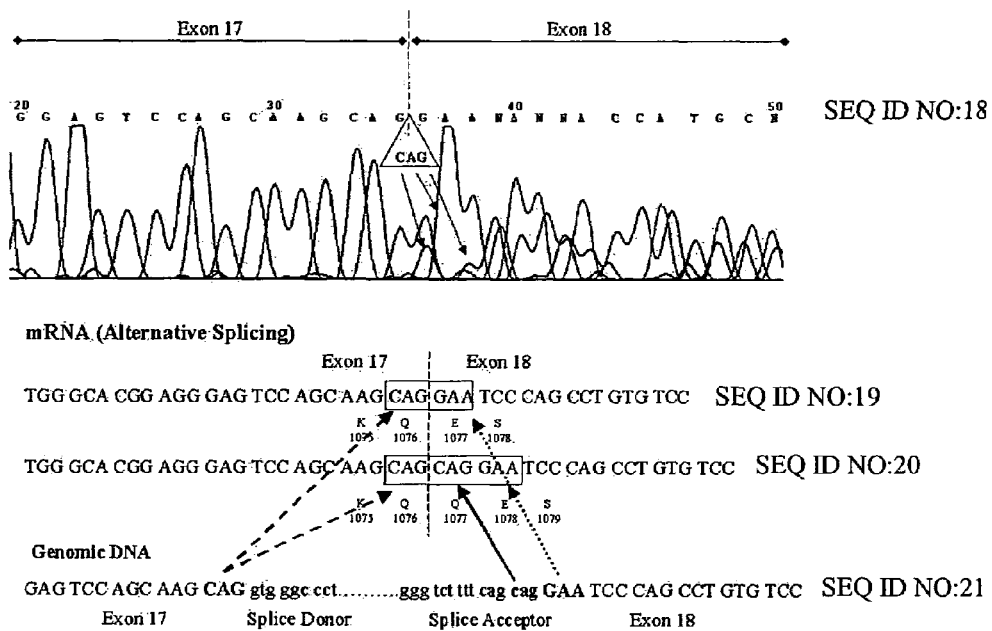
FIG. 1 shows alternative splicing of SCN5A at Exon 18. The top panel shows an example of sequencing data of RT-PCR products from mRNA isolated from human ventricle (see Example below). Note the single sequence present in the Exon 17 coding region, but a dual sequence in the exon 18 coding region. The splice acceptor site in the genomic DNA has two "cag" repeats leading to the alternative splicing of a glutamine at position 1077. This results in two splice variants, one of 2015 amino acids (mRNA top) and one with 2016 amino acids (mRNA bottom).

It is disclosed here that none of the existing SCN5A clones (hH1, hH1a and hH1b) represents a common sequence for SCN5A because each contains a rare variant at one or more of amino acid positions 559, 618 and 1027 (see Table 1). The inventors have identified four groups of SCN5A variants that represent the most common SCN5A variants with regard to the above amino acid positions as well as two additional positions, 558 and 1077. The SCN5A background can be important for the function of disease causing mutations. For example, the Brugada syndrome mutation T1620M showed a trafficking defect only with the relatively uncommon variant R1232W in the background (Baroudi, G. et al., *Circulation Research* 90:E11-E16, 2002). In another example, the H558R background affected the kinetics of the conduction disease mutation T512I (Viswanathan, P C et al., *J. Clin. Invest.* 111:341-346, 2003). In the Example below, M1766L arrhythmia mutation affected SCN5A trafficking only in the [1077del] background but not [H558R;1077del] background. Thus, it is important to study and test disease-causing or potentially disease-causing mutations in a relevant SCN5A background. It is also important to use a relevant SCN5A background for drug screening. Information on SCN5A background of a patient can be important for diagnostic and therapeutic purposes. The disclosure of the most common SCN5A variants here provides new tools to conduct SCN5A-related tests.

All four groups of SCN5A variants identified by the inventors have a threonine at amino acid position 559, a leucine at amino acid position 618 and an arginine at amino acid position 1027. However, they differ at amino acid positions 558 and 1077. Group 1 has a histidine at amino acid position 558 and a glutamine at amino acid position 1077. Group 2 has an arginine at amino acid position 558 and a glutamine at amino acid position 1077. Group 3 has a histidine at amino acid position 558 with the glutamine at amino acid position 1077 deleted. Group 4 has an arginine at amino acid position 558 with the glutamine at amino acid position 1077 deleted. Other positions of the SCN5A variants in these four groups can vary. For example, amino acid position 1103 for all groups can either be a serine (majority of the overall population) or a tyrosine (13.2% of the black population). The expected overall population frequencies for variant groups 1-4 are 24.5%, 10.5%, 45.5% and 19.5%, respectively. An example of an SCN5A amino acid sequence for each of the variant groups 1-4 is provided as SEQ ID NO: 2, 4, 6 and 8, respectively. The corresponding nucleotide sequences are SEQ ID NO:1, 3, 5 and 7, respectively.

The presence or absence of a glutamine at position 1077 is believed to arise from alternative mRNA splicing as part of the normal protein expression process. An individual can be homozygous or heterozygous for histidine or arginine at position 558. Individuals who are heterozygous at position 558 would, therefore, be expected to have all four forms of the hNa$_v$1.5 ion channel. Position 558 is believed to be located at or near a site of protein kinase A (PKA) phosphorylation in hNa$_v$1.5 sodium ion channels, and this amino acid position may play a role in regulation of the channel function.

For purpose of the present invention, the amino acids of the SCN5A variants are numbered by referring to the 2016 amino acid sequence GenBank Accession No. AC137578. Thus, in a variant with a 1077 deletion, the amino acid after amino acid 1076 is numbered 1078 so that the last amino acid is still 2016 instead of 2015. For example, the recently described polymorphism that appears to predispose to ventricular ectopy would be referred to as S1103Y (Chen, S. et al., *J. Med. Genet.* 39:913-915, 2002) rather than "Y1102" (Viswanathan, P C et al., *J. Clin. Invest.* 111:341-346, 2003). Channels with sequence variations from the reference sequence are denoted by the amino acid substitutions separated by semicolons and contained in brackets. Accordingly, SCN5A variant groups 1-4 as disclosed here are referred to as [H558;Q1077], [H558R], [Q1077del], and [H558R; Q1077del], respectively. It is noted that in the attached sequence listing, the amino acids in SEQ ID NO:6 and 8 are numbered under the 2015 system because the PatentIn program automatically numbers the amino acids consecutively.

The term "isolated nucleic acid" or "isolated polypeptide" used in the specification and claims of the present invention means a nucleic acid or polypeptide isolated from its natural environment or prepared using synthetic methods such as those known to one of ordinary skill in the art. Complete purification is not required in either case. Amino acid and nucleotide sequences that flank a polypeptide or polynucleotide that occurs in nature, respectively, can but need not be absent from the isolated form. The polypeptides and nucleic acids of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure and most preferably at least about 99% pure.

Further, an isolated nucleic acid has a structure that is not identical to that of any naturally occurring polynucleotide or to that of any fragment of a naturally occurring genomic polynucleotide spanning more than three separate genes. An isolated nucleic acid also includes, without limitation, (a) a polynucleotide having a sequence of a naturally occurring genomic or extrachromosomal nucleic acid molecule but which is not flanked by the coding sequences that flank the sequence in its natural position; (b) a polynucleotide incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are polynucleotides present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

In one aspect, the present invention relates to an isolated polypeptide comprising the amino acid sequence of an SCN5A variant disclosed herein. The SCN5A variant can be any SCN5A sequence that has a threonine at amino acid position 559, a leucine at amino acid position 618, an arginine at amino acid position 1027, a histidine or arginine at amino acid position 558, and a glutamine or glutamine deletion at amino acid position 1077. Examples amino acid sequences of an SCN5A variant are provided as SEQ ID NO:2, 4, 6 and 8. Generally speaking, an SCN5A variant of the present invention will not differ from SEQ ID NO:2, 4, 6 or 8 at more than 20 amino acid positions other than positions 558, 559, 618, 1027 and 1077. Preferably, the difference is limited to 10 or fewer, more preferably 5 or fewer, and most preferably 1 or fewer positions. However, it is understood that substitutions such as a conservative substitution can be introduced into non-critical amino acid positions and this will not materially affect the function even when more than 20 amino acids are substituted. An SCN5A variant with such substitutions is within the scope of the present invention.

Furthermore, an isolated polypeptide of the invention can also include one or more amino acids at either or both of the N-terminus and C-terminus of an SCN5A variant disclosed herein, where the additional amino acid(s) do not materially affect the function of the variant, which can be determined using the parameters shown in Table 3. Any additional amino acids can, but need not, have advantageous use in purifying, detecting, or stabilizing the polypeptide. Likewise, small deletions or other rearrangements in the polypeptide that do not affect the function of the polypeptide are also within the scope of the invention. Such deletions are preferably deletions of fewer than 100 amino acids, more preferably of fewer than 50 amino acids, still more preferably of fewer than 10 amino acids.

In a related aspect, the present invention also includes an immunogenic fragment of an SCN5A variant disclosed herein and an antibody that binds specifically to such an immunogenic fragment. Such immunogenic fragments are used to generate specific antibodies that can be used to detect or isolate an SCN5A variant of the present invention, or both. In general, the immunogenic fragments contain at least 15 continuous amino acids, preferably at least 20 continuous amino acids, and most preferably at least 25 continuous amino acids of an SCN5A variant in which the continuous amino acids include position 558. An antibody that is specific for a variant of the present invention will have a higher affinity for the variant than for hH1, hH1a, or hH1b. It is well within the ability of a skilled artisan to make monoclonal or polyclonal antibodies against some or all of the polypeptides and to assess the specificity of the antibodies. Furthermore, as it is now shown by the inventors that the variants disclosed herein are the "common" or "standard" forms of the $hNa_v1.5$ protein, an antibody that merely identifies the protein may be sufficient for various uses, without regard to its specificity relative to hH1, hH1a and hH1b.

In another aspect, the present invention relates to an isolated nucleic acid containing a coding polynucleotide or its complement wherein the coding polynucleotide has an uninterrupted sequence that encodes a polypeptide of the invention as set forth above. A nucleic acid containing a polynucleotide that is at least 80% identical to the coding polynucleotide or its complement over the entire length of the coding polynucleotide can be used as a probe for detecting the coding polynucleotide and is thus within the scope of the present invention.

In a related aspect, any nucleic acid of the present invention described above can be provided in a vector in a manner known to those skilled in the art. The vector can be a cloning vector or an expression vector. In an expression vector, the polypeptide-encoding polynucleotide is under the transcriptional control of one or more non-native expression control sequences which can include a promoter not natively found adjacent to the polynucleotide such that the encoded polypeptide can be produced when the vector is provided in a compatible host cell or in a cell-free transcription and translation system. Such cell-based and cell-free systems are well known to the skilled artisan. Cells comprising a vector containing a nucleic acid of the invention are themselves within the scope of the present invention. Also within the scope of the present invention is a host cell having the nucleic acid of the present invention integrated into its genome at a non-native site. Further, the above cells of the present invention can contain SCN5A variants from more than one of the four variant groups.

The present invention also includes an isolated nucleic acid molecule that contains a fragment of at least 12, 15, 20 or 25 contiguous nucleotides of an SCN5A variant disclosed herein, or its complement, particularly a fragment that comprises codon 558, 1077, or both. Such a nucleic acid molecule can be used to detect the expression of the SCN5A variant in a cell. The detection reaction can be run under stringent hybridization conditions, for example, by hybridizing at 68° C. in 5×SSC/5× Denhardt's solution/1.0% SDS, and washing in 0.2×SSC/0.1% SDS at room temperature. Moderately stringent conditions which include washing in 3×SSC at 42° C. can also be used.

The present invention also enables a screening method for agents that can either inhibit or enhance sodium channel activities. In such a method, an agent is exposed to a host cell of the present invention that expresses one or more SCN5A variants disclosed herein and the agent's effect on the variants' activities is determined by comparing to control cells that are not exposed to the agent. The activity of an SCN5A variant can be measured in many ways, including but not limited to measuring a sodium current across the cell membrane, a sodium current kinetic activity, a membrane potential, or an intracellular sodium level. Agents that can modulate the expression of an SCN5A variant can be screened similarly using cells which contain the variant whose expression is controlled by the native expression control sequences. Also, a phenotype associated with over-expression of a sodium channel or absence of expression (e.g., in a transgenic or knockout animal) can be monitored. In vitro, an effect on action potential can be measured after a channel of interest is transfected into suitable cells, such as cardiac cells. An arsenal of agents affecting the sodium channel activity is desired because many diseases and conditions, such as arrhythmias and Brugada syndrome, result from elevated or reduced sodium channel activity. Particularly in view of the understanding that various forms of the sodium channel α subunit differ functionally, it is important to evaluate the effects of every form that may be present in an individual. Indeed, one can tailor a suitable treatment to an individual after evaluating the form of a subunit present in that individual. Sodium channel activity means the open channel activity leading to a peak sodium current. Sodium channel activity is enhanced or inhibited when the open state probability is greater or less, and the peak current is higher or lower, respectively, than in the absence of a modulating agent.

The human embryonic kidney cell line (HEK) described in the Example below is a suitable cell line that can be transfected with various SCN5A constructs of the present invention to screen for agents that can affect the function of an SCN5A variant. This cell advantageously lacks endogenous SCN5A proteins to interfere with the signal from a transfected SCN5A of interest. However, other suitable cells can also be used. If a cell, such as a heart cell, which expresses endogenous SCN5A is used, the signal attributable to the endogenous protein must be subtracted when the activity of a transfected SCN5A is measured.

Batteries of agents for screening are commercially available in the form of various chemical libraries including peptide libraries. Examples of such libraries include those from ASINEX (e.g., the Combined Wisdom Library of 24,000 manually synthesized organic molecules) and from CHEM-BRIDGE CORPORATION (e.g., the DIVERSet™ library of 50,000 manually synthesized chemical compounds; the SCREEN-Set™ library of 24,000 manually synthesized chemical compounds; the CNS-Set™ library of 11,000 compounds; the Cherry-Pick™ library of up to 300,000 compounds). Once an agent having desired ability to increase or decrease activity of the sodium channel protein is identified, further iterations of the screen using one or more libraries of derivatives of that agent can be screened to identify agents having superior effects.

The above screening methods also enable one to determine the likelihood that an agent intended to be administered to a human or non-human subject will induce an undesired and unintended side effect, namely by altering the activity of the cellular SCN5A in the subject.

The present invention also enables a skilled artisan to determine whether a mutation is associated with a sodium channel-related disease on a common SCN5A background. To do this, a mutation is introduced into an SCN5A variant disclosed herein and the effect of the mutation is then tested in a suitable model for the disease.

The polypeptides, polynucleotides and antibodies of the invention find particular utility as screening tools for identifying to which of the four SCN5A groups a particular subject belongs. This information is useful in several aspects. For example, it may help assess the subject's predisposition to acquired arrythmias. For instance, if a subject has a high proportion of low-expressing channels such as [H558R], the subject could be predisposed to develop acquired arrythmias. Also, for a subject that suffers from a sodium channel-related disease, knowing the SCN5A background of the subject can help choose treatment strategies.

With the disclosure herein, it is well within a skilled artisan's ability to determine to which of the four SCN5A groups a subject belongs. Such determination can be made at the polynucleotide level or protein level. At the polynucleotide level, primers and probes that specifically amplify or hybridize to each of the four SCN5A groups can be used. Alternatively, direct sequencing can also be used. At the protein level, antibodies specific for each of the four SCN5A groups can be developed and used. Alternatively, the amino acid sequence of an SCN5A protein can be determined directly.

Any product of the invention described herein can be combined with one or more other reagent, buffer or the like in the form of a kit useful, e.g., for diagnostic or therapeutic purposes, in accord with the understanding of a skilled artisan.

The present invention is not intended to be limited to the foregoing, but rather to encompass all such variations and modifications as come within the scope of the appended claims. The invention will be more fully understood upon consideration of the following Examples which are, likewise, not intended to limit the scope of the invention.

EXAMPLE

Materials and Methods

Genotyping for residues 558, 559, 618 and 1027: Allele frequencies for the SCN5A variants (H558R in exon 12, T559A in exon 12, L618I in exon 12, and R1027Q in exon 17) were established by direct genomic DNA sequencing of 400 reference alleles derived from the 100 Caucasian human variation panel and the 100 African-American human variation panel (Coriell Cell Repositories and the National Institute of General Medical Sciences). Protein-encoding sequences harboring these variants were amplified by polymerase chain reaction (PCR) using previously published intron/exon based primers 5 and subsequently sequenced using automated dye-terminator cycle sequencing on an ABI Prism 377. The fluorescent detection stems from reporter dyes bound to the ddNTP terminator nucleotides. The Big-Dye Terminator Cycle Sequencing v 1.0 kit from Applied Biosystems (ABI part# 4303154) was used for sequencing of all samples. To determine the status at residues 558, 559, and 618, SCN5A exon 12 was analyzed by PCR amplification of two overlapping fragments 12A (forward primer—GC-CAGTGGCTCAAAAGACAGGCT (SEQ ID NO:9) and reverse primer—CCTGGGCACTGGTCCGGCGCA (SEQ ID NO:10)) and 12B (forward primer—CACCACACAT-CACTGCTGGTGC (SEQ ID NO:11) and reverse primer—GGAACTGCTGATCAGTTTGGGAGA (SEQ ID NO:12)). PCR amplification reactions for amplicons 12A and 12B were performed in 20 μL volumes using 50 ng of genomic DNA, 16 pmol of each primer, 200 μM of each dNTP, 50 mM KCl, 10 mM Tris-HCl (pH 8.3), 2.0 mM $MgCl_2$, and 1.0 U of Amplitaq Gold (Applied Biosystems, Branchburg, N.J.). The reaction mixture was subjected to a 95° C. initial denaturation for 5 min, followed by 5 cycles of 94° C. for 20 s, 64° C. for 20 s, and 72° C. for 30 s; then an additional 35 cycles of 94° C. for 20 s, 62° C. for 20 s, 72° C. for 30 s, and a final extension of 72° C. for 10 min. PCR reactions used to amplify SCN5A exon 17 (R1027Q variant) were performed in 20 μL volumes using 50 ng of genomic DNA, 16 pmol of each primer (forward primer—GCCCAGGGCCAGCTGCCCAGCT (SEQ ID NO:13) and reverse primer—CTGTATATGTAGGTGC-CTTATACATG (SEQ ID NO:14)), 200 pM of each dNTP, 50 mM KCl, 10 mM Tris-HCl (pH 8.3), 1.0 mM $MgCl_2$, 8%

DMSO and 1.0 U of Amplitaq Gold (Perkin-Elmer). The cycling conditions were as follows: 94° C. initial denaturation for 10 min, followed by 40 cycles of 94° C. for 30 s, 60° C. for 30 s, 72° C. for 30 s, and a final extension of 72° C. for 10 min. PCR products for exon 12 (12A and 12B) and exon 17 were enzymatically treated to remove unincorporated dNTP and primers with EXOSAP-it (USB Inc., Cleveland, Ohio) following the manufacturer's protocol. Treated products were sequenced using dye-terminator cycle sequencing with an ABI 377, and the resulting chromatograms were analyzed for the specific variant.

Identification, characterization, and quantification of alternatively-spliced SCN5A transcripts encoding for either insertion or deletion of glutamine (Q) at residue 1077: Direct DNA sequencing was performed on exon 17/18 targeted RT-PCR generated products derived from messenger RNA that was extracted from myocardial tissue obtained at either i) autopsy of sudden infant death syndrome (n=5), non-accidental infant death (n=5), or accidental adult death victims (n=5) or ii) surgical myectomy in adults with hypertrophic cardiomyopathy (n=5). Total RNA from an approximate 25 mg piece of heart tissue was isolated using the Rneasy™ Fibrous Tissue Mini kit (Qiagen, Valencia, Calif.), and first-strand cDNA synthesis was performed in triplicate on 500 ng of total RNA using the iScript™ cDNA Synthesis kit (BioRad, Hercules, Calif.) following the manufacturer's specifications. PCR was performed in 20 µL volumes using 2 µL of cDNA, 16 pmol of each primer (17F forward: CCAAGAAGAGGATGAG-GAGA (SEQ ID NO:15),18R reverse: GAGGCAGTCGCT-GACACC (SEQ ID NO:16)), 200 µM of each dNTP, 50 mM KCl, 10 mM Tris-HCl (pH 8.3), 2.0 mM $MgCl_2$, and 1.0 U Amplitaq Gold (Perkin-Elmer). The cycling conditions were as follows: 94° C. initial denaturation for 10 min, followed by 35 cycles of 94° C. for 30 s, 58° C. for 30 s, 72° C. for 30 s, and a final extension of 72° C. for 10 min. PCR products were purified with EXOSAP-it (USB Inc., Clevland, Ohio) and sequenced using an automated AB1377 sequencer (Applied Biosystems, Inc., Foster City, Calif.). The relative quantity of the 2 alternatively-spliced transcripts was then quantified. Triplicate cDNA samples from each case were subject to PCR amplification using the same PCR primers and conditions as above, with the addition of 0.2 µl of alpha-$^{32}$P dCTP (10 mCi/ml). Since all samples were shown to harbor both transcripts by direct DNA sequencing, control templates representing homozygous Q1077 and Q1077de1 transcripts were synthesized and PAGE purified by Integrated DNA technologies, Inc. (Coralville, Iowa). The resulting radionucleotide incorporated PCR products representing 1) the transcript (135 base pairs) encoding the insertion of glutamine at residue 1077 (Q1077) or 2) the transcript (132 base pairs) that does not encode for glutamine at residue 1077 (Q 1077de1) were separated by denaturing gel electrophoresis at 70 watts for 2 hrs and 45 min on a 6% polyacrylamide (19:1), 7 M urea gel. Autoradiography with a phosphoimager 445 SI and ImageQuant v 5.0 software (Molecular Dynamics, Piscataway, N.J.) were used for signal quantification of the two alternatively-spliced transcripts.

Gene expression, mutagenesis, and nomenclature: The SCN5A clone hH1 (GenBank No. M77235) was kindly provided by Dr. Al George (Gellens, M E et al., *Proc. Natl. Acad. Sci. U.S.A* 89:554-558, 1992, which is herein incorporated by reference in its entirety) in prcCMV (Invitrogen). The hH1c construct (GenBank No. AY148488) was made from the hH1b clone (GenBank AF482988) (Ye, B. et al., *Physiol. Genomics* 12:187-193, 2003, which is herein incorporated by reference in its entirety) by mutating the arginine (R) at 558 to histidine (H), and the isoleucine (I) at positions 618 to leucine (L) by methods described below. The consensus reference sequence (GenBank No. NM_000335 June 2003) has 2015 amino acids and is identical to hH1c. For naming and reference purposes we prefer the full-length 2016 amino acid deduced sequence from the IHGSC (GenBank No. AC137587, deposited April 2003) as the base sequence for SCN5A because this nomenclature retains the well-established numbering system based upon the 2016 amino acids encoded by the original SCN5A clone hH1 (Gellens, M E et al., *Proc. Natl. Acad. Sci. U.S.A* 89:554-558, 1992). Channels with sequence variations from the reference sequence are denoted by the amino acid substitutions separated by semicolons and contained in brackets as recommended by den Dunnen and Antonarakis (den Dunnen, J T et al., *Hum. Mutat.* 15:7-12, 2000). The variant channels [H558R], [Q1077de1], [H558R;Q1077de1], [H558R;Q1077de1;M1766L], and [Q1077de1;M1766L] were made by mutagenesis at appropriate residues by the following method.

Mutations were generated using Excite® mutagenesis kit (Stratagene, La Jolla, Calif.) using the protocol suggested by the manufacturer. DNA was isolated and purified with the Qiagen (Valencia, Calif.) column and protocol. All constructs were sequenced to verify incorporation of the intended amino acid change and to confirm that no unwanted changes were introduced. These constructs were placed in pcDNA3 (Invitrogen, Carlsbad, Calif.) and expressed in HEK293 cell line by transfection with 1.5 µg of plasmid DNA using Superfect (Qiagen) according to the protocol recommended by the manufacturer. A GFP protein was co-transfected (at 1:10) as a marker to identify the transfected cells. HEK 293 cells were harvested 24 hours after transfection to measure macroscopic current as previously described (Nagatomo, T. et al., *Am. J. Physiol.* (*Heart* 44) 275:H2016-H2024, 1998, incorporated by reference in its entirety). Experiments were done with transient transfection unless otherwise noted. A few experiments used cell lines expressing these variants in a stable manner. For these stable cell lines, pcDNA3 (Invitrogen) plasmid DNA containing the hNav1.5 α subunit was transfected into HEK-293 cells and selected as follows. Approximately $1 \times 10^5$ cells were plated on a 60 mm diameter plate (Falcon 3001) approximately 24 hours prior to transfection in 3 mL MEM-complete media (Minimal Essential Media (Gibco/Invitrogen) supplemented with 2 mM L-glutamine, 10% Fetal Bovine Serum, 1 mM sodium pyruvate solution, 0.1 mM non-essential amino acids, 10,000 U of Penicillin and 10,000 mg of streptomycin). 1.5 µg of plasmid DNA was mixed along with 10 µL of Superfect reagent (Qiagen) into 140 µL of Opti-MEM (Gibco/Invitrogen) and allowed to incubate at room temperature for 10 min to allow for the DNA to bind to the Superfect. The HEK cells were then incubated with this DNA and Superfect solution in 1 mL MEM-complete for 3.5 hrs, at which point the media was replaced with 3 mL of MEM-complete. 24 hours post-transfection 800 ng/mL of G418 antibiotic was added. MEM-complete+G418 medium was thereafter replaced every 72 to 96 hours. After 3-4 weeks, single colonies were isolated from the transfected plate and grown in separate wells of a 6-well plate (Costar 3516, Corning, N.Y.). RNA was isolated (RNAisol from LPS, Moonachie, N.J.) and screened by RT-PCR analysis. Colonies that tested RT-PCR-positive were then analyzed by voltage clamp.

Voltage-clamp techniques: The whole cell patch-clamp technique was utilized to measure macroscopic $I_{Na}$ (Nagatomo, T. et al., *Am. J. Physiol.* (*Heart* 44) 275:H2016-H2024, 1998). The pipette solution contained 120 mM CsF, 15 mM CsCl, 2 mM EGTA, 5 mM HEPES and 5 mM NaCl (pH7.4 with CsOH). Data were recorded at room temperature using pCLAMP 8 (Axon Instruments). The voltage-clamp protocols are described briefly with the data and have been published previously in detail (Valdivia, C R et al., *J. Mol. Cell Cardiol.* 34:1029-1039, 2002). Peak $I_{Na}$ and late $I_{Na}$ were obtained after passive leak subtraction as described previously (Nagatomo, T. et al., *Am. J. Physiol.* (*Heart* 44) 275: H2016-H2024, 1998). Parameter fits were obtained using Clampfit 8 (Axon Instruments). One way ANOVA was performed to determine statistical significance among 3 or more groups of mean data. Statistical significance was determined by a P value<0.05.

Immunocytochemistry: The FLAG epitope was introduced between S1 and S2 in domain I for channels used in the immunocytochemistry experiments. Transfected and non-transfected HEK293 cells were fixed with 4% paraformaldehyde at room temperature for 20 minutes. The fixed cells were blocked with 5% goat serum and 0.2% Triton PBS solution at room temperature for 30 minutes. After the blocking procedure, the cells were incubated with the mouse anti-FLAG M2 primary antibody (Stratagene®, La Jolla, Calif.) at the ratio of 1:2000 overnight at 4° C. On the next day, the cells were washed with PBS before 1:100 fluorescein-conjugated goat anti-mouse antibody (Jackson, West Grove, Pa.) was applied as the secondary antibody and allowed to react for 1 hour at room temperature in the dark. The rabbit anti-Calnexin IgG was used as endoplasmic reticulum (ER) marker to test for co-localization. A 1:1000 dilution of the rabbit anti-Calnexin IgG in 250 μl was applied to transfected cells immediately after incubation with fluorescein-conjugated goat anti-mouse secondary antibody. The reaction was incubated for 2 hrs at 37° C. After incubating with anti-Calnexin IgG, the cells were washed twice with 300 μl of PBS and incubated with 150 μl of Texas Red-conjugated goat anti-rabbit secondary antibody (Jackson, West Grove, Pa.) at the ratio of 1:100. The incubation with Texas Red-conjugated goat anti-rabbit 2nd antibody was done at room temperature in the dark for 1 hour. The cells were washed with PBS solution and fixed with a solution containing 90% glycerol and 10% Na carbonate. A Bio-Rad MRC 1024 Laser Scanning system with 15 mW mixed gas (Krypton/Argon) laser was utilized to view immunofluorescently labeled cells. The Bio-Rad MRC 1024 system was mounted on a Nikon Diaphot 200 inverted microscope. Images of the fluorescent-labeled cells were scanned under 40× objective and 2× zoom. The confocal system was set to 3.6 for iris, laser power at 100% and camera sensitivity gain to 900. A Kalman collection filter with 5 frames per image was applied to record the image.

Results

Sequence comparisons for SCN5A clones and genotyping of control panels: The sequences of hH1 (Gellens, M E et al., *Proc. Natl. Acad. Sci. U.S.A* 89:554-558, 1992), hH1a (Hartmann, H A et al., *Circulation Research* 75:114-122, 1994, which is herein incorporated by reference in its entirety), and hH1b (Ye, B. et al., *Physiol. Genomics* 12:187-193, 2003) were compared and the amino acid differences at 5 residues are shown in Table 1 along with the GenBank Accession number where available. In a previous study of the hH1b clone (Ye, B. et al., *Physiol. Genomics* 12:187-193, 2003), hH1 and hH1a were re-sequenced and the differences between these two clones were found to be only the 3 residues shown in Table 1 rather than the 9 reported previously.

TABLE 1

Comparisons for deduced SCN5A/Na$_v$ 1.5 sequences from full-length cDNA clones (hH1, hH1a, hH1b), genomic sequencing (hH1c) and genomic databases (Celera, 1HGSC).

| SCN5A Variant Group | 1 | 2 | | | 3 | 4 | |
|---|---|---|---|---|---|---|---|
| Common[a] Name | IHGSC | | hH1 | hH1a | hH1b | hH1c[d] | |
| Accession No.[b] | AC137587 | NA | M77235 | NA | AF482988 | AY148488 | NA |
| AA[c] No. 558 | R | R | H | H | R | H | R |
| 559 | T | T | T | A | T | T | T |
| 618 | L | L | L | L | I | L | L |
| 1027 | R | R | Q | R | R | R | R |
| 1077 | Q | Q | Q | Δ | Δ | Δ | Δ |
| Variant[e] name | [H558; Q1077] | [H558R] | [R1027Q] | [T559A; Q1077del] | [H558R; L618I; Q1077del] | [Q1077del] | [H558R; Q1077del] |
| Population[f] Frequency | 24.5% | 10.5% | 0% | 0% | 0% | 45.5% | 19.5% |

[a]IHGSC = International Human Genome Sequencing Consortium sequence and reference sequence; hH1, hH1a, hH1b = previously cDNA clones of SCN5A; hH1c = Common sequence from genomic sequencing in control subjects (a search of Celera human genome database identified the same sequence).
[b]Accession No. = GenBank Nucleotide accession numbers, where available.
[c]AA No. = Amino Acid residue number in the protein, using the full length numbering consistent with the IHGSC database as well as the originally isolated SCN5A. At all 2011 the positions not noted in the table above the amino acids are identical in all sequences. "Δ" indicates there is no amino acid present at this location in the amino acids (thus, the product is 2015 amino acids in length, rather than 2016). The amino acid frequencies in the population of all proteins in the population of all studied humans at positions 558, 559, 618, 1027 and 1077 are 70% H, 100% T, 100% L, 100% R and 65% Δ, respectively.
[d]A search of Celera human genome database identified the same sequence
[e]Variant name = name relative to [H558; Q1077] (defined herein as identical to IHGSC).
[f]Population Frequency = estimated percentage of protein products in the study population that have this sequence.

We investigated allelic frequencies from genomic DNA at the 5 positions in question from a panel of 200 human controls (100 white subjects and 100 black subjects). The most common residues at these 5 positions are reported as hH1c in Table 1. For positions 559, 618, and 1027, 100% of the 400 reference alleles showed T559, L618, and R1027, indicating that each of the existing clones contained a rare variant and that none represented the common sequence (Table 1). A search of the Celera human genome database showed that the deduced amino acid sequence agreed with hH1c. The deduced amino acid sequence in the NIH International Human Genome Sequencing Consortium (IHGSC) also agreed with the hH1c sequence. However, the IHGSC sequence contains the additional glutamine (Q) at position 1077 as found in the hH1 clone but not hH1a or hH1b.

A common polymorphism, H558R: Residue 558 hosts the common polymorphism involving a substitution of histidine (H) with arginine (R)H558R (Iwasa, H. et al., *J. Hum. Genet.* 45:182-183, 2000) with a reported frequency in the population of 19-24% (Yang, P. et al., *Circulation* 105:1943-1948, 2002). We confirm that H558R is a common polymorphism (Table 2) among both blacks and whites; the apparent higher incidence of H558R in blacks is not statistically significant. We also show the frequency of heterozygosity and homozygosity at this position (Table 2).

TABLE 2

Genotype and Allelic Frequency of H558R Polymorphism

| Ethnicity | Sample Size | HH | HR | RR | H allele | R allele |
|---|---|---|---|---|---|---|
| White | 100 | 65 | 30 | 5 | 0.8 | 0.2 |
| Black | 100 | 53 | 40 | 7 | 0.73 | 0.27 |

A common alternatively-spliced variant, Q1077del: The hH1 clone contained a glutamine (Q) residue at both amino acid positions 1076 (the final codon of exon 17) and 1077 (the first codon of exon 18) (Gellens, M E et al., *Proc. Natl. Acad. Sci. U.S.A* 89:554-558, 1992). The acceptor site sequence for exon 18 was annotated as ggggtcttttcagCAGGAATCC (SEQ ID NO:17) where the lower case letters represent the intronic sequences and the upper case letters represent the 5' exonic sequences of exon 18 (see FIG. 1). The underlined lower case letters indicate the predicted "ag" acceptor site rule for splice site recognition. However, splice-site analytical tools indicate that the CAG following the ag shown above could also comprise the terminal intronic sequence and may be the preferred acceptor site for splicing, resulting in a deletion of glutamine at residue 1077 (Q1077del).

Figure 2:
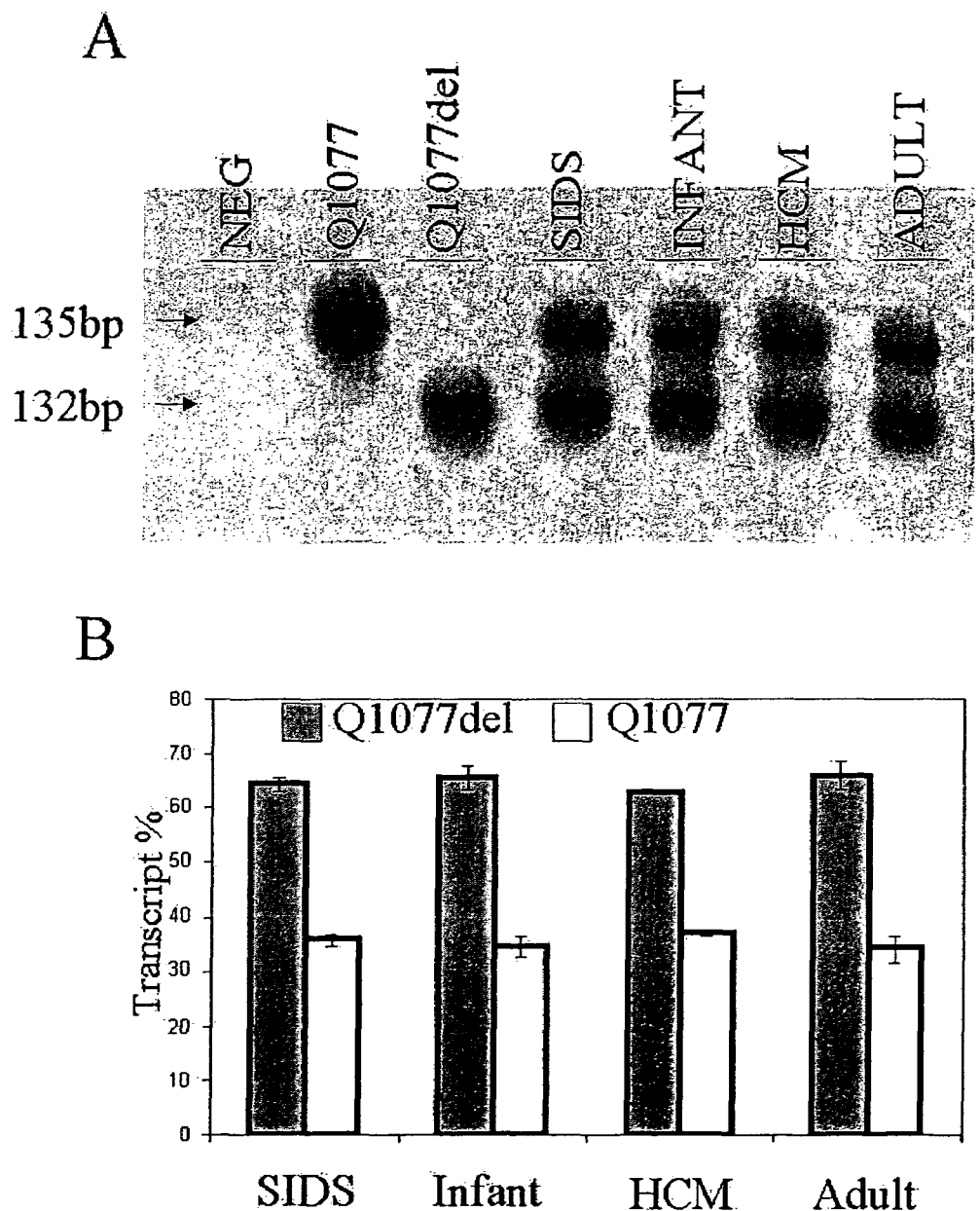
FIG. 2 shows quantitative analysis of alternatively spliced variant SCN5A transcripts that either encodes Q1077 or excludes Q1077 (Q1077del). (A) Examples of RT-PCR products from 3 control experiments and 4 subjects. A sample without DNA (NEG) served as a negative control, and synthesized template of 135 bp containing the "cag" repeat (Q1077) and template of 132 bp without the "cag" repeat (Q1077del) served as positive controls. RT-PCR from samples of mRNA taken at autopsy from a subject with sudden infant death syndrome (SIDS), an infant without structural heart disease (Infant), an adult with no structural heart disease (Adult), and from a myomectomy specimen from a patient with hypertrophic cardiomyopathy (HCM) all show the presence of both transcripts. (B) Summary data from 20 subjects (five in each group) show that the transcript coding for Q1077del was consistently more abundant relative to Q1077. Bars represent the mean and standard deviation of the relative abundance of each transcript from 5 subjects determined by autoradiography phoshoimaging.

To answer the question whether SCN5A most commonly has a glutamine (Q) at both amino acid positions 1076 and 1077 as in hH1 or only 1076 as in hH1a and hH1b, we performed direct sequencing on exon 17/18-targeted RT-PCR generated products derived from mRNA isolated from human left ventricular myocardial specimens from sudden infant death syndrome (SIDS), infants with structurally normal heart, adults with hypertrophic cardiomyopathy, and adults with structurally normal hearts. All subjects were heterozygous for a "cag" in-frame insertion indication the universal presence of alternative-splicing involving this acceptor site (FIG. 1). The relative abundance for each alternatively-spliced transcript was quantified by autoradiography and phosphoimaging (FIG. 2). Examples of RT-PCR products generated from myocardial RNA (FIG. 2A) show the expected size products for control experiments with the 135 bp template containing the extra cag codon (Q1077) and for the 132 bp template lacking the extra cag codon (Q1077del).

Summary data (FIG. 2B) show that Q1077del was the preferred alternatively-spliced variant being significantly more abundant in every group tested. Overall, the proportion of alternatively-spliced variant containing Q1077 was 35±2.0% (range 31-38%, n=20) and the Q1077del transcript was 65±2.0% (range 62-69, n=20). The total test group contained 9 males and 11 females, and the infant group contained 5 white and 5 black subjects. This degree of preferential splicing was not influenced by age, sex, race, or presence of ventricular hypertrophy. In addition, these ratios of Q1077 and Q1077del-transcripts were maintained regardless of whether RNA was obtained from right atrium, left atrium, right ventricle, or left ventricle.

Four common SCN5A variants in the human population: Based upon the predicted amino acid frequency estimates from our genomic sequencing in controls and our measurement of the frequency of the splice variant Q1077del, we estimated the population frequency of the existing clones and other full-length sequences (Table 1). These estimates assume independence between the probability of the Q1077del splice variant (65%) and the genomic variant containing H558R (30%). Note that the three clones hH1, hH1a, and hH1b used in previous studies are estimated to have a very low frequency in the population because of the presence of a rare variant in each. The most common variant [Q1077del] at 45.5% is identical to the hH1c sequence, the Celera sequence, and also to the NCBI Reference Sequence for SCN5A (GenBank Accession number NM_000335). The full-length reference sequence SCN5A ([H558;Q1077]) is actually less frequent than [Q1077del] at 24.5%. Only slightly less common are the variants with the H558R polymorphism designated as [H558R;Q1077del] at 19.5% and [H558R] at 10.5% (by our convention, the [H558R] variant contains Q1077).

Figure 3:
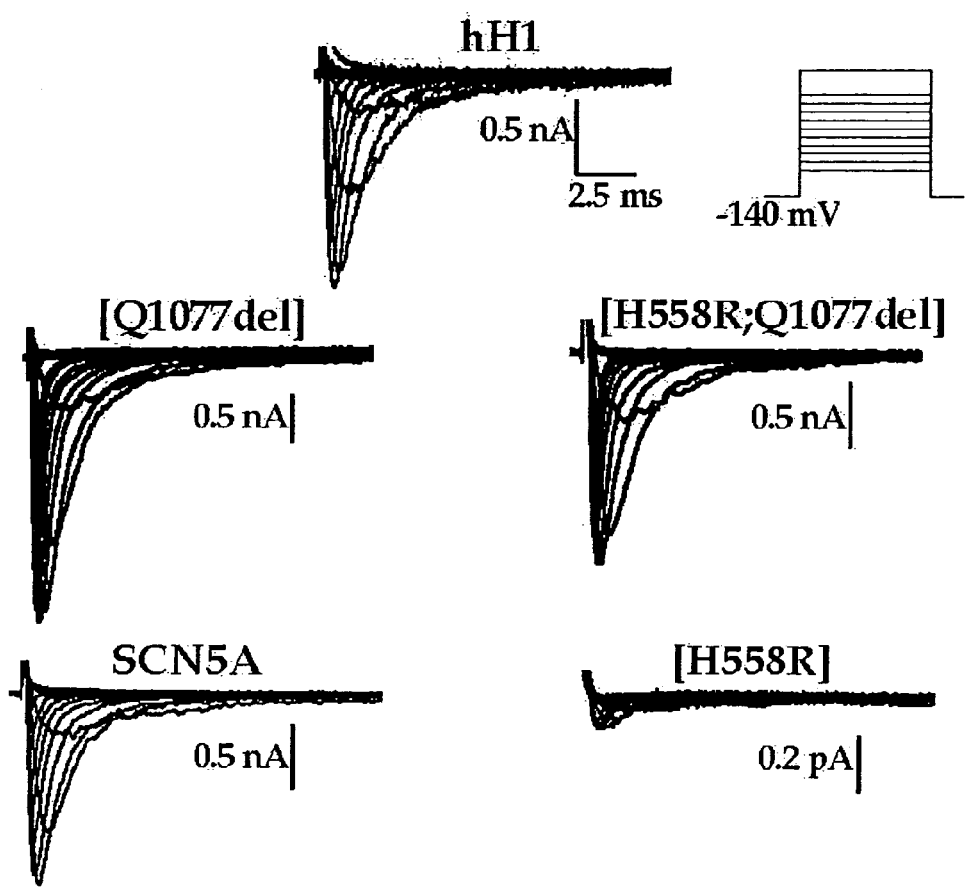
FIG. 3 shows voltage clamp data for SCN5A variants. Current traces for hH1 and four common SCN5A channel variants sequences are shown. Currents were elicited by step depolarizations from a holding potential of −140 mV to various test potentials of 24 ms duration from −140 mV to +60 mV. No obvious differences in current time course were noted
Figure 4:
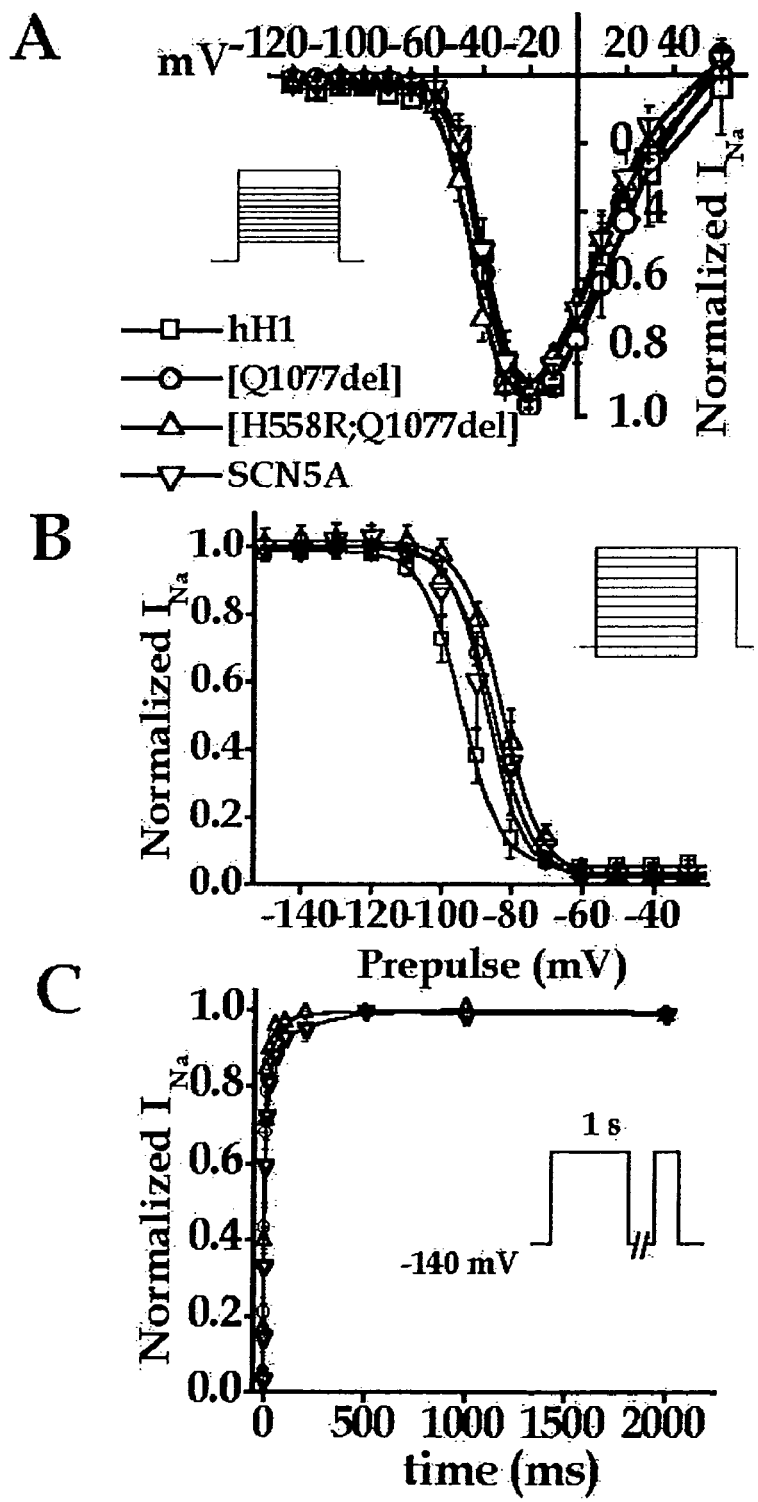
FIG. 4 shows activation, inactivation and recovery kinetics of SCN5 variants. (A) Summary data of peak current voltage relationships for currents obtained as in FIG. 3. Data were normalized to the peak $I_{Na}$ in each data set. The lines shown were generated by a Boltzmann function Gna=[1+exp ($V_{1/2}$−V)/K]$^{-1}$, where $V_{1/2}$ and K are the mid-point and the slope factor, respectively, and Gna=$I_{Na}$/(V−Vrev) where Vrev is the reversal potential. (B) Summary data for the voltage dependence of "steady-state" inactivation. $I_{Na}$ obtained in response to a test depolarization to 0 mV from a holding potential of −140 mV, following 1 sec conditioning step to the various conditioning potentials (Vc). In order to normalize the capacity transients a 0.2 ms step back to −140 was applied before a test depolarization. The voltage dependent availability from inactivation relationship was determined by fitting the data to the Boltzmann function: $I_{Na}$ $I_{Na-max}$[1+exp (Vc−$V_{1/2}$)/K]$^{-1}$, where the $V_{1/2}$ and K are the midpoint and the slope factor, respectively, and V is the membrane potential. (C) Summary data for recovery from inactivation. Recovery from inactivation was assessed using a two pulse protocol where a conditioning step of 1 sec to 0 mV inactivated $I_{Na}$ followed by a test pulse to 0 mV after a recovery period "t" at a recovery potential of −140 mV. The peak $I_{Na}$ in response to the test pulse was normalized to the maximum peak current and plotted versus "t." This recovery process was fit to the sum of two exponentials: Normalized $I_{Na}[A_f\exp(-t/\tau_f)]+[A_s\exp(-t/\tau_s)]$ where t is the recovery time interval, $\tau_f$ and $\tau_s$ are the fast and slow time constant, and $A_f$ and $A_s$ are the fraction of the recovery components.

Functional characterization of SCN5A variants: Constructs for expressing [H558;Q1077] and the other common variants [H558R], [Q1077del] and [H558R;Q1077del] were made and transfected individually into HEK cells for kinetic studies. For comparison, we expressed hH1 contemporaneously under the same conditions with these variants because most previous studies in the literature have used hH1. Representative currents for the four variants and hH1 are shown in FIG. 3. For those variants that expressed robust current, no significant differences were identified in i) the parameters of activation (FIG. 4A, Table 3), ii) current decay (Table 3), iii) recovery from inactivation (FIG. 4C, Table 3) and iv) late or persistent currents (Table 3). The midpoint of inactivation for hH1, however, was significantly negative to the two variants lacking Q1077 [Q1077del] and [H558R;Q1077del] (FIG. 4B and Table 3).

TABLE 3

Voltage-dependent Kinetic Parameters for hNa$_v$1.5 Channels

| | hH1 | [Q1077del] | [H558R; Q1077del] | [H558; Q1077] |
|---|---|---|---|---|
| | | Activation | | |
| $V_{1/2}$ (mV) | −40 ± 2 | −42 ± 1.2 | −44 ± 2 | −40 ± 2 |
| Slope factor | 5.5 ± 0.3 | 4.9 ± 0.1 | 5.1 ± 0.2 | 4.9 ± 0.3 |
| N | 5 | 22 | 23 | 13 |
| | | Inactivation | | |
| $V_{1/2}$ (mV) | −92 ± 2* | −85 ± 1.2 | −84 ± 1.3 | −85 ± 4 |
| N | 18 | 26 | 14 | 5 |

TABLE 3-continued

Voltage-dependent Kinetic Parameters for hNa$_v$1.5 Channels

|  | hH1 | [Q1077del] | [H558R; Q1077del] | [H558; Q1077] |
|---|---|---|---|---|
| Recovery | | | | |
| $\tau_f$(ms) | 3.0 ± 2 | 2.6 ± 0.3 | 2.8 ± 0.4 | 3.3 ± 1.6 |
| $\tau_s$(ms) | 81 ± 77 | 34 ± 4.7 | 53 ± 14 | 71 ± 40 |
| $A_s$ | 22 ± 0.1 | 22 ± 0.5 | 17 ± 2 | 26 ± 0.9 |
| N | 7 | 19 | 14 | 4 |
| Decay (−30 mV) | | | | |
| $\tau_f$(ms) | 1.8 ± 0.8 | 1.3 ± 0.4 | 1.6 ± 0.6 | 1.0 ± 0.2 |
| $\tau_s$(ms) | 11.4 ± 9.6 | 4.7 ± 3 | 8.1 ± 8.8 | 4.0 ± 2.0 |
| $A_f$ | 0.64 ± 0.3 | 0.56 ± 0.2 | 0.64 ± 0.2 | 0.7 ± 0.2 |
| N | 8 | 4 | 6 | 5 |
| Late I$_{Na}$ (−20 mV) | | | | |
| % of peak I$_{Na}$ | — | 0.85 ± 0.3 | 0.43 ± 0.2 | 0.85 ± 0.3 |
| N | — | 10 | 7 | 9 |

The data shown here are the mean ± SEM from curve fitting to N experiments.
Activation, inactivation, and recovery from inactivation parameters were obtained as in FIG. 3.
For the decay of I$_{Na}$ at −30 mV, the portion of the I$_{Na}$ trace after 90% of peak was fit a sum of exponentials: I$_{Na}$ (t) = 1 − (Af * exp − t/$\tau_f$ + A$_s$ * exp − t/$\tau_s$) + offset where t is time, $\tau_f$ and $\tau_s$ represent the time constant of the fast and slow components, and A$_f$ and A$_s$ are amplitudes of fast and slow component, respectively.
Late I$_{Na}$ was obtained at 720 ms after the depolarization as described previously (Valdivia, CR et al., J. Mol. Cell Cardiol. 34: 1029–1039, 2002).
Using one-way ANOVA with Bonferroni T-test, the midpoint of inactivation for hH1 marked by an asterisk was significantly negative to the variants lacking Q [H558R; Q1077del] and [Q1077del].

Figure 5:
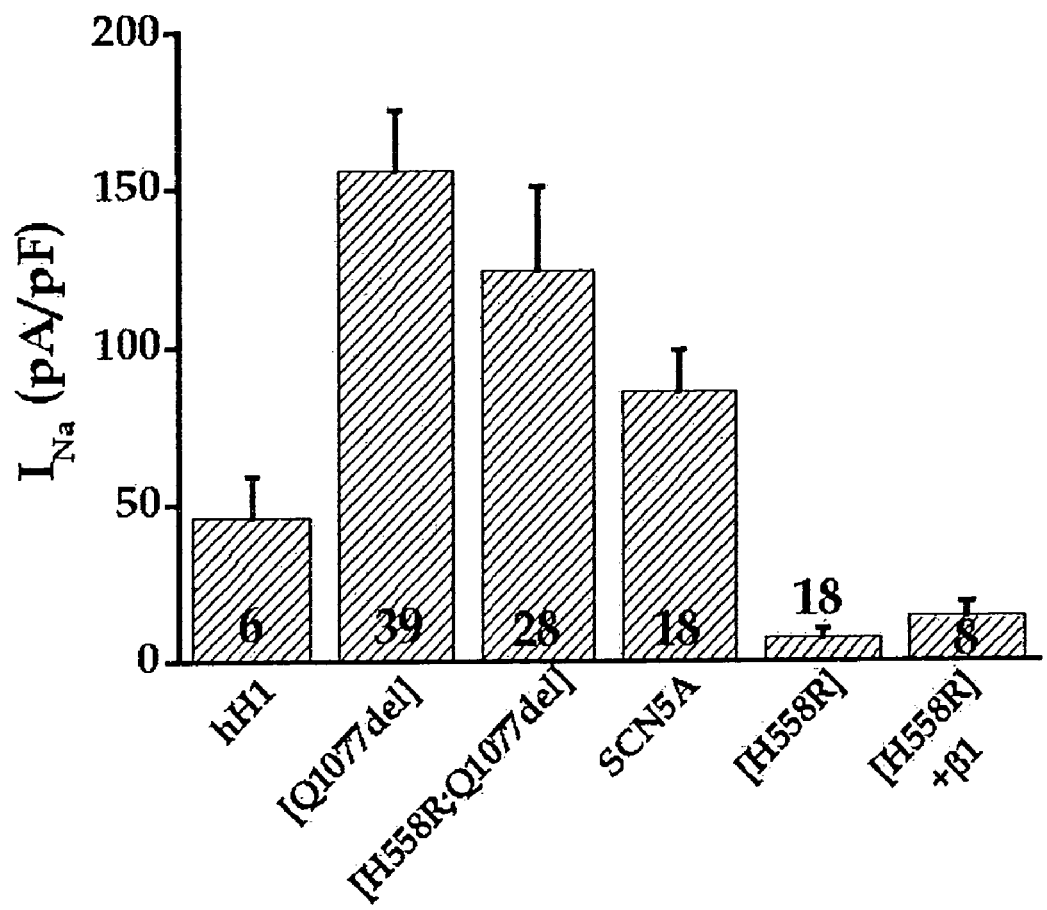
FIG. 5 shows summary data for peak $I_{Na}$ densities for the variants shown. Currents were elicited by a step depolarization to −20 mV from a holding potential of −140 mV and normalized to membrane capacitance. Data for the hH1 clone is included as an historical control. Results for [H558R] co-expressed with the β1 subunit are shown in the rightmost bar. The bars depict the mean and standard error of the mean derived from n measurements with the n for each construct shown within the bar. One way ANOVA (Deg. of freedom 124) with Bonferroni t-test was used to assess significance of differences in these amplitudes. By ANOVA, the $I_{Na}$ density for [H558R] was significantly lower (p<0.05) than [Q1077del] and [H558R;Q1077del] but not the Q1077 containing variants hH1 or [H558;Q1077].

The most dramatic finding was that [H558R] which contains Q1077 expressed very low current density. Data for current density are summarized in FIG. 5 where the current density for [H558R] was dramatically and significantly lower than the other variants. Other constructs that contained Q1077 (hH1 and [H558;Q1077]) also tended to have reduced currents but the difference did not reach statistical significance by ANOVA. RT-PCR of mRNA from cells with both transient and stable transfection of [H558R] showed abundant [H558R] transcript, but negligible currents. The #1 subunit increased current density when co-expressed with the α subunit of Nav1.5 (Nuss, H B et al., J. Gen. Physiol. 106: 1171-1191, 1995). The β1 subunit also "rescued" the trafficking defective SCN5A mutations (Valdivia, C R et al., Cardiovascular Research 54:624-629, 2002). When [H558R] was co-expressed with the β1 subunit, increased currents were observed although not at the levels of the other channel a subunits expressed alone (FIG. 5). To determine if the small currents seen with [H558R] could be endogenous currents, we voltage clamped untransfected HEK cells. In 8 cells, only 1 cell had 100 pA of current for an average density of less than 0.5 pA/pF compared with 2.8 pA/pF in [H558R] alone and 16 pA/pF in [H558R] co-transfected with the β1 subunit. We were unable to significantly increase endogenous currents in untransfected cells by co-transfection with β1 (1.0±0.5 pA/pF, n=9), incubation with mexiletine 100 μM for 24 hours (1.1±0.4 pA/pF, n=10), or incubation at 27° C. (0.9+0.4 pA/pF, n=8). We conclude that [H558R] did indeed generate small currents. When both variants [H558R] and [H558R; Q1077del] were co-expressed (plasmid DNA 0.75 μg each), normal current densities were seen. We conclude that variants containing Q1077 tended to have lower I$_{Na}$ density, and also tended to have the voltage-dependence of inactivation kinetics shifted in the negative direction. When the H558R polymorphism is expressed in the setting of the alternatively-spliced transcript that contains Q1077, then I$_{Na}$ density was dramatically reduced.

Figure 6:
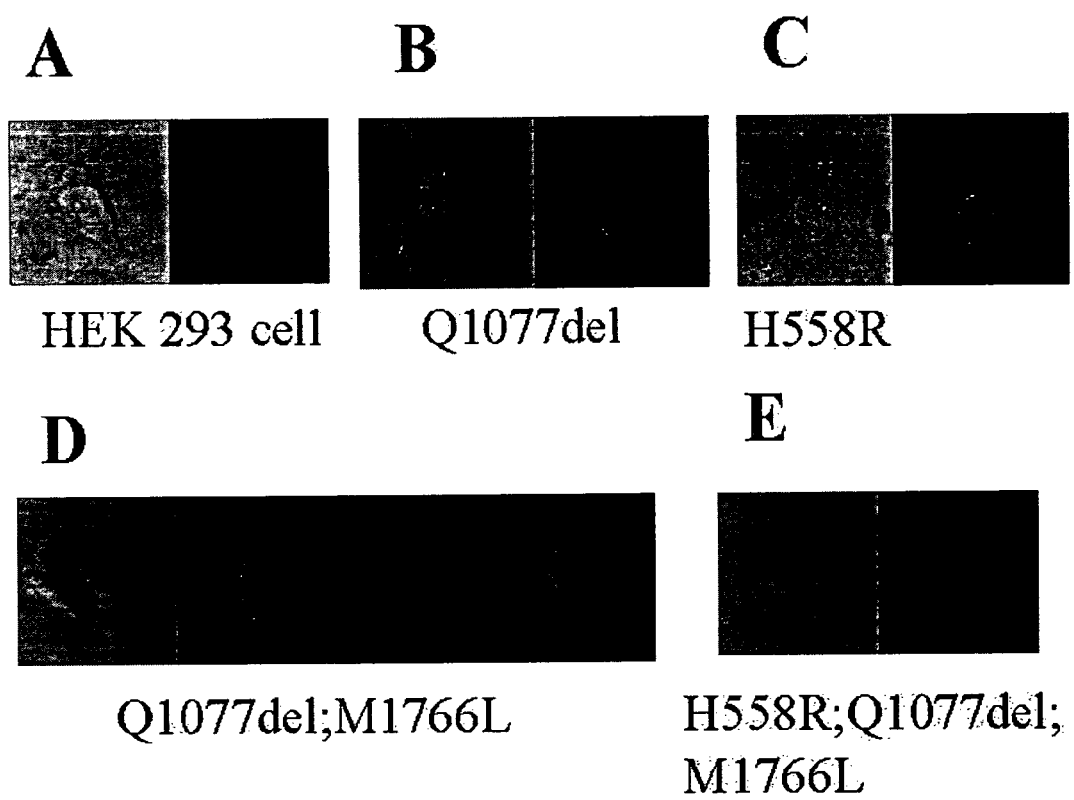
FIG. 6 shows that [H558R] has normal trafficking to the cell surface. Standard light photography in the left-most image of each panel is compared with confocal micrographs of human embryonic kidney (HEK) cells with immunostaining against a FLAG epitope inserted into the Na channel. (A) Non-transfected HEK-293 cell shows no immunostaining. (B) The [Q1077del] channel shows normal immunostaining pattern in the periphery and around the nucleus. (C) The [H558R] also shows normal staining pattern indicating that it trafficks to the cell surface. (D) With the mutation M1766L in the [Q1077del] the second image shows immunostaining is confined to a perinuclear location. The third image shows immunostaining with an endoplasmic reticulum marker (see Example below) and the fourth image (where the previous two images are superimposed) shows colocalization of the non-trafficking channel with the endoplasmic reticulum marker. (E) When the M1766L mutation was engineered into the [H558R;Q1077] background, normal trafficking to the cell periphery was seen. All results represented here were seen in at least 7 additional experiments.

Cell trafficking of the [H558] variant: Some SCN5A variants with decreased current density have been shown by immunocytochemistry to have defective trafficking (Ye, B. et al., Physiol. Genomics 12:187-193, 2003; Baroudi, G. et al., Circulation Research 90:E11-E16, 2002) and do not make it to the cell surface. To determine if [H558R] made it to the cell surface, we labeled the channel variants by inserting a FLAG epitope, and localized the channels by immunofluorescence and confocal microscopy. In each panel of FIG. 6 a light microscopy image is shown allowing for identification of the nucleus and the cell surface, followed by the confocal immunofluorescence image(s). A non-transfected cell gave no fluorescent signal as expected (FIG. 6A). The [Q 1077del] variant that gave robust current densities showed a rim of fluorescence at the cell surface as expected for a normally trafficking channel (FIG. 6B). The [H558R] variant expressed almost no current, but also showed fluorescence at the cell surface (FIG. 6C) suggesting that the lack of current was not caused by a trafficking defect.

As an example of a channel that is trafficking defective and as a positive non-trafficking control for our experiment with the [H558R] variant, we made the mutation M1766L in the variants and show data from two of these experiments (FIGS. 6D & E). We had previously shown M1766L to be trafficking defective in hH1a [T559A;Q1077del;M1766L] but to be normally trafficking in hH1b [H558R;L618I;Q1077del; M1766L] (Ye, B. et al., Physiol. Genomics 12:187-193, 2003). When the M1766L mutation was put into [Q1077del] to make [Q1077del;M1766L] (FIG. 6D), the fluorescence was restricted to the area around the nucleus without any labeling in the periphery, consistent with a trafficking defect. This eliminates the possibility that the rare variant T559A in hH1a was responsible for the trafficking defect as previously described (Ye, B. et al., Physiol. Genomics 12:187-193, 2003). An image with a marker for the endoplasmic reticulum is shown in the third panel of FIG. 6D, and the fourth image in FIG. 6D superimposes the second and third image to show co-localization of the channel with the endoplasmic reticulum marker. When M1766L was placed in the [H558R; Q1077del] background, the channel is rescued and makes it to the cell periphery (FIG. 6E), consistent with previous data and also showing that the rare variant L618I in hH1b was not responsible for "rescuing" the trafficking defect.

We claim

1. An isolated nucleic acid comprising a polynucleotide selected from the group consisting of a polynucleotide that encodes SEQ ID NO:8 or a polynucleotide fully complementary to a polynucleotide that encodes SEQ ID NO:8.

2. An isolated genetic construct comprising the polynucleotide of claim 1 operably linked to a non-native expression control sequence.

3. An isolated cell comprising a polynucleotide selected from the group consisting of a polynucleotide that encodes SEQ ID NO:8 or a polynucleotide fully complementary to a polynucleotide that encodes SEQ ID NO:8, wherein the polynucleotide is operably linked to a non-native expression control sequence.

4. The cell of claim 3, wherein the polynucleotide comprises nucleotides 1 to 6045 SEQ ID NO:7.

5. The cell of claim 3, wherein the cell is from a human embryonic kidney cell line.

6. The nucleic acid of claim 1, wherein the polynucleotide comprises nucleotides 1 to 6045 of SEQ ID NO:7.

* * * * *

SEQUENCE LISTING

<160> NUMBER OF SEQ ID NOS: 21

<210> SEQ ID NO 1
<211> LENGTH: 6172
<212> TYPE: DNA
<213> ORGANISM: Homo sapiens
<220> FEATURE:
<221> NAME/KEY: CDS
<222> LOCATION: (1)..(6048)

<400> SEQUENCE: 1

```
atg gca aac ttc cta tta cct agg ggc acc agc agc ttc cgc agg ttc      48
Met Ala Asn Phe Leu Leu Pro Arg Gly Thr Ser Ser Phe Arg Arg Phe
1               5                   10                  15 aca cgg gag tcc ctg gca gcc atc gag aag cgc atg gcg gag aag caa      96
Thr Arg Glu Ser Leu Ala Ala Ile Glu Lys Arg Met Ala Glu Lys Gln
            20                  25                  30 gcc cgc ggc tca acc acc ttg cag gag agc cga gag ggg ctg ccc gag     144
Ala Arg Gly Ser Thr Thr Leu Gln Glu Ser Arg Glu Gly Leu Pro Glu
        35                  40                  45 gag gag gct ccc cgg ccc cag ctg gac ctg cag gcc tcc aaa aag ctg     192
Glu Glu Ala Pro Arg Pro Gln Leu Asp Leu Gln Ala Ser Lys Lys Leu
    50                  55                  60 cca gat ctc tat ggc aat cca ccc caa gag ctc atc gga gag ccc ctg     240
Pro Asp Leu Tyr Gly Asn Pro Pro Gln Glu Leu Ile Gly Glu Pro Leu
65                  70                  75                  80 gag gac ctg gac ccc ttc tat agc acc caa aag act ttc atc gta ctg     288
Glu Asp Leu Asp Pro Phe Tyr Ser Thr Gln Lys Thr Phe Ile Val Leu
                85                  90                  95 aat aaa ggc aag acc atc ttc cgg ttc agt gcc acc aac gcc ttg tat     336
Asn Lys Gly Lys Thr Ile Phe Arg Phe Ser Ala Thr Asn Ala Leu Tyr
            100                 105                 110 gtc ctc agt ccc ttc cac ccc atc cgg aga gcg gct gtg aag att ctg     384
Val Leu Ser Pro Phe His Pro Ile Arg Arg Ala Ala Val Lys Ile Leu
        115                 120                 125 gtt cac tcg ctc ttc aac atg ctc atc atg tgc acc atc ctc acc aac     432
Val His Ser Leu Phe Asn Met Leu Ile Met Cys Thr Ile Leu Thr Asn
    130                 135                 140 tgc gtg ttc atg gcc cag cac gac cct cca ccc tgg acc aag tat gtc     480
Cys Val Phe Met Ala Gln His Asp Pro Pro Pro Trp Thr Lys Tyr Val
145                 150                 155                 160 gag tac acc ttc acc gcc att tac acc ttt gag tct ctg gtc aag att     528
Glu Tyr Thr Phe Thr Ala Ile Tyr Thr Phe Glu Ser Leu Val Lys Ile
                165                 170                 175 ctg gct cga ggc ttc tgc ctg cac gcg ttc act ttc ctt cgg gac cca     576
Leu Ala Arg Gly Phe Cys Leu His Ala Phe Thr Phe Leu Arg Asp Pro
            180                 185                 190 tgg aac tgg ctg gac ttt agt gtg att atc atg gca tac aca act gaa     624
Trp Asn Trp Leu Asp Phe Ser Val Ile Ile Met Ala Tyr Thr Thr Glu
        195                 200                 205 ttt gtg gac ctg ggc aat gtc tca gcc tta cgc acc ttc cga gtc ctc     672
Phe Val Asp Leu Gly Asn Val Ser Ala Leu Arg Thr Phe Arg Val Leu
    210                 215                 220 cgg gcc ctg aaa act ata tca gtc att tca ggg ctg aag acc atc gtg     720
Arg Ala Leu Lys Thr Ile Ser Val Ile Ser Gly Leu Lys Thr Ile Val
225                 230                 235                 240 ggg gcc ctg atc cag tct gtg aag aag ctg gct gat gtg atg gtc ctc     768
Gly Ala Leu Ile Gln Ser Val Lys Lys Leu Ala Asp Val Met Val Leu
                245                 250                 255
```

-continued

| | | |
|---|---|---|
| aca gtc ttc tgc ctc agc gtt ttt gcc ctc atc ggc ctg cag ctc ttc<br>Thr Val Phe Cys Leu Ser Val Phe Ala Leu Ile Gly Leu Gln Leu Phe<br>      260                          265                          270 | | 816 |
| atg ggc aac cta agg cac aag tgc gtg cgc aac ttc aca gcg ctc aac<br>Met Gly Asn Leu Arg His Lys Cys Val Arg Asn Phe Thr Ala Leu Asn<br>275                          280                          285 | | 864 |
| ggc acc aac ggc tcc gtg gag gcc gac ggc ttg gtc tgg gaa tcc ctg<br>Gly Thr Asn Gly Ser Val Glu Ala Asp Gly Leu Val Trp Glu Ser Leu<br>      290                          295                          300 | | 912 |
| gac ctt tac ctc agt gat cca gaa aat tac ctg ctc aag aac ggc acc<br>Asp Leu Tyr Leu Ser Asp Pro Glu Asn Tyr Leu Leu Lys Asn Gly Thr<br>305                          310                          315                          320 | | 960 |
| tct gat gtg tta ctg tgt ggg aac agc tct gac gct ggg aca tgt ccg<br>Ser Asp Val Leu Leu Cys Gly Asn Ser Ser Asp Ala Gly Thr Cys Pro<br>                        325                          330                          335 | | 1008 |
| gag ggc tac cgg tgc cta aag gca ggc gag aac ccc gac cac ggc tac<br>Glu Gly Tyr Arg Cys Leu Lys Ala Gly Glu Asn Pro Asp His Gly Tyr<br>                      340                        345                        350 | | 1056 |
| acc agc ttc gat tcc ttt gcc tgg gcc ttt ctt gca ctc ttc cgc ctg<br>Thr Ser Phe Asp Ser Phe Ala Trp Ala Phe Leu Ala Leu Phe Arg Leu<br>          355                        360                        365 | | 1104 |
| atg acg cag gac tgc tgg gag cgc ctc tat cag cag acc ctc agg tcc<br>Met Thr Gln Asp Cys Trp Glu Arg Leu Tyr Gln Gln Thr Leu Arg Ser<br>370                          375                          380 | | 1152 |
| gca ggg aag atc tac atg atc ttc ttc atg ctt gtc atc ttc ctg ggg<br>Ala Gly Lys Ile Tyr Met Ile Phe Phe Met Leu Val Ile Phe Leu Gly<br>385                          390                          395                          400 | | 1200 |
| tcc ttc tac ctg gtg aac ctg atc ctg gcc gtg gtc gca atg gcc tat<br>Ser Phe Tyr Leu Val Asn Leu Ile Leu Ala Val Val Ala Met Ala Tyr<br>                      405                        410                        415 | | 1248 |
| gag gag caa aac caa gcc acc atc gct gag acc gag gag aag gaa aag<br>Glu Glu Gln Asn Gln Ala Thr Ile Ala Glu Thr Glu Glu Lys Glu Lys<br>                    420                        425                        430 | | 1296 |
| cgc ttc cag gag gcc atg gaa atg ctc aag aaa gaa cac gag gcc ctc<br>Arg Phe Gln Glu Ala Met Glu Met Leu Lys Lys Glu His Glu Ala Leu<br>          435                        440                        445 | | 1344 |
| acc atc agg ggt gtg gat acc gtg tcc cgt agc tcc ttg gag atg tcc<br>Thr Ile Arg Gly Val Asp Thr Val Ser Arg Ser Ser Leu Glu Met Ser<br>450                          455                          460 | | 1392 |
| cct ttg gcc cca gta aac agc cat gag aga aga agc aag agg aga aaa<br>Pro Leu Ala Pro Val Asn Ser His Glu Arg Arg Ser Lys Arg Arg Lys<br>465                          470                        475                        480 | | 1440 |
| cgg atg tct tca gga act gag gag tgt ggg gag gac agg ctc ccc aag<br>Arg Met Ser Ser Gly Thr Glu Glu Cys Gly Glu Asp Arg Leu Pro Lys<br>                    485                        490                        495 | | 1488 |
| tct gac tca gaa gat ggt ccc aga gca atg aat cat ctc agc ctc acc<br>Ser Asp Ser Glu Asp Gly Pro Arg Ala Met Asn His Leu Ser Leu Thr<br>500                          505                        510 | | 1536 |
| cgt ggc ctc agc agg act tct atg aag cca cgt tcc agc cgc ggg agc<br>Arg Gly Leu Ser Arg Thr Ser Met Lys Pro Arg Ser Ser Arg Gly Ser<br>          515                        520                        525 | | 1584 |
| att ttc acc ttt cgc agg cga gac ctg ggt tct gaa gca gat ttt gca<br>Ile Phe Thr Phe Arg Arg Arg Asp Leu Gly Ser Glu Ala Asp Phe Ala<br>530                          535                        540 | | 1632 |
| gat gat gaa aac agc aca gcg ggg gag agc gag agc cac cac aca tca<br>Asp Asp Glu Asn Ser Thr Ala Gly Glu Ser Glu Ser His His Thr Ser<br>545                          550                        555                        560 | | 1680 |
| ctg ctg gtg ccc tgg ccc ctg cgc cgg acc agt gcc cag gga cag ccc<br>Leu Leu Val Pro Trp Pro Leu Arg Arg Thr Ser Ala Gln Gly Gln Pro<br>                    565                        570                        575 | | 1728 |

| | | |
|---|---|---|
| agt ccc gga acc tcg gct cct ggc cac gcc ctc cat ggc aaa aag aac<br>Ser Pro Gly Thr Ser Ala Pro Gly His Ala Leu His Gly Lys Lys Asn<br>580 585 590 | | 1776 |
| agc act gtg gac tgc aat ggg gtg gtc tca tta ctg ggg gca ggc gac<br>Ser Thr Val Asp Cys Asn Gly Val Val Ser Leu Leu Gly Ala Gly Asp<br>595 600 605 | | 1824 |
| cca gag gcc aca tcc cca gga agc cac ctc ctc cgc cct gtg atg cta<br>Pro Glu Ala Thr Ser Pro Gly Ser His Leu Leu Arg Pro Val Met Leu<br>610 615 620 | | 1872 |
| gag cac ccg cca gac acg acc acg cca tcg gag gag cca ggc ggg ccc<br>Glu His Pro Pro Asp Thr Thr Thr Pro Ser Glu Glu Pro Gly Gly Pro<br>625 630 635 640 | | 1920 |
| cag atg ctg acc tcc cag gct ccg tgt gta gat ggc ttc gag gag cca<br>Gln Met Leu Thr Ser Gln Ala Pro Cys Val Asp Gly Phe Glu Glu Pro<br>645 650 655 | | 1968 |
| gga gca cgg cag cgg gcc ctc agc gca gtc agc gtc ctc acc agc gca<br>Gly Ala Arg Gln Arg Ala Leu Ser Ala Val Ser Val Leu Thr Ser Ala<br>660 665 670 | | 2016 |
| ctg gaa gag tta gag gag tct cgc cac aag tgt cca cca tgc tgg aac<br>Leu Glu Glu Leu Glu Glu Ser Arg His Lys Cys Pro Pro Cys Trp Asn<br>675 680 685 | | 2064 |
| cgt ctc gcc cag cgc tac ctg atc tgg gag tgc tgc ccg ctg tgg atg<br>Arg Leu Ala Gln Arg Tyr Leu Ile Trp Glu Cys Cys Pro Leu Trp Met<br>690 695 700 | | 2112 |
| tcc atc aag cag gga gtg aag ttg gtg gtc atg gac ccg ttt act gac<br>Ser Ile Lys Gln Gly Val Lys Leu Val Val Met Asp Pro Phe Thr Asp<br>705 710 715 720 | | 2160 |
| ctc acc atc act atg tgc atc gta ctc aac aca ctc ttc atg gcg ctg<br>Leu Thr Ile Thr Met Cys Ile Val Leu Asn Thr Leu Phe Met Ala Leu<br>725 730 735 | | 2208 |
| gag cac tac aac atg aca agt gaa ttc gag gag atg ctg cag gtc gga<br>Glu His Tyr Asn Met Thr Ser Glu Phe Glu Glu Met Leu Gln Val Gly<br>740 745 750 | | 2256 |
| aac ctg gtc ttc aca ggg att ttc aca gca gag atg acc ttc aag atc<br>Asn Leu Val Phe Thr Gly Ile Phe Thr Ala Glu Met Thr Phe Lys Ile<br>755 760 765 | | 2304 |
| att gcc ctc gac ccc tac tac tac ttc caa cag ggc tgg aac atc ttc<br>Ile Ala Leu Asp Pro Tyr Tyr Tyr Phe Gln Gln Gly Trp Asn Ile Phe<br>770 775 780 | | 2352 |
| gac agc atc atc gtc atc ctt agc ctc atg gag ctg ggc ctg tcc cgc<br>Asp Ser Ile Ile Val Ile Leu Ser Leu Met Glu Leu Gly Leu Ser Arg<br>785 790 795 800 | | 2400 |
| atg agc aac ttg tcg gtg ctg cgc tcc ttc cgc ctg ctg cgg gtc ttc<br>Met Ser Asn Leu Ser Val Leu Arg Ser Phe Arg Leu Leu Arg Val Phe<br>805 810 815 | | 2448 |
| aag ctg gcc aaa tca tgg ccc acc ctg aac aca ctc atc aag atc atc<br>Lys Leu Ala Lys Ser Trp Pro Thr Leu Asn Thr Leu Ile Lys Ile Ile<br>820 825 830 | | 2496 |
| ggg aac tca gtg ggg gca ctg ggg aac ctg aca ctg gtg cta gcc atc<br>Gly Asn Ser Val Gly Ala Leu Gly Asn Leu Thr Leu Val Leu Ala Ile<br>835 840 845 | | 2544 |
| atc gtg ttc atc ttt gct gtg gtg ggc atg cag ctc ttt ggc aag aac<br>Ile Val Phe Ile Phe Ala Val Val Gly Met Gln Leu Phe Gly Lys Asn<br>850 855 860 | | 2592 |
| tac tcg gag ctg agg gac agc gac tca ggc ctg ctg cct cgc tgg cac<br>Tyr Ser Glu Leu Arg Asp Ser Asp Ser Gly Leu Leu Pro Arg Trp His<br>865 870 875 880 | | 2640 |
| atg atg gac ttc ttt cat gcc ttc ctc atc atc ttc cgc atc ctc tgt<br>Met Met Asp Phe Phe His Ala Phe Leu Ile Ile Phe Arg Ile Leu Cys | | 2688 |

-continued

|  |  |  |  |
|---|---|---|---|
| 885 | 890 | 895 | |
| gga gag tgg atc gag acc atg tgg gac tgc atg gag gtg tcg ggg cag<br>Gly Glu Trp Ile Glu Thr Met Trp Asp Cys Met Glu Val Ser Gly Gln<br>900 905 910 | | | 2736 |
| tca tta tgc ctg ctg gtc ttc ttg ctt gtt atg gtc att ggc aac ctt<br>Ser Leu Cys Leu Leu Val Phe Leu Leu Val Met Val Ile Gly Asn Leu<br>915 920 925 | | | 2784 |
| gtg gtc ctg aat ctc ttc ctg gcc ttg ctc agc tcc ttc agt gca<br>Val Val Leu Asn Leu Phe Leu Ala Leu Leu Ser Ser Phe Ser Ala<br>930 935 940 | | | 2832 |
| gac aac ctc aca gcc cct gat gag gac aga gag atg aac aac ctc cag<br>Asp Asn Leu Thr Ala Pro Asp Glu Asp Arg Glu Met Asn Asn Leu Gln<br>945 950 955 960 | | | 2880 |
| ctg gcc ctg gcc cgc atc cag agg ggc ctg cgc ttt gtc aag cgg acc<br>Leu Ala Leu Ala Arg Ile Gln Arg Gly Leu Arg Phe Val Lys Arg Thr<br>965 970 975 | | | 2928 |
| acc tgg gat ttc tgc tgt ggt ctc ctg cgg cag cgg cct cag aag ccc<br>Thr Trp Asp Phe Cys Cys Gly Leu Leu Arg Gln Arg Pro Gln Lys Pro<br>980 985 990 | | | 2976 |
| gca gcc ctt gcc gcc cag ggc cag ctg ccc agc tgc att gcc acc ccc<br>Ala Ala Leu Ala Ala Gln Gly Gln Leu Pro Ser Cys Ile Ala Thr Pro<br>995 1000 1005 | | | 3024 |
| tac tcc ccg cca ccc cca gag acg gag aag gtg cct ccc acc cgc<br>Tyr Ser Pro Pro Pro Pro Glu Thr Glu Lys Val Pro Pro Thr Arg<br>1010 1015 1020 | | | 3069 |
| aag gaa aca cgg ttt gag gaa ggc gag caa cca ggc cag ggc acc<br>Lys Glu Thr Arg Phe Glu Glu Gly Glu Gln Pro Gly Gln Gly Thr<br>1025 1030 1035 | | | 3114 |
| ccc ggg gat cca gag ccc gtg tgt gtg ccc atc gct gtg gcc gag<br>Pro Gly Asp Pro Glu Pro Val Cys Val Pro Ile Ala Val Ala Glu<br>1040 1045 1050 | | | 3159 |
| tca gac aca gat gac caa gaa gaa gat gag gag aac agc ctg ggc<br>Ser Asp Thr Asp Asp Gln Glu Glu Asp Glu Glu Asn Ser Leu Gly<br>1055 1060 1065 | | | 3204 |
| acg gag gag gag tcc agc aag cag cag gaa tcc cag cct gtg tcc<br>Thr Glu Glu Glu Ser Ser Lys Gln Gln Glu Ser Gln Pro Val Ser<br>1070 1075 1080 | | | 3249 |
| ggt ggc cca gag gcc cct ccg gat tcc agg acc tgg agc cag gtg<br>Gly Gly Pro Glu Ala Pro Pro Asp Ser Arg Thr Trp Ser Gln Val<br>1085 1090 1095 | | | 3294 |
| tca gcg act gcc tcc tct gag gcc gag gcc agt gca tct cag gcc<br>Ser Ala Thr Ala Ser Ser Glu Ala Glu Ala Ser Ala Ser Gln Ala<br>1100 1105 1110 | | | 3339 |
| gac tgg cgg cag cag tgg aaa gcg gaa ccc cag gcc cca ggg tgc<br>Asp Trp Arg Gln Gln Trp Lys Ala Glu Pro Gln Ala Pro Gly Cys<br>1115 1120 1125 | | | 3384 |
| ggt gag acc cca gag gac agt tgc tcc gag ggc agc aca gca gac<br>Gly Glu Thr Pro Glu Asp Ser Cys Ser Glu Gly Ser Thr Ala Asp<br>1130 1135 1140 | | | 3429 |
| atg acc aac acc gct gag ctc ctg gag cag atc cct gac ctc ggc<br>Met Thr Asn Thr Ala Glu Leu Leu Glu Gln Ile Pro Asp Leu Gly<br>1145 1150 1155 | | | 3474 |
| cag gat gtc aag gac cca gag gac tgc ttc act gaa ggc tgt gtc<br>Gln Asp Val Lys Asp Pro Glu Asp Cys Phe Thr Glu Gly Cys Val<br>1160 1165 1170 | | | 3519 |
| cgg cgc tgt ccc tgc tgt gcg gtg gac acc aca cag gcc cca ggg<br>Arg Arg Cys Pro Cys Cys Ala Val Asp Thr Thr Gln Ala Pro Gly<br>1175 1180 1185 | | | 3564 |
| aag gtc tgg tgg cgg ttg cgc aag acc tgc tac cac atc gtg gag<br> Lys Val Trp Trp Arg Leu Arg Lys Thr Cys Tyr His Ile Val Glu | | | 3609 |

|  |  |  |  |  |  |  |  |  |  |  |
|---|---|---|---|---|---|---|---|---|---|---|
| Lys | Val | Trp | Trp | Arg | Leu | Arg | Lys | Thr | Cys | Tyr | His | Ile | Val | Glu |
| 1190 |  |  |  |  | 1195 |  |  |  |  | 1200 |

```
cac agc tgg ttc gag aca ttc atc atc ttc atg atc cta ctc agc    3654
His Ser Trp Phe Glu Thr Phe Ile Ile Phe Met Ile Leu Leu Ser
1205                1210                1215 agt gga gcg ctg gcc ttc gag gac atc tac cta gag gag cgg aag    3699
Ser Gly Ala Leu Ala Phe Glu Asp Ile Tyr Leu Glu Glu Arg Lys
    1220                1225                1230 acc atc aag gtt ctg ctt gag tat gcc gac aag atg ttc aca tat    3744
Thr Ile Lys Val Leu Leu Glu Tyr Ala Asp Lys Met Phe Thr Tyr
1235                1240                1245 gtc ttc gtg ctg gag atg ctg ctc aag tgg gtg gcc tac ggc ttc    3789
Val Phe Val Leu Glu Met Leu Leu Lys Trp Val Ala Tyr Gly Phe
    1250                1255                1260 aag aag tac ttc acc aat gcc tgg tgc tgg ctc gac ttc ctc atc    3834
Lys Lys Tyr Phe Thr Asn Ala Trp Cys Trp Leu Asp Phe Leu Ile
1265                1270                1275 gta gac gtc tct ctg gtc agc ctg gtg gcc aac acc ctg ggc ttt    3879
Val Asp Val Ser Leu Val Ser Leu Val Ala Asn Thr Leu Gly Phe
    1280                1285                1290 gcc gag atg ggt ccc atc aag tca ctg cgg acg ctg cgt gca ctc    3924
Ala Glu Met Gly Pro Ile Lys Ser Leu Arg Thr Leu Arg Ala Leu
1295                1300                1305 cgt cct ctg aga gct ctg tca cga ttt gag ggc atg agg gtg gtg    3969
Arg Pro Leu Arg Ala Leu Ser Arg Phe Glu Gly Met Arg Val Val
    1310                1315                1320 gtc aat gcc ctg gtg ggc gcc atc ccg tcc atc atg aac gtc ctc    4014
Val Asn Ala Leu Val Gly Ala Ile Pro Ser Ile Met Asn Val Leu
1325                1330                1335 ctc gtc tgc ctc atc ttc tgg ctc atc ttc agc atc atg ggc gtg    4059
Leu Val Cys Leu Ile Phe Trp Leu Ile Phe Ser Ile Met Gly Val
    1340                1345                1350 aac ctc ttt gcg ggg aag ttt ggg agg tgc atc aac cag aca gag    4104
Asn Leu Phe Ala Gly Lys Phe Gly Arg Cys Ile Asn Gln Thr Glu
1355                1360                1365 gga gac ttg cct ttg aac tac acc atc gtg aac aac aag agc cag    4149
Gly Asp Leu Pro Leu Asn Tyr Thr Ile Val Asn Asn Lys Ser Gln
    1370                1375                1380 tgt gag tcc ttg aac ttg acc gga gaa ttg tac tgg acc aag gtg    4194
Cys Glu Ser Leu Asn Leu Thr Gly Glu Leu Tyr Trp Thr Lys Val
1385                1390                1395 aaa gtc aac ttt gac aac gtg ggg gcc ggg tac ctg gcc ctt ctg    4239
Lys Val Asn Phe Asp Asn Val Gly Ala Gly Tyr Leu Ala Leu Leu
    1400                1405                1410 cag gtg gca aca ttt aaa ggc tgg atg gac att atg tat gca gct    4284
Gln Val Ala Thr Phe Lys Gly Trp Met Asp Ile Met Tyr Ala Ala
1415                1420                1425 gtg gac tcc agg ggg tat gaa gag cag cct cag tgg gaa tac aac    4329
Val Asp Ser Arg Gly Tyr Glu Glu Gln Pro Gln Trp Glu Tyr Asn
    1430                1435                1440 ctc tac atg tac atc tat ttt gtc att ttc atc atc ttt ggg tct    4374
Leu Tyr Met Tyr Ile Tyr Phe Val Ile Phe Ile Ile Phe Gly Ser
1445                1450                1455 ttc ttc acc ctg aac ctc ttt att ggt gtc atc att gac aac ttc    4419
Phe Phe Thr Leu Asn Leu Phe Ile Gly Val Ile Ile Asp Asn Phe
    1460                1465                1470 aac caa cag aag aaa aag tta ggg ggc cag gac atc ttc atg aca    4464
Asn Gln Gln Lys Lys Lys Leu Gly Gly Gln Asp Ile Phe Met Thr
1475                1480                1485
```

```
                                                         -continued
gag gag cag aag aag tac tac aat gcc atg aag aag ctg ggc tcc    4509
Glu Glu Gln Lys Lys Tyr Tyr Asn Ala Met Lys Lys Leu Gly Ser
    1490            1495                1500 aag aag ccc cag aag ccc atc cca cgg ccc ctg aac aag tac cag    4554
Lys Lys Pro Gln Lys Pro Ile Pro Arg Pro Leu Asn Lys Tyr Gln
    1505            1510                1515 ggc ttc ata ttc gac att gtg acc aag cag gcc ttt gac gtc acc    4599
Gly Phe Ile Phe Asp Ile Val Thr Lys Gln Ala Phe Asp Val Thr
    1520            1525                1530 atc atg ttt ctg atc tgc ttg aat atg gtg acc atg atg gtg gag    4644
Ile Met Phe Leu Ile Cys Leu Asn Met Val Thr Met Met Val Glu
    1535            1540                1545 aca gat gac caa agt cct gag aaa atc aac atc ttg gcc aag atc    4689
Thr Asp Asp Gln Ser Pro Glu Lys Ile Asn Ile Leu Ala Lys Ile
    1550            1555                1560 aac ctg ctc ttt gtg gcc atc ttc aca ggc gag tgt att gtc aag    4734
Asn Leu Leu Phe Val Ala Ile Phe Thr Gly Glu Cys Ile Val Lys
    1565            1570                1575 ctg gct gcc ctg cgc cac tac tac ttc acc aac agc tgg aat atc    4779
Leu Ala Ala Leu Arg His Tyr Tyr Phe Thr Asn Ser Trp Asn Ile
    1580            1585                1590 ttc gac ttc gtg gtt gtc atc ctc tcc atc gtg ggc act gtg ctc    4824
Phe Asp Phe Val Val Val Ile Leu Ser Ile Val Gly Thr Val Leu
    1595            1600                1605 tcg gac atc atc cag aag tac ttc ttc tcc ccg acg ctc ttc cga    4869
Ser Asp Ile Ile Gln Lys Tyr Phe Phe Ser Pro Thr Leu Phe Arg
    1610            1615                1620 gtc atc cgc ctg gcc cga ata ggc cgc atc ctc aga ctg atc cga    4914
Val Ile Arg Leu Ala Arg Ile Gly Arg Ile Leu Arg Leu Ile Arg
    1625            1630                1635 ggg gcc aag ggg atc cgc acg ctg ctc ttt gcc ctc atg atg tcc    4959
Gly Ala Lys Gly Ile Arg Thr Leu Leu Phe Ala Leu Met Met Ser
    1640            1645                1650 ctg cct gcc ctc ttc aac atc ggg ctg ctc ttc ctc gtc atg        5004
Leu Pro Ala Leu Phe Asn Ile Gly Leu Leu Leu Phe Leu Val Met
    1655            1660                1665 ttc atc tac tcc atc ttt ggc atg gcc aac ttc gct tat gtc aag    5049
Phe Ile Tyr Ser Ile Phe Gly Met Ala Asn Phe Ala Tyr Val Lys
    1670            1675                1680 tgg gag gct ggc atc gac gac atg ttc aac ttc cag acc ttc gcc    5094
Trp Glu Ala Gly Ile Asp Asp Met Phe Asn Phe Gln Thr Phe Ala
    1685            1690                1695 aac agc atg ctg tgc ctc ttc cag atc acc acg tcg gcc ggc tgg    5139
Asn Ser Met Leu Cys Leu Phe Gln Ile Thr Thr Ser Ala Gly Trp
    1700            1705                1710 gat ggc ctc ctc agc ccc atc ctc aac act ggg ccg ccc tac tgc    5184
Asp Gly Leu Leu Ser Pro Ile Leu Asn Thr Gly Pro Pro Tyr Cys
    1715            1720                1725 gac ccc act ctg ccc aac agc aat ggc tct cgg ggg gac tgc ggg    5229
Asp Pro Thr Leu Pro Asn Ser Asn Gly Ser Arg Gly Asp Cys Gly
    1730            1735                1740 agc cca gcc gtg ggc atc ctc ttc ttc acc acc tac atc atc atc    5274
Ser Pro Ala Val Gly Ile Leu Phe Phe Thr Thr Tyr Ile Ile Ile
    1745            1750                1755 tcc ttc ctc atc gtg gtc aac atg tac att gcc atc atc ctg gag    5319
Ser Phe Leu Ile Val Val Asn Met Tyr Ile Ala Ile Ile Leu Glu
    1760            1765                1770 aac ttc agc gtg gcc acg gag gag agc acc gag ccc ctg agt gag    5364
Asn Phe Ser Val Ala Thr Glu Glu Ser Thr Glu Pro Leu Ser Glu
    1775            1780                1785
```

| | | | | | | | | | | | | | | | |
|---|---|---|---|---|---|---|---|---|---|---|---|---|---|---|---|
| gac | gac | ttc | gat | atg | ttc | tat | gag | atc | tgg | gag | aaa | ttt | gac | cca | 5409 |
| Asp | Asp | Phe | Asp | Met | Phe | Tyr | Glu | Ile | Trp | Glu | Lys | Phe | Asp | Pro | |
| | 1790 | | | | 1795 | | | | | 1800 | | | | | |
| gag | gcc | act | cag | ttt | att | gag | tat | tcg | gtc | ctg | tct | gac | ttt | gcc | 5454 |
| Glu | Ala | Thr | Gln | Phe | Ile | Glu | Tyr | Ser | Val | Leu | Ser | Asp | Phe | Ala | |
| | 1805 | | | | 1810 | | | | | 1815 | | | | | |
| gat | gcc | ctg | tct | gag | cca | ctc | cgt | atc | gcc | aag | ccc | aac | cag | ata | 5499 |
| Asp | Ala | Leu | Ser | Glu | Pro | Leu | Arg | Ile | Ala | Lys | Pro | Asn | Gln | Ile | |
| | 1820 | | | | 1825 | | | | | 1830 | | | | | |
| agc | ctc | atc | aac | atg | gac | ctg | ccc | atg | gtg | agt | ggg | gac | cgc | atc | 5544 |
| Ser | Leu | Ile | Asn | Met | Asp | Leu | Pro | Met | Val | Ser | Gly | Asp | Arg | Ile | |
| | 1835 | | | | 1840 | | | | | 1845 | | | | | |
| cat | tgc | atg | gac | att | ctc | ttt | gcc | ttc | acc | aaa | agg | gtc | ctg | ggg | 5589 |
| His | Cys | Met | Asp | Ile | Leu | Phe | Ala | Phe | Thr | Lys | Arg | Val | Leu | Gly | |
| | 1850 | | | | 1855 | | | | | 1860 | | | | | |
| gag | tct | ggg | gag | atg | gac | gcc | ctg | aag | atc | cag | atg | gag | gag | aag | 5634 |
| Glu | Ser | Gly | Glu | Met | Asp | Ala | Leu | Lys | Ile | Gln | Met | Glu | Glu | Lys | |
| | 1865 | | | | 1870 | | | | | 1875 | | | | | |
| ttc | atg | gca | gcc | aac | cca | tcc | aag | atc | tcc | tac | gag | ccc | atc | acc | 5679 |
| Phe | Met | Ala | Ala | Asn | Pro | Ser | Lys | Ile | Ser | Tyr | Glu | Pro | Ile | Thr | |
| | 1880 | | | | 1885 | | | | | 1890 | | | | | |
| acc | aca | ctc | cgg | cgc | aag | cac | gaa | gag | gtg | tcg | gcc | atg | gtt | atc | 5724 |
| Thr | Thr | Leu | Arg | Arg | Lys | His | Glu | Glu | Val | Ser | Ala | Met | Val | Ile | |
| | 1895 | | | | 1900 | | | | | 1905 | | | | | |
| cag | aga | gcc | ttc | cgc | agg | cac | ctg | ctg | caa | cgc | tct | ttg | aag | cat | 5769 |
| Gln | Arg | Ala | Phe | Arg | Arg | His | Leu | Leu | Gln | Arg | Ser | Leu | Lys | His | |
| | 1910 | | | | 1915 | | | | | 1920 | | | | | |
| gcc | tcc | ttc | ctc | ttc | cgt | cag | cag | gcg | ggc | agc | ggc | ctc | tcc | gaa | 5814 |
| Ala | Ser | Phe | Leu | Phe | Arg | Gln | Gln | Ala | Gly | Ser | Gly | Leu | Ser | Glu | |
| | 1925 | | | | 1930 | | | | | 1935 | | | | | |
| gag | gat | gcc | cct | gag | cga | gag | ggc | ctc | atc | gcc | tac | gtg | atg | agt | 5859 |
| Glu | Asp | Ala | Pro | Glu | Arg | Glu | Gly | Leu | Ile | Ala | Tyr | Val | Met | Ser | |
| | 1940 | | | | 1945 | | | | | 1950 | | | | | |
| gag | aac | ttc | tcc | cga | ccc | ctt | ggc | cca | ccc | tcc | agc | tcc | tcc | atc | 5904 |
| Glu | Asn | Phe | Ser | Arg | Pro | Leu | Gly | Pro | Pro | Ser | Ser | Ser | Ser | Ile | |
| | 1955 | | | | 1960 | | | | | 1965 | | | | | |
| tcc | tcc | act | tcc | ttc | cca | ccc | tcc | tat | gac | agt | gtc | act | aga | gcc | 5949 |
| Ser | Ser | Thr | Ser | Phe | Pro | Pro | Ser | Tyr | Asp | Ser | Val | Thr | Arg | Ala | |
| | 1970 | | | | 1975 | | | | | 1980 | | | | | |
| acc | agc | gat | aac | ctc | cag | gtg | cgg | ggg | tct | gac | tac | agc | cac | agt | 5994 |
| Thr | Ser | Asp | Asn | Leu | Gln | Val | Arg | Gly | Ser | Asp | Tyr | Ser | His | Ser | |
| | 1985 | | | | 1990 | | | | | 1995 | | | | | |
| gaa | gat | ctc | gcc | gac | ttc | ccc | cct | tct | ccg | gac | agg | gac | cgt | gag | 6039 |
| Glu | Asp | Leu | Ala | Asp | Phe | Pro | Pro | Ser | Pro | Asp | Arg | Asp | Arg | Glu | |
| | 2000 | | | | 2005 | | | | | 2010 | | | | | |
| tcc | atc | gtg | tgagcctcgg cctggctggc caggacacac tgaaaagcag | | | | | | | | | | | | 6088 |
| Ser | Ile | Val | | | | | | | | | | | | | |
| | 2015 | | | | | | | | | | | | | | | ccttttcac catggcaaac ctaaatgcag tcagtcamaa accagcctgg ggccttcctg  6148 gctttgggag taagaaatgg gcct  6172

<210> SEQ ID NO 2
<211> LENGTH: 2016
<212> TYPE: PRT
<213> ORGANISM: Homo sapiens

<400> SEQUENCE: 2

Met Ala Asn Phe Leu Leu Pro Arg Gly Thr Ser Ser Phe Arg Arg Phe
1               5                   10                  15

-continued

```
Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
            35                  40                  45

Glu Glu Ala Pro Arg Pro Gln Leu Asp Leu Gln Ala Ser Lys Lys Leu
        50                  55                  60

Pro Asp Leu Tyr Gly Asn Pro Pro Gln Glu Leu Ile Gly Glu Pro Leu
 65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
            115                 120                 125

Val His Ser Leu Phe Asn Met Leu Ile Met Cys Thr Ile Leu Thr Asn
            130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
            165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
            195                 200                 205

Phe Val Asp Leu Gly Asn Val Ser Ala Leu Arg Thr Phe Arg Val Leu
        210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
            245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
            275                 280                 285

Gly Thr Asn Gly Ser Val Glu Ala Asp Gly Leu Val Trp Glu Ser Leu
        290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
            325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
            355                 360                 365

Met Thr Gln Asp Cys Trp Glu Arg Leu Tyr Gln Gln Thr Leu Arg Ser
        370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
            405                 410                 415

Glu Glu Gln Asn Gln Ala Thr Ile Ala Glu Thr Glu Glu Lys Glu Lys
            420                 425                 430
```

```
Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
        450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
                500                 505                 510

Arg Gly Leu Ser Arg Thr Ser Met Lys Pro Arg Ser Arg Ser Gly Ser
        515                 520                 525

Ile Phe Thr Phe Arg Arg Arg Asp Leu Gly Ser Glu Ala Asp Phe Ala
        530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
        610                 615                 620

Glu His Pro Pro Asp Thr Thr Thr Pro Ser Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
                660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
        690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
        770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
```

-continued

```
                850                 855                 860
Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
                900                 905                 910

Ser Leu Cys Leu Leu Val Phe Leu Leu Val Met Val Ile Gly Asn Leu
                915                 920                 925

Val Val Leu Asn Leu Phe Leu Ala Leu Leu Leu Ser Ser Phe Ser Ala
930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
                980                 985                 990

Ala Ala Leu Ala Ala Gln Gly Gln Leu Pro Ser Cys Ile Ala Thr Pro
                995                 1000                1005

Tyr Ser Pro Pro Pro Pro Glu Thr Glu Lys Val Pro Pro Thr Arg
    1010                1015                1020

Lys Glu Thr Arg Phe Glu Glu Gly Glu Gln Pro Gly Gln Gly Thr
    1025                1030                1035

Pro Gly Asp Pro Glu Pro Val Cys Val Pro Ile Ala Val Ala Glu
    1040                1045                1050

Ser Asp Thr Asp Asp Gln Glu Asp Glu Glu Asn Ser Leu Gly
    1055                1060                1065

Thr Glu Glu Glu Ser Ser Lys Gln Gln Glu Ser Gln Pro Val Ser
    1070                1075                1080

Gly Gly Pro Glu Ala Pro Pro Asp Ser Arg Thr Trp Ser Gln Val
    1085                1090                1095

Ser Ala Thr Ala Ser Ser Glu Ala Glu Ala Ser Ala Ser Gln Ala
    1100                1105                1110

Asp Trp Arg Gln Gln Trp Lys Ala Glu Pro Gln Ala Pro Gly Cys
    1115                1120                1125

Gly Glu Thr Pro Glu Asp Ser Cys Ser Glu Gly Ser Thr Ala Asp
    1130                1135                1140

Met Thr Asn Thr Ala Glu Leu Leu Glu Gln Ile Pro Asp Leu Gly
    1145                1150                1155

Gln Asp Val Lys Asp Pro Glu Asp Cys Phe Thr Glu Gly Cys Val
    1160                1165                1170

Arg Arg Cys Pro Cys Cys Ala Val Asp Thr Thr Gln Ala Pro Gly
    1175                1180                1185

Lys Val Trp Trp Arg Leu Arg Lys Thr Cys Tyr His Ile Val Glu
    1190                1195                1200

His Ser Trp Phe Glu Thr Phe Ile Ile Phe Met Ile Leu Leu Ser
    1205                1210                1215

Ser Gly Ala Leu Ala Phe Glu Asp Ile Tyr Leu Glu Glu Arg Lys
    1220                1225                1230

Thr Ile Lys Val Leu Leu Glu Tyr Ala Asp Lys Met Phe Thr Tyr
    1235                1240                1245

Val Phe Val Leu Glu Met Leu Leu Lys Trp Val Ala Tyr Gly Phe
    1250                1255                1260
```

```
Lys Lys Tyr Phe Thr Asn Ala Trp Cys Trp Leu Asp Phe Leu Ile
1265                1270                1275

Val Asp Val Ser Leu Val Ser Leu Val Ala Asn Thr Leu Gly Phe
1280                1285                1290

Ala Glu Met Gly Pro Ile Lys Ser Leu Arg Thr Leu Arg Ala Leu
1295                1300                1305

Arg Pro Leu Arg Ala Leu Ser Arg Phe Glu Gly Met Arg Val Val
1310                1315                1320

Val Asn Ala Leu Val Gly Ala Ile Pro Ser Ile Met Asn Val Leu
1325                1330                1335

Leu Val Cys Leu Ile Phe Trp Leu Ile Phe Ser Ile Met Gly Val
1340                1345                1350

Asn Leu Phe Ala Gly Lys Phe Gly Arg Cys Ile Asn Gln Thr Glu
1355                1360                1365

Gly Asp Leu Pro Leu Asn Tyr Thr Ile Val Asn Asn Lys Ser Gln
1370                1375                1380

Cys Glu Ser Leu Asn Leu Thr Gly Glu Leu Tyr Trp Thr Lys Val
1385                1390                1395

Lys Val Asn Phe Asp Asn Val Gly Ala Gly Tyr Leu Ala Leu Leu
1400                1405                1410

Gln Val Ala Thr Phe Lys Gly Trp Met Asp Ile Met Tyr Ala Ala
1415                1420                1425

Val Asp Ser Arg Gly Tyr Glu Glu Gln Pro Gln Trp Glu Tyr Asn
1430                1435                1440

Leu Tyr Met Tyr Ile Tyr Phe Val Ile Phe Ile Ile Phe Gly Ser
1445                1450                1455

Phe Phe Thr Leu Asn Leu Phe Ile Gly Val Ile Ile Asp Asn Phe
1460                1465                1470

Asn Gln Gln Lys Lys Lys Leu Gly Gly Gln Asp Ile Phe Met Thr
1475                1480                1485

Glu Glu Gln Lys Lys Tyr Tyr Asn Ala Met Lys Lys Leu Gly Ser
1490                1495                1500

Lys Lys Pro Gln Lys Pro Ile Pro Arg Pro Leu Asn Lys Tyr Gln
1505                1510                1515

Gly Phe Ile Phe Asp Ile Val Thr Lys Gln Ala Phe Asp Val Thr
1520                1525                1530

Ile Met Phe Leu Ile Cys Leu Asn Met Val Thr Met Met Val Glu
1535                1540                1545

Thr Asp Asp Gln Ser Pro Glu Lys Ile Asn Ile Leu Ala Lys Ile
1550                1555                1560

Asn Leu Leu Phe Val Ala Ile Phe Thr Gly Glu Cys Ile Val Lys
1565                1570                1575

Leu Ala Ala Leu Arg His Tyr Tyr Phe Thr Asn Ser Trp Asn Ile
1580                1585                1590

Phe Asp Phe Val Val Val Ile Leu Ser Ile Val Gly Thr Val Leu
1595                1600                1605

Ser Asp Ile Ile Gln Lys Tyr Phe Phe Ser Pro Thr Leu Phe Arg
1610                1615                1620

Val Ile Arg Leu Ala Arg Ile Gly Arg Ile Leu Arg Leu Ile Arg
1625                1630                1635

Gly Ala Lys Gly Ile Arg Thr Leu Leu Phe Ala Leu Met Met Ser
1640                1645                1650
```

```
Leu Pro Ala Leu Phe Asn Ile Gly Leu Leu Phe Leu Val Met
1655                1660                1665

Phe Ile Tyr Ser Ile Phe Gly Met Ala Asn Phe Ala Tyr Val Lys
1670                1675                1680

Trp Glu Ala Gly Ile Asp Asp Met Phe Asn Phe Gln Thr Phe Ala
1685                1690                1695

Asn Ser Met Leu Cys Leu Phe Gln Ile Thr Thr Ser Ala Gly Trp
1700                1705                1710

Asp Gly Leu Leu Ser Pro Ile Leu Asn Thr Gly Pro Pro Tyr Cys
1715                1720                1725

Asp Pro Thr Leu Pro Asn Ser Asn Gly Ser Arg Gly Asp Cys Gly
1730                1735                1740

Ser Pro Ala Val Gly Ile Leu Phe Phe Thr Thr Tyr Ile Ile Ile
1745                1750                1755

Ser Phe Leu Ile Val Val Asn Met Tyr Ile Ala Ile Ile Leu Glu
1760                1765                1770

Asn Phe Ser Val Ala Thr Glu Glu Ser Thr Glu Pro Leu Ser Glu
1775                1780                1785

Asp Asp Phe Asp Met Phe Tyr Glu Ile Trp Glu Lys Phe Asp Pro
1790                1795                1800

Glu Ala Thr Gln Phe Ile Glu Tyr Ser Val Leu Ser Asp Phe Ala
1805                1810                1815

Asp Ala Leu Ser Glu Pro Leu Arg Ile Ala Lys Pro Asn Gln Ile
1820                1825                1830

Ser Leu Ile Asn Met Asp Leu Pro Met Val Ser Gly Asp Arg Ile
1835                1840                1845

His Cys Met Asp Ile Leu Phe Ala Phe Thr Lys Arg Val Leu Gly
1850                1855                1860

Glu Ser Gly Glu Met Asp Ala Leu Lys Ile Gln Met Glu Glu Lys
1865                1870                1875

Phe Met Ala Ala Asn Pro Ser Lys Ile Ser Tyr Glu Pro Ile Thr
1880                1885                1890

Thr Thr Leu Arg Arg Lys His Glu Glu Val Ser Ala Met Val Ile
1895                1900                1905

Gln Arg Ala Phe Arg Arg His Leu Leu Gln Arg Ser Leu Lys His
1910                1915                1920

Ala Ser Phe Leu Phe Arg Gln Gln Ala Gly Ser Gly Leu Ser Glu
1925                1930                1935

Glu Asp Ala Pro Glu Arg Glu Gly Leu Ile Ala Tyr Val Met Ser
1940                1945                1950

Glu Asn Phe Ser Arg Pro Leu Gly Pro Pro Ser Ser Ser Ser Ile
1955                1960                1965

Ser Ser Thr Ser Phe Pro Pro Ser Tyr Asp Ser Val Thr Arg Ala
1970                1975                1980

Thr Ser Asp Asn Leu Gln Val Arg Gly Ser Asp Tyr Ser His Ser
1985                1990                1995

Glu Asp Leu Ala Asp Phe Pro Pro Ser Pro Asp Arg Asp Arg Glu
2000                2005                2010

Ser Ile Val
2015

<210> SEQ ID NO 3
<211> LENGTH: 6172
<212> TYPE: DNA
```

```
<213> ORGANISM: Homo sapiens
<220> FEATURE:
<221> NAME/KEY: CDS
<222> LOCATION: (1)..(6048)

<400> SEQUENCE: 3 atg gca aac ttc cta tta cct agg ggc acc agc agc ttc cgc agg ttc      48
Met Ala Asn Phe Leu Leu Pro Arg Gly Thr Ser Ser Phe Arg Arg Phe
1               5                   10                  15 aca cgg gag tcc ctg gca gcc atc gag aag cgc atg gcg gag aag caa      96
Thr Arg Glu Ser Leu Ala Ala Ile Glu Lys Arg Met Ala Glu Lys Gln
            20                  25                  30 gcc cgc ggc tca acc acc ttg cag gag agc cga gag ggg ctg ccc gag     144
Ala Arg Gly Ser Thr Thr Leu Gln Glu Ser Arg Glu Gly Leu Pro Glu
        35                  40                  45 gag gag gct ccc cgg ccc cag ctg gac ctg cag gcc tcc aaa aag ctg     192
Glu Glu Ala Pro Arg Pro Gln Leu Asp Leu Gln Ala Ser Lys Lys Leu
    50                  55                  60 cca gat ctc tat ggc aat cca ccc caa gag ctc atc gga gag ccc ctg     240
Pro Asp Leu Tyr Gly Asn Pro Pro Gln Glu Leu Ile Gly Glu Pro Leu
65                  70                  75                  80 gag gac ctg gac ccc ttc tat agc acc caa aag act ttc atc gta ctg     288
Glu Asp Leu Asp Pro Phe Tyr Ser Thr Gln Lys Thr Phe Ile Val Leu
                85                  90                  95 aat aaa ggc aag acc atc ttc cgg ttc agt gcc acc aac gcc ttg tat     336
Asn Lys Gly Lys Thr Ile Phe Arg Phe Ser Ala Thr Asn Ala Leu Tyr
            100                 105                 110 gtc ctc agt ccc ttc cac ccc atc cgg aga gcg gct gtg aag att ctg     384
Val Leu Ser Pro Phe His Pro Ile Arg Arg Ala Ala Val Lys Ile Leu
        115                 120                 125 gtt cac tcg ctc ttc aac atg ctc atc atg tgc acc atc ctc acc aac     432
Val His Ser Leu Phe Asn Met Leu Ile Met Cys Thr Ile Leu Thr Asn
    130                 135                 140 tgc gtg ttc atg gcc cag cac gac cct cca ccc tgg acc aag tat gtc     480
Cys Val Phe Met Ala Gln His Asp Pro Pro Pro Trp Thr Lys Tyr Val
145                 150                 155                 160 gag tac acc ttc acc gcc att tac acc ttt gag tct ctg gtc aag att     528
Glu Tyr Thr Phe Thr Ala Ile Tyr Thr Phe Glu Ser Leu Val Lys Ile
                165                 170                 175 ctg gct cga ggc ttc tgc ctg cac gcg ttc act ttc ctt cgg gac cca     576
Leu Ala Arg Gly Phe Cys Leu His Ala Phe Thr Phe Leu Arg Asp Pro
            180                 185                 190 tgg aac tgg ctg gac ttt agt gtg att atc atg gca tac aca act gaa     624
Trp Asn Trp Leu Asp Phe Ser Val Ile Ile Met Ala Tyr Thr Thr Glu
        195                 200                 205 ttt gtg gac ctg ggc aat gtc tca gcc tta cgc acc ttc cga gtc ctc     672
Phe Val Asp Leu Gly Asn Val Ser Ala Leu Arg Thr Phe Arg Val Leu
    210                 215                 220 cgg gcc ctg aaa act ata tca gtc att tca ggg ctg aag acc atc gtg     720
Arg Ala Leu Lys Thr Ile Ser Val Ile Ser Gly Leu Lys Thr Ile Val
225                 230                 235                 240 ggg gcc ctg atc cag tct gtg aag aag ctg gct gat gtg atg gtc ctc     768
Gly Ala Leu Ile Gln Ser Val Lys Lys Leu Ala Asp Val Met Val Leu
                245                 250                 255 aca gtc ttc tgc ctc agc gtc ttt gcc ctc atc ggc ctg cag ctc ttc     816
Thr Val Phe Cys Leu Ser Val Phe Ala Leu Ile Gly Leu Gln Leu Phe
            260                 265                 270 atg ggc aac cta agg cac aag tgc gtg cgc aac ttc aca gcg ctc aac     864
Met Gly Asn Leu Arg His Lys Cys Val Arg Asn Phe Thr Ala Leu Asn
        275                 280                 285
```

-continued

```
ggc acc aac ggc tcc gtg gag gcc gac ggc ttg gtc tgg gaa tcc ctg      912
Gly Thr Asn Gly Ser Val Glu Ala Asp Gly Leu Val Trp Glu Ser Leu
290                 295                 300 gac ctt tac ctc agt gat cca gaa aat tac ctg ctc aag aac ggc acc      960
Asp Leu Tyr Leu Ser Asp Pro Glu Asn Tyr Leu Leu Lys Asn Gly Thr
305                 310                 315                 320 tct gat gtg tta ctg tgt ggg aac agc tct gac gct ggg aca tgt ccg     1008
Ser Asp Val Leu Leu Cys Gly Asn Ser Ser Asp Ala Gly Thr Cys Pro
            325                 330                 335 gag ggc tac cgg tgc cta aag gca ggc gag aac ccc gac cac ggc tac     1056
Glu Gly Tyr Arg Cys Leu Lys Ala Gly Glu Asn Pro Asp His Gly Tyr
        340                 345                 350 acc agc ttc gat tcc ttt gcc tgg gcc ttt ctt gca ctc ttc cgc ctg     1104
Thr Ser Phe Asp Ser Phe Ala Trp Ala Phe Leu Ala Leu Phe Arg Leu
    355                 360                 365 atg acg cag gac tgc tgg gag cgc ctc tat cag cag acc ctc agg tcc     1152
Met Thr Gln Asp Cys Trp Glu Arg Leu Tyr Gln Gln Thr Leu Arg Ser
370                 375                 380 gca ggg aag atc tac atg atc ttc ttc atg ctt gtc atc ttc ctg ggg     1200
Ala Gly Lys Ile Tyr Met Ile Phe Phe Met Leu Val Ile Phe Leu Gly
385                 390                 395                 400 tcc ttc tac ctg gtg aac ctg atc ctg gcc gtg gtc gca atg gcc tat     1248
Ser Phe Tyr Leu Val Asn Leu Ile Leu Ala Val Val Ala Met Ala Tyr
            405                 410                 415 gag gag caa aac caa gcc acc atc gct gag acc gag gag aag gaa aag     1296
Glu Glu Gln Asn Gln Ala Thr Ile Ala Glu Thr Glu Glu Lys Glu Lys
        420                 425                 430 cgc ttc cag gag gcc atg gaa atg ctc aag aaa gaa cac gag gcc ctc     1344
Arg Phe Gln Glu Ala Met Glu Met Leu Lys Lys Glu His Glu Ala Leu
    435                 440                 445 acc atc agg ggt gtg gat acc gtg tcc cgt agc tcc ttg gag atg tcc     1392
Thr Ile Arg Gly Val Asp Thr Val Ser Arg Ser Ser Leu Glu Met Ser
450                 455                 460 cct ttg gcc cca gta aac agc cat gag aga aga agc aag agg aga aaa     1440
Pro Leu Ala Pro Val Asn Ser His Glu Arg Arg Ser Lys Arg Arg Lys
465                 470                 475                 480 cgg atg tct tca gga act gag gag tgt ggg gag gac agg ctc ccc aag     1488
Arg Met Ser Ser Gly Thr Glu Glu Cys Gly Glu Asp Arg Leu Pro Lys
            485                 490                 495 tct gac tca gaa gat ggt ccc aga gca atg aat cat ctc agc ctc acc     1536
Ser Asp Ser Glu Asp Gly Pro Arg Ala Met Asn His Leu Ser Leu Thr
        500                 505                 510 cgt ggc ctc agc agg act tct atg aag cca cgt tcc agc cgc ggg agc     1584
Arg Gly Leu Ser Arg Thr Ser Met Lys Pro Arg Ser Ser Arg Gly Ser
    515                 520                 525 att ttc acc ttt cgc agg cga gac ctg ggt tct gaa gca gat ttt gca     1632
Ile Phe Thr Phe Arg Arg Arg Asp Leu Gly Ser Glu Ala Asp Phe Ala
530                 535                 540 gat gat gaa aac agc aca gcg ggg gag agc gag agc cac cgc aca tca     1680
Asp Asp Glu Asn Ser Thr Ala Gly Glu Ser Glu Ser His Arg Thr Ser
545                 550                 555                 560 ctg ctg gtg ccc tgg ccc ctg cgc cgg acc agt gcc cag gga cag ccc     1728
Leu Leu Val Pro Trp Pro Leu Arg Arg Thr Ser Ala Gln Gly Gln Pro
            565                 570                 575 agt ccc gga acc tcg gct cct ggc cac gcc ctc cat ggc aaa aag aac     1776
Ser Pro Gly Thr Ser Ala Pro Gly His Ala Leu His Gly Lys Lys Asn
        580                 585                 590 agc act gtg gac tgc aat ggg gtg gtc tca tta ctg ggg gca ggc gac     1824
Ser Thr Val Asp Cys Asn Gly Val Val Ser Leu Leu Gly Ala Gly Asp
    595                 600                 605
```

```
cca gag gcc aca tcc cca gga agc cac ctc ctc cgc cct gtg atg cta     1872
Pro Glu Ala Thr Ser Pro Gly Ser His Leu Leu Arg Pro Val Met Leu
        610                 615                 620 gag cac ccg cca gac acg acc acg cca tcg gag gag cca ggc ggg ccc     1920
Glu His Pro Pro Asp Thr Thr Thr Pro Ser Glu Glu Pro Gly Gly Pro
625                 630                 635                 640 cag atg ctg acc tcc cag gct ccg tgt gta gat ggc ttc gag gag cca     1968
Gln Met Leu Thr Ser Gln Ala Pro Cys Val Asp Gly Phe Glu Glu Pro
                645                 650                 655 gga gca cgg cag cgg gcc ctc agc gca gtc agc gtc ctc acc agc gca     2016
Gly Ala Arg Gln Arg Ala Leu Ser Ala Val Ser Val Leu Thr Ser Ala
            660                 665                 670 ctg gaa gag tta gag gag tct cgc cac aag tgt cca cca tgc tgg aac     2064
Leu Glu Glu Leu Glu Glu Ser Arg His Lys Cys Pro Pro Cys Trp Asn
        675                 680                 685 cgt ctc gcc cag cgc tac ctg atc tgg gag tgc tgc ccg ctg tgg atg     2112
Arg Leu Ala Gln Arg Tyr Leu Ile Trp Glu Cys Cys Pro Leu Trp Met
    690                 695                 700 tcc atc aag cag gga gtg aag ttg gtg gtc atg gac ccg ttt act gac     2160
Ser Ile Lys Gln Gly Val Lys Leu Val Val Met Asp Pro Phe Thr Asp
705                 710                 715                 720 ctc acc atc act atg tgc atc gta ctc aac aca ctc ttc atg gcg ctg     2208
Leu Thr Ile Thr Met Cys Ile Val Leu Asn Thr Leu Phe Met Ala Leu
                725                 730                 735 gag cac tac aac atg aca agt gaa ttc gag gag atg ctg cag gtc gga     2256
Glu His Tyr Asn Met Thr Ser Glu Phe Glu Glu Met Leu Gln Val Gly
            740                 745                 750 aac ctg gtc ttc aca ggg att ttc aca gca gag atg acc ttc aag atc     2304
Asn Leu Val Phe Thr Gly Ile Phe Thr Ala Glu Met Thr Phe Lys Ile
        755                 760                 765 att gcc ctc gac ccc tac tac tac ttc caa cag ggc tgg aac atc ttc     2352
Ile Ala Leu Asp Pro Tyr Tyr Tyr Phe Gln Gln Gly Trp Asn Ile Phe
    770                 775                 780 gac agc atc atc gtc atc ctt agc ctc atg gag ctg ggc ctg tcc cgc     2400
Asp Ser Ile Ile Val Ile Leu Ser Leu Met Glu Leu Gly Leu Ser Arg
785                 790                 795                 800 atg agc aac ttg tcg gtg ctg cgc tcc ttc cgc ctg ctg cgg gtc ttc     2448
Met Ser Asn Leu Ser Val Leu Arg Ser Phe Arg Leu Leu Arg Val Phe
                805                 810                 815 aag ctg gcc aaa tca tgg ccc acc ctg aac aca ctc atc aag atc atc     2496
Lys Leu Ala Lys Ser Trp Pro Thr Leu Asn Thr Leu Ile Lys Ile Ile
            820                 825                 830 ggg aac tca gtg ggg gca ctg ggg aac ctg aca ctg gtg cta gcc atc     2544
Gly Asn Ser Val Gly Ala Leu Gly Asn Leu Thr Leu Val Leu Ala Ile
        835                 840                 845 atc gtg ttc atc ttt gct gtg gtg ggc atg cag ctc ttt ggc aag aac     2592
Ile Val Phe Ile Phe Ala Val Val Gly Met Gln Leu Phe Gly Lys Asn
    850                 855                 860 tac tcg gag ctg agg gac agc gac tca ggc ctg ctg cct cgc tgg cac     2640
Tyr Ser Glu Leu Arg Asp Ser Asp Ser Gly Leu Leu Pro Arg Trp His
865                 870                 875                 880 atg atg gac ttc ttt cat gcc ttc ctc atc atc ttc cgc atc ctc tgt     2688
Met Met Asp Phe Phe His Ala Phe Leu Ile Ile Phe Arg Ile Leu Cys
                885                 890                 895 gga gag tgg atc gag acc atg tgg gac tgc atg gag gtg tcg ggg cag     2736
Gly Glu Trp Ile Glu Thr Met Trp Asp Cys Met Glu Val Ser Gly Gln
            900                 905                 910 tca tta tgc ctg ctg gtc ttc ttg ctt gtt atg gtc att ggc aac ctt     2784
Ser Leu Cys Leu Leu Val Phe Leu Leu Val Met Val Ile Gly Asn Leu
```

-continued

```
               915                 920                 925
gtg gtc ctg aat ctc ttc ctg gcc ttg ctg ctc agc tcc ttc agt gca    2832
Val Val Leu Asn Leu Phe Leu Ala Leu Leu Leu Ser Ser Phe Ser Ala
        930                 935                 940 gac aac ctc aca gcc cct gat gag gac aga gag atg aac aac ctc cag    2880
Asp Asn Leu Thr Ala Pro Asp Glu Asp Arg Glu Met Asn Asn Leu Gln
945                 950                 955                 960 ctg gcc ctg gcc cgc atc cag agg ggc ctg cgc ttt gtc aag cgg acc    2928
Leu Ala Leu Ala Arg Ile Gln Arg Gly Leu Arg Phe Val Lys Arg Thr
                965                 970                 975 acc tgg gat ttc tgc tgt ggt ctc ctg cgg cag cgg cct cag aag ccc    2976
Thr Trp Asp Phe Cys Cys Gly Leu Leu Arg Gln Arg Pro Gln Lys Pro
                980                 985                 990 gca gcc ctt gcc gcc cag ggc cag  ctg ccc agc tgc att  gcc acc ccc   3024
Ala Ala Leu Ala Ala Gln Gly Gln  Leu Pro Ser Cys Ile  Ala Thr Pro
                995                 1000                1005 tac tcc ccg cca ccc cca gag  acg gag aag gtg cct  ccc acc cgc      3069
Tyr Ser Pro Pro Pro Pro Glu  Thr Glu Lys Val Pro  Pro Thr Arg
     1010                1015                1020 aag gaa aca cgg ttt gag gaa  ggc gag caa cca ggc  cag ggc acc      3114
Lys Glu Thr Arg Phe Glu Glu  Gly Glu Gln Pro Gly  Gln Gly Thr
     1025                1030                1035 ccc ggg gat cca gag ccc gtg  tgt gtg ccc atc gct  gtg gcc gag      3159
Pro Gly Asp Pro Glu Pro Val  Cys Val Pro Ile Ala  Val Ala Glu
     1040                1045                1050 tca gac aca gat gac caa gaa  gaa gat gag gag aac  agc ctg ggc      3204
Ser Asp Thr Asp Asp Gln Glu  Glu Asp Glu Glu Asn  Ser Leu Gly
     1055                1060                1065 acg gag gag gag tcc agc aag  cag cag gaa tcc cag  cct gtg tcc      3249
Thr Glu Glu Glu Ser Ser Lys  Gln Gln Glu Ser Gln  Pro Val Ser
     1070                1075                1080 ggt ggc cca gag gcc cct ccg  gat tcc agg acc tgg  agc cag gtg      3294
Gly Gly Pro Glu Ala Pro Pro  Asp Ser Arg Thr Trp  Ser Gln Val
     1085                1090                1095 tca gcg act gcc tcc tct gag  gcc gag gcc agt gca  tct cag gcc      3339
Ser Ala Thr Ala Ser Ser Glu  Ala Glu Ala Ser Ala  Ser Gln Ala
     1100                1105                1110 gac tgg cgg cag cag tgg aaa  gcg gaa ccc cag gcc  cca ggg tgc      3384
Asp Trp Arg Gln Gln Trp Lys  Ala Glu Pro Gln Ala  Pro Gly Cys
     1115                1120                1125 ggt gag acc cca gag gac agt  tgc tcc gag ggc agc  aca gca gac      3429
Gly Glu Thr Pro Glu Asp Ser  Cys Ser Glu Gly Ser  Thr Ala Asp
     1130                1135                1140 atg acc aac acc gct gag ctc  ctg gag cag atc cct  gac ctc ggc      3474
Met Thr Asn Thr Ala Glu Leu  Leu Glu Gln Ile Pro  Asp Leu Gly
     1145                1150                1155 cag gat gtc aag gac cca gag  gac tgc ttc act gaa  ggc tgt gtc      3519
Gln Asp Val Lys Asp Pro Glu  Asp Cys Phe Thr Glu  Gly Cys Val
     1160                1165                1170 cgg cgc tgt ccc tgc tgt gcg  gtg gac acc aca cag  gcc cca ggg      3564
Arg Arg Cys Pro Cys Cys Ala  Val Asp Thr Thr Gln  Ala Pro Gly
     1175                1180                1185 aag gtc tgg tgg cgg ttg cgc  aag acc tgc tac cac  atc gtg gag      3609
Lys Val Trp Trp Arg Leu Arg  Lys Thr Cys Tyr His  Ile Val Glu
     1190                1195                1200 cac agc tgg ttc gag aca ttc  atc atc ttc atg atc  cta ctc agc      3654
His Ser Trp Phe Glu Thr Phe  Ile Ile Phe Met Ile  Leu Leu Ser
     1205                1210                1215 agt gga gcg ctg gcc ttc gag gac atc tac cta gag gag cgg aag        3699
```

```
                                                -continued

Ser Gly Ala Leu Ala Phe Glu Asp Ile Tyr Leu Glu Glu Arg Lys
1220                1225                1230 acc atc aag gtt ctg ctt gag tat gcc gac aag atg ttc aca tat      3744
Thr Ile Lys Val Leu Leu Glu Tyr Ala Asp Lys Met Phe Thr Tyr
    1235                1240                1245 gtc ttc gtg ctg gag atg ctg ctc aag tgg gtg gcc tac ggc ttc      3789
Val Phe Val Leu Glu Met Leu Leu Lys Trp Val Ala Tyr Gly Phe
        1250                1255                1260 aag aag tac ttc acc aat gcc tgg tgc tgg ctc gac ttc ctc atc      3834
Lys Lys Tyr Phe Thr Asn Ala Trp Cys Trp Leu Asp Phe Leu Ile
    1265                1270                1275 gta gac gtc tct ctg gtc agc ctg gtg gcc aac acc ctg ggc ttt      3879
Val Asp Val Ser Leu Val Ser Leu Val Ala Asn Thr Leu Gly Phe
1280                1285                1290 gcc gag atg ggt ccc atc aag tca ctg cgg acg ctg cgt gca ctc      3924
Ala Glu Met Gly Pro Ile Lys Ser Leu Arg Thr Leu Arg Ala Leu
    1295                1300                1305 cgt cct ctg aga gct ctg tca cga ttt gag ggc atg agg gtg gtg      3969
Arg Pro Leu Arg Ala Leu Ser Arg Phe Glu Gly Met Arg Val Val
1310                1315                1320 gtc aat gcc ctg gtg ggc gcc atc ccg tcc atc atg aac gtc ctc      4014
Val Asn Ala Leu Val Gly Ala Ile Pro Ser Ile Met Asn Val Leu
    1325                1330                1335 ctc gtc tgc ctc atc ttc tgg ctc atc ttc agc atc atg ggc gtg      4059
Leu Val Cys Leu Ile Phe Trp Leu Ile Phe Ser Ile Met Gly Val
        1340                1345                1350 aac ctc ttt gcg ggg aag ttt ggg agg tgc atc aac cag aca gag      4104
Asn Leu Phe Ala Gly Lys Phe Gly Arg Cys Ile Asn Gln Thr Glu
    1355                1360                1365 gga gac ttg cct ttg aac tac acc atc gtg aac aac aag agc cag      4149
Gly Asp Leu Pro Leu Asn Tyr Thr Ile Val Asn Asn Lys Ser Gln
1370                1375                1380 tgt gag tcc ttg aac ttg acc gga gaa ttg tac tgg acc aag gtg      4194
Cys Glu Ser Leu Asn Leu Thr Gly Glu Leu Tyr Trp Thr Lys Val
    1385                1390                1395 aaa gtc aac ttt gac aac gtg ggg gcc ggg tac ctg gcc ctt ctg      4239
Lys Val Asn Phe Asp Asn Val Gly Ala Gly Tyr Leu Ala Leu Leu
        1400                1405                1410 cag gtg gca aca ttt aaa ggc tgg atg gac att atg tat gca gct      4284
Gln Val Ala Thr Phe Lys Gly Trp Met Asp Ile Met Tyr Ala Ala
    1415                1420                1425 gtg gac tcc agg ggg tat gaa gag cag cct cag tgg gaa tac aac      4329
Val Asp Ser Arg Gly Tyr Glu Glu Gln Pro Gln Trp Glu Tyr Asn
1430                1435                1440 ctc tac atg tac atc tat ttt gtc att ttc atc atc ttt ggg tct      4374
Leu Tyr Met Tyr Ile Tyr Phe Val Ile Phe Ile Ile Phe Gly Ser
    1445                1450                1455 ttc ttc acc ctg aac ctc ttt att ggt gtc atc att gac aac ttc      4419
Phe Phe Thr Leu Asn Leu Phe Ile Gly Val Ile Ile Asp Asn Phe
        1460                1465                1470 aac caa cag aag aaa aag tta ggg ggc cag gac atc ttc atg aca      4464
Asn Gln Gln Lys Lys Lys Leu Gly Gly Gln Asp Ile Phe Met Thr
    1475                1480                1485 gag gag cag aag aag tac tac aat gcc atg aag aag ctg ggc tcc      4509
Glu Glu Gln Lys Lys Tyr Tyr Asn Ala Met Lys Lys Leu Gly Ser
1490                1495                1500 aag aag ccc cag aag ccc atc cca cgg ccc ctg aac aag tac cag      4554
Lys Lys Pro Gln Lys Pro Ile Pro Arg Pro Leu Asn Lys Tyr Gln
    1505                1510                1515
```

```
ggc ttc ata ttc gac att gtg acc aag cag gcc ttt gac gtc acc      4599
Gly Phe Ile Phe Asp Ile Val Thr Lys Gln Ala Phe Asp Val Thr
    1520                1525                1530 atc atg ttt ctg atc tgc ttg aat atg gtg acc atg atg gtg gag      4644
Ile Met Phe Leu Ile Cys Leu Asn Met Val Thr Met Met Val Glu
        1535                1540                1545 aca gat gac caa agt cct gag aaa atc aac atc ttg gcc aag atc      4689
Thr Asp Asp Gln Ser Pro Glu Lys Ile Asn Ile Leu Ala Lys Ile
            1550                1555                1560 aac ctg ctc ttt gtg gcc atc ttc aca ggc gag tgt att gtc aag      4734
Asn Leu Leu Phe Val Ala Ile Phe Thr Gly Glu Cys Ile Val Lys
    1565                1570                1575 ctg gct gcc ctg cgc cac tac tac ttc acc aac agc tgg aat atc      4779
Leu Ala Ala Leu Arg His Tyr Tyr Phe Thr Asn Ser Trp Asn Ile
        1580                1585                1590 ttc gac ttc gtg gtt gtc atc ctc tcc atc gtg ggc act gtg ctc      4824
Phe Asp Phe Val Val Val Ile Leu Ser Ile Val Gly Thr Val Leu
            1595                1600                1605 tcg gac atc atc cag aag tac ttc ttc tcc ccg acg ctc ttc cga      4869
Ser Asp Ile Ile Gln Lys Tyr Phe Phe Ser Pro Thr Leu Phe Arg
    1610                1615                1620 gtc atc cgc ctg gcc cga ata ggc cgc atc ctc aga ctg atc cga      4914
Val Ile Arg Leu Ala Arg Ile Gly Arg Ile Leu Arg Leu Ile Arg
        1625                1630                1635 ggg gcc aag ggg atc cgc acg ctg ctc ttt gcc ctc atg atg tcc      4959
Gly Ala Lys Gly Ile Arg Thr Leu Leu Phe Ala Leu Met Met Ser
            1640                1645                1650 ctg cct gcc ctc ttc aac atc ggg ctg ctc ttc ctc gtc atg          5004
Leu Pro Ala Leu Phe Asn Ile Gly Leu Leu Phe Leu Val Met
    1655                1660                1665 ttc atc tac tcc atc ttt ggc atg gcc aac ttc gct tat gtc aag      5049
Phe Ile Tyr Ser Ile Phe Gly Met Ala Asn Phe Ala Tyr Val Lys
        1670                1675                1680 tgg gag gct ggc atc gac gac atg ttc aac ttc cag acc ttc gcc      5094
Trp Glu Ala Gly Ile Asp Asp Met Phe Asn Phe Gln Thr Phe Ala
            1685                1690                1695 aac agc atg ctg tgc ctc ttc cag atc acc acg tcg gcc ggc tgg      5139
Asn Ser Met Leu Cys Leu Phe Gln Ile Thr Thr Ser Ala Gly Trp
    1700                1705                1710 gat ggc ctc ctc agc ccc atc ctc aac act ggg ccg ccc tac tgc      5184
Asp Gly Leu Leu Ser Pro Ile Leu Asn Thr Gly Pro Pro Tyr Cys
        1715                1720                1725 gac ccc act ctg ccc aac agc aat ggc tct cgg ggg gac tgc ggg      5229
Asp Pro Thr Leu Pro Asn Ser Asn Gly Ser Arg Gly Asp Cys Gly
            1730                1735                1740 agc cca gcc gtg ggc atc ctc ttc ttc acc acc tac atc atc atc      5274
Ser Pro Ala Val Gly Ile Leu Phe Phe Thr Thr Tyr Ile Ile Ile
    1745                1750                1755 tcc ttc ctc atc gtg gtc aac atg tac att gcc atc atc ctg gag      5319
Ser Phe Leu Ile Val Val Asn Met Tyr Ile Ala Ile Ile Leu Glu
        1760                1765                1770 aac ttc agc gtg gcc acg gag gag agc acc gag ccc ctg agt gag      5364
Asn Phe Ser Val Ala Thr Glu Glu Ser Thr Glu Pro Leu Ser Glu
            1775                1780                1785 gac gac ttc gat atg ttc tat gag atc tgg gag aaa ttt gac cca      5409
Asp Asp Phe Asp Met Phe Tyr Glu Ile Trp Glu Lys Phe Asp Pro
    1790                1795                1800 gag gcc act cag ttt att gag tat tcg gtc ctg tct gac ttt gcc      5454
Glu Ala Thr Gln Phe Ile Glu Tyr Ser Val Leu Ser Asp Phe Ala
        1805                1810                1815
```

| | | |
|---|---|---|
| gat gcc ctg tct gag cca ctc cgt atc gcc aag ccc aac cag ata<br>Asp Ala Leu Ser Glu Pro Leu Arg Ile Ala Lys Pro Asn Gln Ile<br>1820                        1825                      1830 | 5499 |
| agc ctc atc aac atg gac ctg ccc atg gtg agt ggg gac cgc atc<br>Ser Leu Ile Asn Met Asp Leu Pro Met Val Ser Gly Asp Arg Ile<br>1835                        1840                      1845 | 5544 |
| cat tgc atg gac att ctc ttt gcc ttc acc aaa agg gtc ctg ggg<br>His Cys Met Asp Ile Leu Phe Ala Phe Thr Lys Arg Val Leu Gly<br>1850                        1855                      1860 | 5589 |
| gag tct ggg gag atg gac gcc ctg aag atc cag atg gag gag aag<br>Glu Ser Gly Glu Met Asp Ala Leu Lys Ile Gln Met Glu Glu Lys<br>1865                        1870                      1875 | 5634 |
| ttc atg gca gcc aac cca tcc aag atc tcc tac gag ccc atc acc<br>Phe Met Ala Ala Asn Pro Ser Lys Ile Ser Tyr Glu Pro Ile Thr<br>1880                        1885                      1890 | 5679 |
| acc aca ctc cgg cgc aag cac gaa gag gtg tcg gcc atg gtt atc<br>Thr Thr Leu Arg Arg Lys His Glu Glu Val Ser Ala Met Val Ile<br>1895                        1900                      1905 | 5724 |
| cag aga gcc ttc cgc agg cac ctg ctg caa cgc tct ttg aag cat<br>Gln Arg Ala Phe Arg Arg His Leu Leu Gln Arg Ser Leu Lys His<br>1910                        1915                      1920 | 5769 |
| gcc tcc ttc ctc ttc cgt cag cag gcg ggc agc ggc ctc tcc gaa<br>Ala Ser Phe Leu Phe Arg Gln Gln Ala Gly Ser Gly Leu Ser Glu<br>1925                        1930                      1935 | 5814 |
| gag gat gcc cct gag cga gag ggc ctc atc gcc tac gtg atg agt<br>Glu Asp Ala Pro Glu Arg Glu Gly Leu Ile Ala Tyr Val Met Ser<br>1940                        1945                      1950 | 5859 |
| gag aac ttc tcc cga ccc ctt ggc cca ccc tcc agc tcc tcc atc<br>Glu Asn Phe Ser Arg Pro Leu Gly Pro Pro Ser Ser Ser Ser Ile<br>1955                        1960                      1965 | 5904 |
| tcc tcc act tcc ttc cca ccc tcc tat gac agt gtc act aga gcc<br>Ser Ser Thr Ser Phe Pro Pro Ser Tyr Asp Ser Val Thr Arg Ala<br>1970                        1975                      1980 | 5949 |
| acc agc gat aac ctc cag gtg cgg ggg tct gac tac agc cac agt<br>Thr Ser Asp Asn Leu Gln Val Arg Gly Ser Asp Tyr Ser His Ser<br>1985                        1990                      1995 | 5994 |
| gaa gat ctc gcc gac ttc ccc cct tct ccg gac agg gac cgt gag<br>Glu Asp Leu Ala Asp Phe Pro Pro Ser Pro Asp Arg Asp Arg Glu<br>2000                        2005                      2010 | 6039 |
| tcc atc gtg tgagcctcgg cctggctggc caggacacac tgaaaagcag<br>Ser Ile Val<br>2015 | 6088 |
| ccttttcac catggcaaac ctaaatgcag tcagtcamaa accagcctgg ggccttcctg | 6148 |
| gctttgggag taagaaatgg gcct | 6172 |

<210> SEQ ID NO 4
<211> LENGTH: 2016
<212> TYPE: PRT
<213> ORGANISM: Homo sapiens

<400> SEQUENCE: 4

Met Ala Asn Phe Leu Leu Pro Arg Gly Thr Ser Ser Phe Arg Arg Phe
1               5                 10               15

Thr Arg Glu Ser Leu Ala Ala Ile Glu Lys Arg Met Ala Glu Lys Gln
           20                 25                 30

Ala Arg Gly Ser Thr Thr Leu Gln Glu Ser Arg Glu Gly Leu Pro Glu
               35                 40                 45

Glu Glu Ala Pro Arg Pro Gln Leu Asp Leu Gln Ala Ser Lys Lys Leu

-continued

```
                50                  55                  60
Pro Asp Leu Tyr Gly Asn Pro Pro Gln Glu Leu Ile Gly Glu Pro Leu
 65                  70                  75                  80

Glu Asp Leu Asp Pro Phe Tyr Ser Thr Gln Lys Thr Phe Ile Val Leu
                 85                  90                  95

Asn Lys Gly Lys Thr Ile Phe Arg Phe Ser Ala Thr Asn Ala Leu Tyr
                100                 105                 110

Val Leu Ser Pro Phe His Pro Ile Arg Arg Ala Ala Val Lys Ile Leu
                115                 120                 125

Val His Ser Leu Phe Asn Met Leu Ile Met Cys Thr Ile Leu Thr Asn
130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
                180                 185                 190

Trp Asn Trp Leu Asp Phe Ser Val Ile Ile Met Ala Tyr Thr Thr Glu
                195                 200                 205

Phe Val Asp Leu Gly Asn Val Ser Ala Leu Arg Thr Phe Arg Val Leu
                210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
                260                 265                 270

Met Gly Asn Leu Arg His Lys Cys Val Arg Asn Phe Thr Ala Leu Asn
                275                 280                 285

Gly Thr Asn Gly Ser Val Glu Ala Asp Gly Leu Val Trp Glu Ser Leu
                290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
                340                 345                 350

Thr Ser Phe Asp Ser Phe Ala Trp Ala Phe Leu Ala Leu Phe Arg Leu
                355                 360                 365

Met Thr Gln Asp Cys Trp Glu Arg Leu Tyr Gln Gln Thr Leu Arg Ser
370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
                420                 425                 430

Arg Phe Gln Glu Ala Met Glu Met Leu Lys Lys Glu His Glu Ala Leu
                435                 440                 445

Thr Ile Arg Gly Val Asp Thr Val Ser Arg Ser Ser Leu Glu Met Ser
                450                 455                 460

Pro Leu Ala Pro Val Asn Ser His Glu Arg Arg Ser Lys Arg Arg Lys
465                 470                 475                 480
```

```
Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Asp Leu Gly Ser Glu Ala Asp Phe Ala
    530                 535                 540

Asp Asp Glu Asn Ser Thr Ala Gly Glu Ser Glu Ser His Arg Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895
```

-continued

```
Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
        930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln Leu Pro Ser Cys Ile Ala Thr Pro
        995                 1000                1005

Tyr Ser Pro Pro Pro Glu Thr Glu Lys Val Pro Pro Thr Arg
    1010                1015                1020

Lys Glu Thr Arg Phe Glu Glu Gly Glu Gln Pro Gly Gln Gly Thr
    1025                1030                1035

Pro Gly Asp Pro Glu Pro Val Cys Val Pro Ile Ala Val Ala Glu
    1040                1045                1050

Ser Asp Thr Asp Asp Gln Glu Glu Asp Glu Glu Asn Ser Leu Gly
    1055                1060                1065

Thr Glu Glu Glu Ser Ser Lys Gln Gln Glu Ser Gln Pro Val Ser
    1070                1075                1080

Gly Gly Pro Glu Ala Pro Pro Asp Ser Arg Thr Trp Ser Gln Val
    1085                1090                1095

Ser Ala Thr Ala Ser Ser Glu Ala Glu Ala Ser Ala Ser Gln Ala
    1100                1105                1110

Asp Trp Arg Gln Gln Trp Lys Ala Glu Pro Gln Ala Pro Gly Cys
    1115                1120                1125

Gly Glu Thr Pro Glu Asp Ser Cys Ser Glu Gly Ser Thr Ala Asp
    1130                1135                1140

Met Thr Asn Thr Ala Glu Leu Leu Glu Gln Ile Pro Asp Leu Gly
    1145                1150                1155

Gln Asp Val Lys Asp Pro Glu Asp Cys Phe Thr Glu Gly Cys Val
    1160                1165                1170

Arg Arg Cys Pro Cys Cys Ala Val Asp Thr Thr Gln Ala Pro Gly
    1175                1180                1185

Lys Val Trp Trp Arg Leu Arg Lys Thr Cys Tyr His Ile Val Glu
    1190                1195                1200

His Ser Trp Phe Glu Thr Phe Ile Ile Phe Met Ile Leu Leu Ser
    1205                1210                1215

Ser Gly Ala Leu Ala Phe Glu Asp Ile Tyr Leu Glu Glu Arg Lys
    1220                1225                1230

Thr Ile Lys Val Leu Leu Glu Tyr Ala Asp Lys Met Phe Thr Tyr
    1235                1240                1245

Val Phe Val Leu Glu Met Leu Leu Lys Trp Val Ala Tyr Gly Phe
    1250                1255                1260

Lys Lys Tyr Phe Thr Asn Ala Trp Cys Trp Leu Asp Phe Leu Ile
    1265                1270                1275

Val Asp Val Ser Leu Val Ser Leu Val Ala Asn Thr Leu Gly Phe
    1280                1285                1290

Ala Glu Met Gly Pro Ile Lys Ser Leu Arg Thr Leu Arg Ala Leu
```

```
            1295                1300                1305

Arg Pro Leu Arg Ala Leu Ser Arg Phe Glu Gly Met Arg Val Val
    1310                1315                1320

Val Asn Ala Leu Val Gly Ala Ile Pro Ser Ile Met Asn Val Leu
    1325                1330                1335

Leu Val Cys Leu Ile Phe Trp Leu Ile Phe Ser Ile Met Gly Val
    1340                1345                1350

Asn Leu Phe Ala Gly Lys Phe Gly Arg Cys Ile Asn Gln Thr Glu
    1355                1360                1365

Gly Asp Leu Pro Leu Asn Tyr Thr Ile Val Asn Asn Lys Ser Gln
    1370                1375                1380

Cys Glu Ser Leu Asn Leu Thr Gly Glu Leu Tyr Trp Thr Lys Val
    1385                1390                1395

Lys Val Asn Phe Asp Asn Val Gly Ala Gly Tyr Leu Ala Leu Leu
    1400                1405                1410

Gln Val Ala Thr Phe Lys Gly Trp Met Asp Ile Met Tyr Ala Ala
    1415                1420                1425

Val Asp Ser Arg Gly Tyr Glu Glu Gln Pro Gln Trp Glu Tyr Asn
    1430                1435                1440

Leu Tyr Met Tyr Ile Tyr Phe Val Ile Phe Ile Ile Phe Gly Ser
    1445                1450                1455

Phe Phe Thr Leu Asn Leu Phe Ile Gly Val Ile Ile Asp Asn Phe
    1460                1465                1470

Asn Gln Gln Lys Lys Lys Leu Gly Gly Gln Asp Ile Phe Met Thr
    1475                1480                1485

Glu Glu Gln Lys Lys Tyr Tyr Asn Ala Met Lys Lys Leu Gly Ser
    1490                1495                1500

Lys Lys Pro Gln Lys Pro Ile Pro Arg Pro Leu Asn Lys Tyr Gln
    1505                1510                1515

Gly Phe Ile Phe Asp Ile Val Thr Lys Gln Ala Phe Asp Val Thr
    1520                1525                1530

Ile Met Phe Leu Ile Cys Leu Asn Met Val Thr Met Met Val Glu
    1535                1540                1545

Thr Asp Asp Gln Ser Pro Glu Lys Ile Asn Ile Leu Ala Lys Ile
    1550                1555                1560

Asn Leu Leu Phe Val Ala Ile Phe Thr Gly Glu Cys Ile Val Lys
    1565                1570                1575

Leu Ala Ala Leu Arg His Tyr Tyr Phe Thr Asn Ser Trp Asn Ile
    1580                1585                1590

Phe Asp Phe Val Val Val Ile Leu Ser Ile Val Gly Thr Val Leu
    1595                1600                1605

Ser Asp Ile Ile Gln Lys Tyr Phe Phe Ser Pro Thr Leu Phe Arg
    1610                1615                1620

Val Ile Arg Leu Ala Arg Ile Gly Arg Ile Leu Arg Leu Ile Arg
    1625                1630                1635

Gly Ala Lys Gly Ile Arg Thr Leu Leu Phe Ala Leu Met Met Ser
    1640                1645                1650

Leu Pro Ala Leu Phe Asn Ile Gly Leu Leu Leu Phe Leu Val Met
    1655                1660                1665

Phe Ile Tyr Ser Ile Phe Gly Met Ala Asn Phe Ala Tyr Val Lys
    1670                1675                1680

Trp Glu Ala Gly Ile Asp Asp Met Phe Asn Phe Gln Thr Phe Ala
    1685                1690                1695
```

```
Asn Ser Met Leu Cys Leu Phe Gln Ile Thr Thr Ser Ala Gly Trp
    1700                1705                1710

Asp Gly Leu Leu Ser Pro Ile Leu Asn Thr Gly Pro Pro Tyr Cys
    1715                1720                1725

Asp Pro Thr Leu Pro Asn Ser Asn Gly Ser Arg Gly Asp Cys Gly
    1730                1735                1740

Ser Pro Ala Val Gly Ile Leu Phe Phe Thr Thr Tyr Ile Ile Ile
    1745                1750                1755

Ser Phe Leu Ile Val Val Asn Met Tyr Ile Ala Ile Ile Leu Glu
    1760                1765                1770

Asn Phe Ser Val Ala Thr Glu Glu Ser Thr Glu Pro Leu Ser Glu
    1775                1780                1785

Asp Asp Phe Asp Met Phe Tyr Glu Ile Trp Glu Lys Phe Asp Pro
    1790                1795                1800

Glu Ala Thr Gln Phe Ile Glu Tyr Ser Val Leu Ser Asp Phe Ala
    1805                1810                1815

Asp Ala Leu Ser Glu Pro Leu Arg Ile Ala Lys Pro Asn Gln Ile
    1820                1825                1830

Ser Leu Ile Asn Met Asp Leu Pro Met Val Ser Gly Asp Arg Ile
    1835                1840                1845

His Cys Met Asp Ile Leu Phe Ala Phe Thr Lys Arg Val Leu Gly
    1850                1855                1860

Glu Ser Gly Glu Met Asp Ala Leu Lys Ile Gln Met Glu Glu Lys
    1865                1870                1875

Phe Met Ala Ala Asn Pro Ser Lys Ile Ser Tyr Glu Pro Ile Thr
    1880                1885                1890

Thr Thr Leu Arg Arg Lys His Glu Glu Val Ser Ala Met Val Ile
    1895                1900                1905

Gln Arg Ala Phe Arg Arg His Leu Leu Gln Arg Ser Leu Lys His
    1910                1915                1920

Ala Ser Phe Leu Phe Arg Gln Gln Ala Gly Ser Gly Leu Ser Glu
    1925                1930                1935

Glu Asp Ala Pro Glu Arg Glu Gly Leu Ile Ala Tyr Val Met Ser
    1940                1945                1950

Glu Asn Phe Ser Arg Pro Leu Gly Pro Pro Ser Ser Ser Ser Ile
    1955                1960                1965

Ser Ser Thr Ser Phe Pro Pro Ser Tyr Asp Ser Val Thr Arg Ala
    1970                1975                1980

Thr Ser Asp Asn Leu Gln Val Arg Gly Ser Asp Tyr Ser His Ser
    1985                1990                1995

Glu Asp Leu Ala Asp Phe Pro Pro Ser Pro Asp Arg Asp Arg Glu
    2000                2005                2010

Ser Ile Val
    2015

<210> SEQ ID NO 5
<211> LENGTH: 6169
<212> TYPE: DNA
<213> ORGANISM: Homo sapiens
<220> FEATURE:
<221> NAME/KEY: CDS
<222> LOCATION: (1)..(6045)

<400> SEQUENCE: 5 atg gca aac ttc cta tta cct agg ggc acc agc agc ttc cgc agg ttc      48
```

```
Met Ala Asn Phe Leu Leu Pro Arg Gly Thr Ser Ser Phe Arg Arg Phe
 1               5                  10                 15 aca cgg gag tcc ctg gca gcc atc gag aag cgc atg gcg gag aag caa    96
Thr Arg Glu Ser Leu Ala Ala Ile Glu Lys Arg Met Ala Glu Lys Gln
             20                  25                  30 gcc cgc ggc tca acc acc ttg cag gag agc cga gag ggg ctg ccc gag   144
Ala Arg Gly Ser Thr Thr Leu Gln Glu Ser Arg Glu Gly Leu Pro Glu
                 35                  40                  45 gag gag gct ccc cgg ccc cag ctg gac ctg cag gcc tcc aaa aag ctg   192
Glu Glu Ala Pro Arg Pro Gln Leu Asp Leu Gln Ala Ser Lys Lys Leu
         50                  55                  60 cca gat ctc tat ggc aat cca ccc caa gag ctc atc gga gag ccc ctg   240
Pro Asp Leu Tyr Gly Asn Pro Pro Gln Glu Leu Ile Gly Glu Pro Leu
 65              70                  75                  80 gag gac ctg gac ccc ttc tat agc acc caa aag act ttc atc gta ctg   288
Glu Asp Leu Asp Pro Phe Tyr Ser Thr Gln Lys Thr Phe Ile Val Leu
                 85                  90                  95 aat aaa ggc aag acc atc ttc cgg ttc agt gcc acc aac gcc ttg tat   336
Asn Lys Gly Lys Thr Ile Phe Arg Phe Ser Ala Thr Asn Ala Leu Tyr
                100                 105                 110 gtc ctc agt ccc ttc cac ccc atc cgg aga gcg gct gtg aag att ctg   384
Val Leu Ser Pro Phe His Pro Ile Arg Arg Ala Ala Val Lys Ile Leu
             115                 120                 125 gtt cac tcg ctc ttc aac atg ctc atc atg tgc acc atc ctc acc aac   432
Val His Ser Leu Phe Asn Met Leu Ile Met Cys Thr Ile Leu Thr Asn
 130                 135                 140 tgc gtg ttc atg gcc cag cac gac cct cca ccc tgg acc aag tat gtc   480
Cys Val Phe Met Ala Gln His Asp Pro Pro Pro Trp Thr Lys Tyr Val
 145                 150                 155                 160 gag tac acc ttc acc gcc att tac acc ttt gag tct ctg gtc aag att   528
Glu Tyr Thr Phe Thr Ala Ile Tyr Thr Phe Glu Ser Leu Val Lys Ile
                 165                 170                 175 ctg gct cga ggc ttc tgc ctg cac gcg ttc act ttc ctt cgg gac cca   576
Leu Ala Arg Gly Phe Cys Leu His Ala Phe Thr Phe Leu Arg Asp Pro
             180                 185                 190 tgg aac tgg ctg gac ttt agt gtg att atc atg gca tac aca act gaa   624
Trp Asn Trp Leu Asp Phe Ser Val Ile Ile Met Ala Tyr Thr Thr Glu
         195                 200                 205 ttt gtg gac ctg ggc aat gtc tca gcc tta cgc acc ttc cga gtc ctc   672
Phe Val Asp Leu Gly Asn Val Ser Ala Leu Arg Thr Phe Arg Val Leu
 210                 215                 220 cgg gcc ctg aaa act ata tca gtc att tca ggg ctg aag acc atc gtg   720
Arg Ala Leu Lys Thr Ile Ser Val Ile Ser Gly Leu Lys Thr Ile Val
 225                 230                 235                 240 ggg gcc ctg atc cag tct gtg aag aag ctg gct gat gtg atg gtc ctc   768
Gly Ala Leu Ile Gln Ser Val Lys Lys Leu Ala Asp Val Met Val Leu
                 245                 250                 255 aca gtc ttc tgc ctc agc gtc ttt gcc ctc atc ggc ctg cag ctc ttc   816
Thr Val Phe Cys Leu Ser Val Phe Ala Leu Ile Gly Leu Gln Leu Phe
             260                 265                 270 atg ggc aac cta agg cac aag tgc gtg cgc aac ttc aca gcg ctc aac   864
Met Gly Asn Leu Arg His Lys Cys Val Arg Asn Phe Thr Ala Leu Asn
         275                 280                 285 ggc acc aac ggc tcc gtg gag gcc gac ggc ttg gtc tgg gaa tcc ctg   912
Gly Thr Asn Gly Ser Val Glu Ala Asp Gly Leu Val Trp Glu Ser Leu
 290                 295                 300 gac ctt tac ctc agt gat cca gaa aat tac ctg ctc aag aac ggc acc   960
Asp Leu Tyr Leu Ser Asp Pro Glu Asn Tyr Leu Leu Lys Asn Gly Thr
 305                 310                 315                 320
```

```
                                              -continued
tct gat gtg tta ctg tgt ggg aac agc tct gac gct ggg aca tgt ccg    1008
Ser Asp Val Leu Leu Cys Gly Asn Ser Ser Asp Ala Gly Thr Cys Pro
            325                 330                 335 gag ggc tac cgg tgc cta aag gca ggc gag aac ccc gac cac ggc tac    1056
Glu Gly Tyr Arg Cys Leu Lys Ala Gly Glu Asn Pro Asp His Gly Tyr
340                 345                 350 acc agc ttc gat tcc ttt gcc tgg gcc ttt ctt gca ctc ttc cgc ctg    1104
Thr Ser Phe Asp Ser Phe Ala Trp Ala Phe Leu Ala Leu Phe Arg Leu
        355                 360                 365 atg acg cag gac tgc tgg gag cgc ctc tat cag cag acc ctc agg tcc    1152
Met Thr Gln Asp Cys Trp Glu Arg Leu Tyr Gln Gln Thr Leu Arg Ser
    370                 375                 380 gca ggg aag atc tac atg atc ttc ttc atg ctt gtc atc ttc ctg ggg    1200
Ala Gly Lys Ile Tyr Met Ile Phe Phe Met Leu Val Ile Phe Leu Gly
385                 390                 395                 400 tcc ttc tac ctg gtg aac ctg atc ctg gcc gtg gtc gca atg gcc tat    1248
Ser Phe Tyr Leu Val Asn Leu Ile Leu Ala Val Val Ala Met Ala Tyr
                405                 410                 415 gag gag caa aac caa gcc acc atc gct gag acc gag gag aag gaa aag    1296
Glu Glu Gln Asn Gln Ala Thr Ile Ala Glu Thr Glu Glu Lys Glu Lys
            420                 425                 430 cgc ttc cag gag gcc atg gaa atg ctc aag aaa gaa cac gag gcc ctc    1344
Arg Phe Gln Glu Ala Met Glu Met Leu Lys Lys Glu His Glu Ala Leu
        435                 440                 445 acc atc agg ggt gtg gat acc gtg tcc cgt agc tcc ttg gag atg tcc    1392
Thr Ile Arg Gly Val Asp Thr Val Ser Arg Ser Ser Leu Glu Met Ser
    450                 455                 460 cct ttg gcc cca gta aac agc cat gag aga aga agc aag agg aga aaa    1440
Pro Leu Ala Pro Val Asn Ser His Glu Arg Arg Ser Lys Arg Arg Lys
465                 470                 475                 480 cgg atg tct tca gga act gag gag tgt ggg gag gac agg ctc ccc aag    1488
Arg Met Ser Ser Gly Thr Glu Glu Cys Gly Glu Asp Arg Leu Pro Lys
                485                 490                 495 tct gac tca gaa gat ggt ccc aga gca atg aat cat ctc agc ctc acc    1536
Ser Asp Ser Glu Asp Gly Pro Arg Ala Met Asn His Leu Ser Leu Thr
            500                 505                 510 cgt ggc ctc agc agg act tct atg aag cca cgt tcc agc cgc ggg agc    1584
Arg Gly Leu Ser Arg Thr Ser Met Lys Pro Arg Ser Ser Arg Gly Ser
        515                 520                 525 att ttc acc ttt cgc agg cga gac ctg ggt tct gaa gca gat ttt gca    1632
Ile Phe Thr Phe Arg Arg Arg Asp Leu Gly Ser Glu Ala Asp Phe Ala
    530                 535                 540 gat gat gaa aac agc aca gcg ggg gag agc gag agc cac cac aca tca    1680
Asp Asp Glu Asn Ser Thr Ala Gly Glu Ser Glu Ser His His Thr Ser
545                 550                 555                 560 ctg ctg gtg ccc tgg ccc ctg cgc cgg acc agt gcc cag gga cag ccc    1728
Leu Leu Val Pro Trp Pro Leu Arg Arg Thr Ser Ala Gln Gly Gln Pro
                565                 570                 575 agt ccc gga acc tcg gct cct ggc cac gcc ctc cat ggc aaa aag aac    1776
Ser Pro Gly Thr Ser Ala Pro Gly His Ala Leu His Gly Lys Lys Asn
            580                 585                 590 agc act gtg gac tgc aat ggg gtg gtc tca tta ctg ggg gca ggc gac    1824
Ser Thr Val Asp Cys Asn Gly Val Val Ser Leu Leu Gly Ala Gly Asp
        595                 600                 605 cca gag gcc aca tcc cca gga agc cac ctc ctc cgc cct gtg atg cta    1872
Pro Glu Ala Thr Ser Pro Gly Ser His Leu Leu Arg Pro Val Met Leu
    610                 615                 620 gag cac ccg cca gac acg acc acg cca tcg gag gag cca ggg ggg ccc    1920
Glu His Pro Pro Asp Thr Thr Thr Pro Ser Glu Glu Pro Gly Gly Pro
625                 630                 635                 640
```

```
cag atg ctg acc tcc cag gct ccg tgt gta gat ggc ttc gag gag cca    1968
Gln Met Leu Thr Ser Gln Ala Pro Cys Val Asp Gly Phe Glu Glu Pro
            645                 650                 655 gga gca cgg cag cgg gcc ctc agc gca gtc agc gtc ctc acc agc gca    2016
Gly Ala Arg Gln Arg Ala Leu Ser Ala Val Ser Val Leu Thr Ser Ala
        660                 665                 670 ctg gaa gag tta gag gag tct cgc cac aag tgt cca cca tgc tgg aac    2064
Leu Glu Glu Leu Glu Glu Ser Arg His Lys Cys Pro Pro Cys Trp Asn
    675                 680                 685 cgt ctc gcc cag cgc tac ctg atc tgg gag tgc tgc ccg ctg tgg atg    2112
Arg Leu Ala Gln Arg Tyr Leu Ile Trp Glu Cys Cys Pro Leu Trp Met
690                 695                 700 tcc atc aag cag gga gtg aag ttg gtg gtc atg gac ccg ttt act gac    2160
Ser Ile Lys Gln Gly Val Lys Leu Val Val Met Asp Pro Phe Thr Asp
705                 710                 715                 720 ctc acc atc act atg tgc atc gta ctc aac aca ctc ttc atg gcg ctg    2208
Leu Thr Ile Thr Met Cys Ile Val Leu Asn Thr Leu Phe Met Ala Leu
                725                 730                 735 gag cac tac aac atg aca agt gaa ttc gag gag atg ctg cag gtc gga    2256
Glu His Tyr Asn Met Thr Ser Glu Phe Glu Glu Met Leu Gln Val Gly
            740                 745                 750 aac ctg gtc ttc aca ggg att ttc aca gca gag atg acc ttc aag atc    2304
Asn Leu Val Phe Thr Gly Ile Phe Thr Ala Glu Met Thr Phe Lys Ile
        755                 760                 765 att gcc ctc gac ccc tac tac tac ttc caa cag ggc tgg aac atc ttc    2352
Ile Ala Leu Asp Pro Tyr Tyr Tyr Phe Gln Gln Gly Trp Asn Ile Phe
    770                 775                 780 gac agc atc atc gtc atc ctt agc ctc atg gag ctg ggc ctg tcc cgc    2400
Asp Ser Ile Ile Val Ile Leu Ser Leu Met Glu Leu Gly Leu Ser Arg
785                 790                 795                 800 atg agc aac ttg tcg gtg ctg cgc tcc ttc cgc ctg ctg cgg gtc ttc    2448
Met Ser Asn Leu Ser Val Leu Arg Ser Phe Arg Leu Leu Arg Val Phe
                805                 810                 815 aag ctg gcc aaa tca tgg ccc acc ctg aac aca ctc atc aag atc atc    2496
Lys Leu Ala Lys Ser Trp Pro Thr Leu Asn Thr Leu Ile Lys Ile Ile
            820                 825                 830 ggg aac tca gtg ggg gca ctg ggg aac ctg aca ctg gtg cta gcc atc    2544
Gly Asn Ser Val Gly Ala Leu Gly Asn Leu Thr Leu Val Leu Ala Ile
        835                 840                 845 atc gtg ttc atc ttt gct gtg gtg ggc atg cag ctc ttt ggc aag aac    2592
Ile Val Phe Ile Phe Ala Val Val Gly Met Gln Leu Phe Gly Lys Asn
    850                 855                 860 tac tcg gag ctg agg gac agc gac tca ggc ctg ctg cct cgc tgg cac    2640
Tyr Ser Glu Leu Arg Asp Ser Asp Ser Gly Leu Leu Pro Arg Trp His
865                 870                 875                 880 atg atg gac ttc ttt cat gcc ttc ctc atc atc ttc cgc atc ctc tgt    2688
Met Met Asp Phe Phe His Ala Phe Leu Ile Ile Phe Arg Ile Leu Cys
                885                 890                 895 gga gag tgg atc gag acc atg tgg gac tgc atg gag gtg tcg ggg cag    2736
Gly Glu Trp Ile Glu Thr Met Trp Asp Cys Met Glu Val Ser Gly Gln
            900                 905                 910 tca tta tgc ctg ctg gtc ttc ttg ctt gtt atg gtc att ggc aac ctt    2784
Ser Leu Cys Leu Leu Val Phe Leu Leu Val Met Val Ile Gly Asn Leu
        915                 920                 925 gtg gtc ctg aat ctc ttc ctg gcc ttg ctg ctc agc tcc ttc agt gca    2832
Val Val Leu Asn Leu Phe Leu Ala Leu Leu Leu Ser Ser Phe Ser Ala
    930                 935                 940 gac aac ctc aca gcc cct gat gag gac aga gag atg aac aac ctc cag    2880
Asp Asn Leu Thr Ala Pro Asp Glu Asp Arg Glu Met Asn Asn Leu Gln
```

-continued

```
            945                 950                 955                 960
ctg gcc ctg gcc cgc atc cag agg ggc ctg cgc ttt gtc aag cgg acc              2928
Leu Ala Leu Ala Arg Ile Gln Arg Gly Leu Arg Phe Val Lys Arg Thr
                    965                 970                 975 acc tgg gat ttc tgc tgt ggt ctc ctg cgg cag cgg cct cag aag ccc              2976
Thr Trp Asp Phe Cys Cys Gly Leu Leu Arg Gln Arg Pro Gln Lys Pro
                980                 985                 990 gca gcc ctt gcc gcc cag ggc cag  ctg ccc agc tgc att  gcc acc ccc            3024
Ala Ala Leu Ala Ala Gln Gly Gln  Leu Pro Ser Cys Ile  Ala Thr Pro
            995                 1000                1005 tac tcc ccg cca ccc cca gag  acg gag aag gtg cct  ccc acc cgc                3069
Tyr Ser Pro Pro Pro Pro Glu  Thr Glu Lys Val Pro  Pro Thr Arg
            1010                1015                1020 aag gaa aca cgg ttt gag gaa  ggc gag caa cca ggc  cag ggc acc                3114
Lys Glu Thr Arg Phe Glu Glu  Gly Glu Gln Pro Gly  Gln Gly Thr
            1025                1030                1035 ccc ggg gat cca gag ccc gtg  tgt gtg ccc atc gct  gtg gcc gag                3159
Pro Gly Asp Pro Glu Pro Val  Cys Val Pro Ile Ala  Val Ala Glu
            1040                1045                1050 tca gac aca gat gac caa gaa  gaa gat gag gag aac  agc ctg ggc                3204
Ser Asp Thr Asp Asp Gln Glu  Glu Asp Glu Glu Asn  Ser Leu Gly
            1055                1060                1065 acg gag gag gag tcc agc aag  cag gaa tcc cag cct  gtg tcc ggt                3249
Thr Glu Glu Glu Ser Ser Lys  Gln Glu Ser Gln Pro  Val Ser Gly
            1070                1075                1080 ggc cca gag gcc cct ccg gat  tcc agg acc tgg agc  cag gtg tca                3294
Gly Pro Glu Ala Pro Pro Asp  Ser Arg Thr Trp Ser  Gln Val Ser
            1085                1090                1095 gcg act gcc tcc tct gag gcc  gag gcc agt gca tct  cag gcc gac                3339
Ala Thr Ala Ser Ser Glu Ala  Glu Ala Ser Ala Ser  Gln Ala Asp
            1100                1105                1110 tgg cgg cag cag tgg aaa gcg  gaa ccc cag gcc cca  ggg tgc ggt                3384
Trp Arg Gln Gln Trp Lys Ala  Glu Pro Gln Ala Pro  Gly Cys Gly
            1115                1120                1125 gag acc cca gag gac agt tgc  tcc gag ggc agc aca  gca gac atg                3429
Glu Thr Pro Glu Asp Ser Cys  Ser Glu Gly Ser Thr  Ala Asp Met
            1130                1135                1140 acc aac acc gct gag ctc ctg  gag cag atc cct gac  ctc ggc cag                3474
Thr Asn Thr Ala Glu Leu Leu  Glu Gln Ile Pro Asp  Leu Gly Gln
            1145                1150                1155 gat gtc aag gac cca gag gac  tgc ttc act gaa ggc  tgt gtc cgg                3519
Asp Val Lys Asp Pro Glu Asp  Cys Phe Thr Glu Gly  Cys Val Arg
            1160                1165                1170 cgc tgt ccc tgc tgt gcg gtg  gac acc aca cag gcc  cca ggg aag                3564
Arg Cys Pro Cys Cys Ala Val  Asp Thr Thr Gln Ala  Pro Gly Lys
            1175                1180                1185 gtc tgg tgg cgg ttg cgc aag  acc tgc tac cac atc  gtg gag cac                3609
Val Trp Trp Arg Leu Arg Lys  Thr Cys Tyr His Ile  Val Glu His
            1190                1195                1200 agc tgg ttc gag aca ttc atc  atc ttc atg atc cta  ctc agc agt                3654
Ser Trp Phe Glu Thr Phe Ile  Ile Phe Met Ile Leu  Leu Ser Ser
            1205                1210                1215 gga gcg ctg gcc ttc gag gac  atc tac cta gag gag  cgg aag acc                3699
Gly Ala Leu Ala Phe Glu Asp  Ile Tyr Leu Glu Glu  Arg Lys Thr
            1220                1225                1230 atc aag gtt ctg ctt gag tat  gcc gac aag atg ttc  aca tat gtc                3744
Ile Lys Val Leu Leu Glu Tyr  Ala Asp Lys Met Phe  Thr Tyr Val
            1235                1240                1245 ttc gtg ctg gag atg ctg ctc  aag tgg gtg gcc tac  ggc ttc aag                3789
```

```
                                        -continued

Phe Val Leu Glu Met Leu Leu Lys Trp Val Ala Tyr Gly Phe Lys
    1250                1255                1260 aag tac ttc acc aat gcc tgg tgc tgg ctc gac ttc ctc atc gta         3834
Lys Tyr Phe Thr Asn Ala Trp Cys Trp Leu Asp Phe Leu Ile Val
    1265                1270                1275 gac gtc tct ctg gtc agc ctg gtg gcc aac acc ctg ggc ttt gcc         3879
Asp Val Ser Leu Val Ser Leu Val Ala Asn Thr Leu Gly Phe Ala
    1280                1285                1290 gag atg ggt ccc atc aag tca ctg cgg acg ctg cgt gca ctc cgt         3924
Glu Met Gly Pro Ile Lys Ser Leu Arg Thr Leu Arg Ala Leu Arg
    1295                1300                1305 cct ctg aga gct ctg tca cga ttt gag ggc atg agg gtg gtg gtc         3969
Pro Leu Arg Ala Leu Ser Arg Phe Glu Gly Met Arg Val Val Val
    1310                1315                1320 aat gcc ctg gtg ggc gcc atc ccg tcc atc atg aac gtc ctc ctc         4014
Asn Ala Leu Val Gly Ala Ile Pro Ser Ile Met Asn Val Leu Leu
    1325                1330                1335 gtc tgc ctc atc ttc tgg ctc atc ttc agc atc atg ggc gtg aac         4059
Val Cys Leu Ile Phe Trp Leu Ile Phe Ser Ile Met Gly Val Asn
    1340                1345                1350 ctc ttt gcg ggg aag ttt ggg agg tgc atc aac cag aca gag gga         4104
Leu Phe Ala Gly Lys Phe Gly Arg Cys Ile Asn Gln Thr Glu Gly
    1355                1360                1365 gac ttg cct ttg aac tac acc atc gtg aac aac aag agc cag tgt         4149
Asp Leu Pro Leu Asn Tyr Thr Ile Val Asn Asn Lys Ser Gln Cys
    1370                1375                1380 gag tcc ttg aac ttg acc gga gaa ttg tac tgg acc aag gtg aaa         4194
Glu Ser Leu Asn Leu Thr Gly Glu Leu Tyr Trp Thr Lys Val Lys
    1385                1390                1395 gtc aac ttt gac aac gtg ggg gcc ggg tac ctg gcc ctt ctg cag         4239
Val Asn Phe Asp Asn Val Gly Ala Gly Tyr Leu Ala Leu Leu Gln
    1400                1405                1410 gtg gca aca ttt aaa ggc tgg atg gac att atg tat gca gct gtg         4284
Val Ala Thr Phe Lys Gly Trp Met Asp Ile Met Tyr Ala Ala Val
    1415                1420                1425 gac tcc agg ggg tat gaa gag cag cct cag tgg gaa tac aac ctc         4329
Asp Ser Arg Gly Tyr Glu Glu Gln Pro Gln Trp Glu Tyr Asn Leu
    1430                1435                1440 tac atg tac atc tat ttt gtc att ttc atc atc ttt ggg tct ttc         4374
Tyr Met Tyr Ile Tyr Phe Val Ile Phe Ile Ile Phe Gly Ser Phe
    1445                1450                1455 ttc acc ctg aac ctc ttt att ggt gtc atc att gac aac ttc aac         4419
Phe Thr Leu Asn Leu Phe Ile Gly Val Ile Ile Asp Asn Phe Asn
    1460                1465                1470 caa cag aag aaa aag tta ggg ggc cag gac atc ttc atg aca gag         4464
Gln Gln Lys Lys Lys Leu Gly Gly Gln Asp Ile Phe Met Thr Glu
    1475                1480                1485 gag cag aag aag tac tac aat gcc atg aag aag ctg ggc tcc aag         4509
Glu Gln Lys Lys Tyr Tyr Asn Ala Met Lys Lys Leu Gly Ser Lys
    1490                1495                1500 aag ccc cag aag ccc atc cca cgg ccc ctg aac aag tac cag ggc         4554
Lys Pro Gln Lys Pro Ile Pro Arg Pro Leu Asn Lys Tyr Gln Gly
    1505                1510                1515 ttc ata ttc gac att gtg acc aag cag gcc ttt gac gtc acc atc         4599
Phe Ile Phe Asp Ile Val Thr Lys Gln Ala Phe Asp Val Thr Ile
    1520                1525                1530 atg ttt ctg atc tgc ttg aat atg gtg acc atg atg gtg gag aca         4644
Met Phe Leu Ile Cys Leu Asn Met Val Thr Met Met Val Glu Thr
    1535                1540                1545
```

```
gat gac caa agt cct gag aaa atc aac atc ttg gcc aag atc aac         4689
Asp Asp Gln Ser Pro Glu Lys Ile Asn Ile Leu Ala Lys Ile Asn
1550                1555                1560 ctg ctc ttt gtg gcc atc ttc aca ggc gag tgt att gtc aag ctg         4734
Leu Leu Phe Val Ala Ile Phe Thr Gly Glu Cys Ile Val Lys Leu
    1565                1570                1575 gct gcc ctg cgc cac tac tac ttc acc aac agc tgg aat atc ttc         4779
Ala Ala Leu Arg His Tyr Tyr Phe Thr Asn Ser Trp Asn Ile Phe
1580                1585                1590 gac ttc gtg gtt gtc atc ctc tcc atc gtg ggc act gtg ctc tcg         4824
Asp Phe Val Val Val Ile Leu Ser Ile Val Gly Thr Val Leu Ser
    1595                1600                1605 gac atc atc cag aag tac ttc ttc tcc ccg acg ctc ttc cga gtc         4869
Asp Ile Ile Gln Lys Tyr Phe Phe Ser Pro Thr Leu Phe Arg Val
1610                1615                1620 atc cgc ctg gcc cga ata ggc cgc atc ctc aga ctg atc cga ggg         4914
Ile Arg Leu Ala Arg Ile Gly Arg Ile Leu Arg Leu Ile Arg Gly
    1625                1630                1635 gcc aag ggg atc cgc acg ctg ctc ttt gcc ctc atg atg tcc ctg         4959
Ala Lys Gly Ile Arg Thr Leu Leu Phe Ala Leu Met Met Ser Leu
1640                1645                1650 cct gcc ctc ttc aac atc ggg ctg ctc ttc ctc gtc atg ttc             5004
Pro Ala Leu Phe Asn Ile Gly Leu Leu Leu Phe Leu Val Met Phe
    1655                1660                1665 atc tac tcc atc ttt ggc atg gcc aac ttc gct tat gtc aag tgg         5049
Ile Tyr Ser Ile Phe Gly Met Ala Asn Phe Ala Tyr Val Lys Trp
1670                1675                1680 gag gct ggc atc gac gac atg ttc aac ttc cag acc ttc gcc aac         5094
Glu Ala Gly Ile Asp Asp Met Phe Asn Phe Gln Thr Phe Ala Asn
    1685                1690                1695 agc atg ctg tgc ctc ttc cag atc acc acg tcg gcc ggc tgg gat         5139
Ser Met Leu Cys Leu Phe Gln Ile Thr Thr Ser Ala Gly Trp Asp
1700                1705                1710 ggc ctc ctc agc ccc atc ctc aac act ggg ccg ccc tac tgc gac         5184
Gly Leu Leu Ser Pro Ile Leu Asn Thr Gly Pro Pro Tyr Cys Asp
    1715                1720                1725 ccc act ctg ccc aac agc aat ggc tct cgg ggg gac tgc ggg agc         5229
Pro Thr Leu Pro Asn Ser Asn Gly Ser Arg Gly Asp Cys Gly Ser
1730                1735                1740 cca gcc gtg ggc atc ctc ttc acc acc tac atc atc atc tcc             5274
Pro Ala Val Gly Ile Leu Phe Thr Thr Tyr Ile Ile Ile Ser
    1745                1750                1755 ttc ctc atc gtg gtc aac atg tac att gcc atc atc ctg gag aac         5319
Phe Leu Ile Val Val Asn Met Tyr Ile Ala Ile Ile Leu Glu Asn
1760                1765                1770 ttc agc gtg gcc acg gag gag agc acc gag ccc ctg agt gag gac         5364
Phe Ser Val Ala Thr Glu Glu Ser Thr Glu Pro Leu Ser Glu Asp
    1775                1780                1785 gac ttc gat atg ttc tat gag atc tgg gag aaa ttt gac cca gag         5409
Asp Phe Asp Met Phe Tyr Glu Ile Trp Glu Lys Phe Asp Pro Glu
1790                1795                1800 gcc act cag ttt att gag tat tcg gtc ctg tct gac ttt gcc gat         5454
Ala Thr Gln Phe Ile Glu Tyr Ser Val Leu Ser Asp Phe Ala Asp
    1805                1810                1815 gcc ctg tct gag cca ctc cgt atc gcc aag ccc aac cag ata agc         5499
Ala Leu Ser Glu Pro Leu Arg Ile Ala Lys Pro Asn Gln Ile Ser
1820                1825                1830 ctc atc aac atg gac ctg ccc atg gtg agt ggg gac cgc atc cat         5544
Leu Ile Asn Met Asp Leu Pro Met Val Ser Gly Asp Arg Ile His
    1835                1840                1845
```

```
tgc atg gac att ctc ttt gcc ttc acc aaa agg gtc ctg ggg gag         5589
Cys Met Asp Ile Leu Phe Ala Phe Thr Lys Arg Val Leu Gly Glu
    1850                1855                1860 tct ggg gag atg gac gcc ctg aag atc cag atg gag gag aag ttc         5634
Ser Gly Glu Met Asp Ala Leu Lys Ile Gln Met Glu Glu Lys Phe
1865                1870                1875 atg gca gcc aac cca tcc aag atc tcc tac gag ccc atc acc acc         5679
Met Ala Ala Asn Pro Ser Lys Ile Ser Tyr Glu Pro Ile Thr Thr
    1880                1885                1890 aca ctc cgg cgc aag cac gaa gag gtg tcg gcc atg gtt atc cag         5724
Thr Leu Arg Arg Lys His Glu Glu Val Ser Ala Met Val Ile Gln
1895                1900                1905 aga gcc ttc cgc agg cac ctg ctg caa cgc tct ttg aag cat gcc         5769
Arg Ala Phe Arg Arg His Leu Leu Gln Arg Ser Leu Lys His Ala
    1910                1915                1920 tcc ttc ctc ttc cgt cag cag gcg ggc agc ggc ctc tcc gaa gag         5814
Ser Phe Leu Phe Arg Gln Gln Ala Gly Ser Gly Leu Ser Glu Glu
1925                1930                1935 gat gcc cct gag cga gag ggc ctc atc gcc tac gtg atg agt gag         5859
Asp Ala Pro Glu Arg Glu Gly Leu Ile Ala Tyr Val Met Ser Glu
    1940                1945                1950 aac ttc tcc cga ccc ctt ggc cca ccc tcc agc tcc tcc atc tcc         5904
Asn Phe Ser Arg Pro Leu Gly Pro Pro Ser Ser Ser Ser Ile Ser
1955                1960                1965 tcc act tcc ttc cca ccc tcc tat gac agt gtc act aga gcc acc         5949
Ser Thr Ser Phe Pro Pro Ser Tyr Asp Ser Val Thr Arg Ala Thr
    1970                1975                1980 agc gat aac ctc cag gtg cgg ggg tct gac tac agc cac agt gaa         5994
Ser Asp Asn Leu Gln Val Arg Gly Ser Asp Tyr Ser His Ser Glu
1985                1990                1995 gat ctc gcc gac ttc ccc cct tct ccg gac agg gac cgt gag tcc         6039
Asp Leu Ala Asp Phe Pro Pro Ser Pro Asp Arg Asp Arg Glu Ser
    2000                2005                2010 atc gtg tgagcctcgg cctggctggc caggacacac tgaaaagcag ccttttcac       6095
Ile Val
    2015 catggcaaac ctaaatgcag tcagtcamaa accagcctgg ggccttcctg gctttgggag   6155
taagaaatgg gcct                                                     6169

<210> SEQ ID NO 6
<211> LENGTH: 2015
<212> TYPE: PRT
<213> ORGANISM: Homo sapiens

<400> SEQUENCE: 6

Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
```

-continued

```
                100                 105                 110
Val Leu Ser Pro Phe His Pro Ile Arg Arg Ala Ala Val Lys Ile Leu
            115                 120                 125
Val His Ser Leu Phe Asn Met Leu Ile Met Cys Thr Ile Leu Thr Asn
            130                 135                 140
Cys Val Phe Met Ala Gln His Asp Pro Pro Trp Thr Lys Tyr Val
145                 150                 155                 160
Glu Tyr Thr Phe Thr Ala Ile Tyr Thr Phe Glu Ser Leu Val Lys Ile
                165                 170                 175
Leu Ala Arg Gly Phe Cys Leu His Ala Phe Thr Phe Leu Arg Asp Pro
            180                 185                 190
Trp Asn Trp Leu Asp Phe Ser Val Ile Ile Met Ala Tyr Thr Thr Glu
            195                 200                 205
Phe Val Asp Leu Gly Asn Val Ser Ala Leu Arg Thr Phe Arg Val Leu
            210                 215                 220
Arg Ala Leu Lys Thr Ile Ser Val Ile Ser Gly Leu Lys Thr Ile Val
225                 230                 235                 240
Gly Ala Leu Ile Gln Ser Val Lys Lys Leu Ala Asp Val Met Val Leu
                245                 250                 255
Thr Val Phe Cys Leu Ser Val Phe Ala Leu Ile Gly Leu Gln Leu Phe
            260                 265                 270
Met Gly Asn Leu Arg His Lys Cys Val Arg Asn Phe Thr Ala Leu Asn
            275                 280                 285
Gly Thr Asn Gly Ser Val Glu Ala Asp Gly Leu Val Trp Glu Ser Leu
            290                 295                 300
Asp Leu Tyr Leu Ser Asp Pro Glu Asn Tyr Leu Leu Lys Asn Gly Thr
305                 310                 315                 320
Ser Asp Val Leu Leu Cys Gly Asn Ser Ser Asp Ala Gly Thr Cys Pro
                325                 330                 335
Glu Gly Tyr Arg Cys Leu Lys Ala Gly Glu Asn Pro Asp His Gly Tyr
            340                 345                 350
Thr Ser Phe Asp Ser Phe Ala Trp Ala Phe Leu Ala Leu Phe Arg Leu
            355                 360                 365
Met Thr Gln Asp Cys Trp Glu Arg Leu Tyr Gln Gln Thr Leu Arg Ser
            370                 375                 380
Ala Gly Lys Ile Tyr Met Ile Phe Phe Met Leu Val Ile Phe Leu Gly
385                 390                 395                 400
Ser Phe Tyr Leu Val Asn Leu Ile Leu Ala Val Val Ala Met Ala Tyr
                405                 410                 415
Glu Glu Gln Asn Gln Ala Thr Ile Ala Glu Thr Glu Glu Lys Glu Lys
            420                 425                 430
Arg Phe Gln Glu Ala Met Glu Met Leu Lys Lys Glu His Glu Ala Leu
            435                 440                 445
Thr Ile Arg Gly Val Asp Thr Val Ser Arg Ser Ser Leu Glu Met Ser
            450                 455                 460
Pro Leu Ala Pro Val Asn Ser His Glu Arg Arg Ser Lys Arg Arg Lys
465                 470                 475                 480
Arg Met Ser Ser Gly Thr Glu Glu Cys Gly Glu Asp Arg Leu Pro Lys
                485                 490                 495
Ser Asp Ser Glu Asp Gly Pro Arg Ala Met Asn His Leu Ser Leu Thr
            500                 505                 510
Arg Gly Leu Ser Arg Thr Ser Met Lys Pro Arg Ser Ser Arg Gly Ser
            515                 520                 525
```

-continued

```
Ile Phe Thr Phe Arg Arg Arg Asp Leu Gly Ser Glu Ala Asp Phe Ala
        530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
            565                 570                 575

Ser Pro Gly Thr Ser Ala Pro Gly His Ala Leu His Gly Lys Lys Asn
                580                 585                 590

Ser Thr Val Asp Cys Asn Gly Val Val Ser Leu Leu Gly Ala Gly Asp
            595                 600                 605

Pro Glu Ala Thr Ser Pro Gly Ser His Leu Leu Arg Pro Val Met Leu
        610                 615                 620

Glu His Pro Pro Asp Thr Thr Pro Ser Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
    930                 935                 940
```

```
Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln Leu Pro Ser Cys Ile Ala Thr Pro
        995                 1000                1005

Tyr Ser Pro Pro Pro Glu Thr Glu Lys Val Pro Pro Thr Arg
1010                1015                1020

Lys Glu Thr Arg Phe Glu Glu Gly Glu Gln Pro Gln Gly Thr
1025                1030                1035

Pro Gly Asp Pro Glu Pro Val Cys Val Pro Ile Ala Val Ala Glu
1040                1045                1050

Ser Asp Thr Asp Asp Gln Glu Glu Asp Glu Glu Asn Ser Leu Gly
1055                1060                1065

Thr Glu Glu Glu Ser Ser Lys Gln Glu Ser Gln Pro Val Ser Gly
1070                1075                1080

Gly Pro Glu Ala Pro Pro Asp Ser Arg Thr Trp Ser Gln Val Ser
1085                1090                1095

Ala Thr Ala Ser Ser Glu Ala Glu Ala Ser Ala Ser Gln Ala Asp
1100                1105                1110

Trp Arg Gln Gln Trp Lys Ala Glu Pro Gln Ala Pro Gly Cys Gly
1115                1120                1125

Glu Thr Pro Glu Asp Ser Cys Ser Glu Gly Ser Thr Ala Asp Met
1130                1135                1140

Thr Asn Thr Ala Glu Leu Leu Glu Gln Ile Pro Asp Leu Gly Gln
1145                1150                1155

Asp Val Lys Asp Pro Glu Asp Cys Phe Thr Glu Gly Cys Val Arg
1160                1165                1170

Arg Cys Pro Cys Cys Ala Val Asp Thr Thr Gln Ala Pro Gly Lys
1175                1180                1185

Val Trp Trp Arg Leu Arg Lys Thr Cys Tyr His Ile Val Glu His
1190                1195                1200

Ser Trp Phe Glu Thr Phe Ile Ile Phe Met Ile Leu Leu Ser Ser
1205                1210                1215

Gly Ala Leu Ala Phe Glu Asp Ile Tyr Leu Glu Glu Arg Lys Thr
1220                1225                1230

Ile Lys Val Leu Leu Glu Tyr Ala Asp Lys Met Phe Thr Tyr Val
1235                1240                1245

Phe Val Leu Glu Met Leu Leu Lys Trp Val Ala Tyr Gly Phe Lys
1250                1255                1260

Lys Tyr Phe Thr Asn Ala Trp Cys Trp Leu Asp Phe Leu Ile Val
1265                1270                1275

Asp Val Ser Leu Val Ser Leu Val Ala Asn Thr Leu Gly Phe Ala
1280                1285                1290

Glu Met Gly Pro Ile Lys Ser Leu Arg Thr Leu Arg Ala Leu Arg
1295                1300                1305

Pro Leu Arg Ala Leu Ser Arg Phe Glu Gly Met Arg Val Val Val
1310                1315                1320

Asn Ala Leu Val Gly Ala Ile Pro Ser Ile Met Asn Val Leu Leu
1325                1330                1335

Val Cys Leu Ile Phe Trp Leu Ile Phe Ser Ile Met Gly Val Asn
```

-continued

```
          1340                1345                1350

Leu Phe Ala Gly Lys Phe Gly Arg Cys Ile Asn Gln Thr Glu Gly
    1355                1360                1365

Asp Leu Pro Leu Asn Tyr Thr Ile Val Asn Asn Lys Ser Gln Cys
    1370                1375                1380

Glu Ser Leu Asn Leu Thr Gly Glu Leu Tyr Trp Thr Lys Val Lys
    1385                1390                1395

Val Asn Phe Asp Asn Val Gly Ala Gly Tyr Leu Ala Leu Leu Gln
    1400                1405                1410

Val Ala Thr Phe Lys Gly Trp Met Asp Ile Met Tyr Ala Ala Val
    1415                1420                1425

Asp Ser Arg Gly Tyr Glu Glu Gln Pro Gln Trp Glu Tyr Asn Leu
    1430                1435                1440

Tyr Met Tyr Ile Tyr Phe Val Ile Phe Ile Ile Phe Gly Ser Phe
    1445                1450                1455

Phe Thr Leu Asn Leu Phe Ile Gly Val Ile Ile Asp Asn Phe Asn
    1460                1465                1470

Gln Gln Lys Lys Lys Leu Gly Gly Gln Asp Ile Phe Met Thr Glu
    1475                1480                1485

Glu Gln Lys Lys Tyr Tyr Asn Ala Met Lys Lys Leu Gly Ser Lys
    1490                1495                1500

Lys Pro Gln Lys Pro Ile Pro Arg Pro Leu Asn Lys Tyr Gln Gly
    1505                1510                1515

Phe Ile Phe Asp Ile Val Thr Lys Gln Ala Phe Asp Val Thr Ile
    1520                1525                1530

Met Phe Leu Ile Cys Leu Asn Met Val Thr Met Met Val Glu Thr
    1535                1540                1545

Asp Asp Gln Ser Pro Glu Lys Ile Asn Ile Leu Ala Lys Ile Asn
    1550                1555                1560

Leu Leu Phe Val Ala Ile Phe Thr Gly Glu Cys Ile Val Lys Leu
    1565                1570                1575

Ala Ala Leu Arg His Tyr Tyr Phe Thr Asn Ser Trp Asn Ile Phe
    1580                1585                1590

Asp Phe Val Val Val Ile Leu Ser Ile Val Gly Thr Val Leu Ser
    1595                1600                1605

Asp Ile Ile Gln Lys Tyr Phe Phe Ser Pro Thr Leu Phe Arg Val
    1610                1615                1620

Ile Arg Leu Ala Arg Ile Gly Arg Ile Leu Arg Leu Ile Arg Gly
    1625                1630                1635

Ala Lys Gly Ile Arg Thr Leu Leu Phe Ala Leu Met Met Ser Leu
    1640                1645                1650

Pro Ala Leu Phe Asn Ile Gly Leu Leu Leu Phe Leu Val Met Phe
    1655                1660                1665

Ile Tyr Ser Ile Phe Gly Met Ala Asn Phe Ala Tyr Val Lys Trp
    1670                1675                1680

Glu Ala Gly Ile Asp Asp Met Phe Asn Phe Gln Thr Phe Ala Asn
    1685                1690                1695

Ser Met Leu Cys Leu Phe Gln Ile Thr Thr Ser Ala Gly Trp Asp
    1700                1705                1710

Gly Leu Leu Ser Pro Ile Leu Asn Thr Gly Pro Pro Tyr Cys Asp
    1715                1720                1725

Pro Thr Leu Pro Asn Ser Asn Gly Ser Arg Gly Asp Cys Gly Ser
    1730                1735                1740
```

```
Pro Ala Val Gly Ile Leu Phe Phe Thr Thr Tyr Ile Ile Ile Ser
    1745                1750                1755

Phe Leu Ile Val Val Asn Met Tyr Ile Ala Ile Ile Leu Glu Asn
    1760                1765                1770

Phe Ser Val Ala Thr Glu Glu Ser Thr Glu Pro Leu Ser Glu Asp
    1775                1780                1785

Asp Phe Asp Met Phe Tyr Glu Ile Trp Glu Lys Phe Asp Pro Glu
    1790                1795                1800

Ala Thr Gln Phe Ile Glu Tyr Ser Val Leu Ser Asp Phe Ala Asp
    1805                1810                1815

Ala Leu Ser Glu Pro Leu Arg Ile Ala Lys Pro Asn Gln Ile Ser
    1820                1825                1830

Leu Ile Asn Met Asp Leu Pro Met Val Ser Gly Asp Arg Ile His
    1835                1840                1845

Cys Met Asp Ile Leu Phe Ala Phe Thr Lys Arg Val Leu Gly Glu
    1850                1855                1860

Ser Gly Glu Met Asp Ala Leu Lys Ile Gln Met Glu Glu Lys Phe
    1865                1870                1875

Met Ala Ala Asn Pro Ser Lys Ile Ser Tyr Glu Pro Ile Thr Thr
    1880                1885                1890

Thr Leu Arg Arg Lys His Glu Glu Val Ser Ala Met Val Ile Gln
    1895                1900                1905

Arg Ala Phe Arg Arg His Leu Leu Gln Arg Ser Leu Lys His Ala
    1910                1915                1920

Ser Phe Leu Phe Arg Gln Gln Ala Gly Ser Gly Leu Ser Glu Glu
    1925                1930                1935

Asp Ala Pro Glu Arg Glu Gly Leu Ile Ala Tyr Val Met Ser Glu
    1940                1945                1950

Asn Phe Ser Arg Pro Leu Gly Pro Pro Ser Ser Ser Ser Ile Ser
    1955                1960                1965

Ser Thr Ser Phe Pro Pro Ser Tyr Asp Ser Val Thr Arg Ala Thr
    1970                1975                1980

Ser Asp Asn Leu Gln Val Arg Gly Ser Asp Tyr Ser His Ser Glu
    1985                1990                1995

Asp Leu Ala Asp Phe Pro Pro Ser Pro Asp Arg Asp Arg Glu Ser
    2000                2005                2010

Ile Val
    2015

<210> SEQ ID NO 7
<211> LENGTH: 6169
<212> TYPE: DNA
<213> ORGANISM: Homo sapiens
<220> FEATURE:
<221> NAME/KEY: CDS
<222> LOCATION: (1)..(6045)

<400> SEQUENCE: 7 atg gca aac ttc cta tta cct agg ggc acc agc agc ttc cgc agg ttc      48
Met Ala Asn Phe Leu Leu Pro Arg Gly Thr Ser Ser Phe Arg Arg Phe
1               5                   10                  15 aca cgg gag tcc ctg gca gcc atc gag aag cgc atg gcg gag aag caa      96
Thr Arg Glu Ser Leu Ala Ala Ile Glu Lys Arg Met Ala Glu Lys Gln
            20                  25                  30 gcc cgc ggc tca acc acc ttg cag gag agc cga gag ggg ctg ccc gag     144
Ala Arg Gly Ser Thr Thr Leu Gln Glu Ser Arg Glu Gly Leu Pro Glu
```

```
              35                  40                  45
gag gag gct ccc cgg ccc cag ctg gac ctg cag gcc tcc aaa aag ctg        192
Glu Glu Ala Pro Arg Pro Gln Leu Asp Leu Gln Ala Ser Lys Lys Leu
     50                  55                  60 cca gat ctc tat ggc aat cca ccc caa gag ctc atc gga gag ccc ctg        240
Pro Asp Leu Tyr Gly Asn Pro Pro Gln Glu Leu Ile Gly Glu Pro Leu
 65                  70                  75                  80 gag gac ctg gac ccc ttc tat agc acc caa aag act ttc atc gta ctg        288
Glu Asp Leu Asp Pro Phe Tyr Ser Thr Gln Lys Thr Phe Ile Val Leu
                     85                  90                  95 aat aaa ggc aag acc atc ttc cgg ttc agt gcc acc aac gcc ttg tat        336
Asn Lys Gly Lys Thr Ile Phe Arg Phe Ser Ala Thr Asn Ala Leu Tyr
                100                 105                 110 gtc ctc agt ccc ttc cac ccc atc cgg aga gcg gct gtg aag att ctg        384
Val Leu Ser Pro Phe His Pro Ile Arg Arg Ala Ala Val Lys Ile Leu
                115                 120                 125 gtt cac tcg ctc ttc aac atg ctc atc atg tgc acc atc ctc acc aac        432
Val His Ser Leu Phe Asn Met Leu Ile Met Cys Thr Ile Leu Thr Asn
            130                 135                 140 tgc gtg ttc atg gcc cag cac gac cct cca ccc tgg acc aag tat gtc        480
Cys Val Phe Met Ala Gln His Asp Pro Pro Pro Trp Thr Lys Tyr Val
145                 150                 155                 160 gag tac acc ttc acc gcc att tac acc ttt gag tct ctg gtc aag att        528
Glu Tyr Thr Phe Thr Ala Ile Tyr Thr Phe Glu Ser Leu Val Lys Ile
                165                 170                 175 ctg gct cga ggc ttc tgc ctg cac gcg ttc act ttc ctt cgg gac cca        576
Leu Ala Arg Gly Phe Cys Leu His Ala Phe Thr Phe Leu Arg Asp Pro
                180                 185                 190 tgg aac tgg ctg gac ttt agt gtg att atc atg gca tac aca act gaa        624
Trp Asn Trp Leu Asp Phe Ser Val Ile Ile Met Ala Tyr Thr Thr Glu
            195                 200                 205 ttt gtg gac ctg ggc aat gtc tca gcc tta cgc acc ttc cga gtc ctc        672
Phe Val Asp Leu Gly Asn Val Ser Ala Leu Arg Thr Phe Arg Val Leu
            210                 215                 220 cgg gcc ctg aaa act ata tca gtc att tca ggg ctg aag acc atc gtg        720
Arg Ala Leu Lys Thr Ile Ser Val Ile Ser Gly Leu Lys Thr Ile Val
225                 230                 235                 240 ggg gcc ctg atc cag tct gtg aag aag ctg gct gat gtg atg gtc ctc        768
Gly Ala Leu Ile Gln Ser Val Lys Lys Leu Ala Asp Val Met Val Leu
                245                 250                 255 aca gtc ttc tgc ctc agc gtc ttt gcc ctc atc ggc ctg cag ctc ttc        816
Thr Val Phe Cys Leu Ser Val Phe Ala Leu Ile Gly Leu Gln Leu Phe
                260                 265                 270 atg ggc aac cta agg cac aag tgc gtg cgc aac ttc aca gcg ctc aac        864
Met Gly Asn Leu Arg His Lys Cys Val Arg Asn Phe Thr Ala Leu Asn
            275                 280                 285 ggc acc aac ggc tcc gtg gag gcc gac ggc ttg gtc tgg gaa tcc ctg        912
Gly Thr Asn Gly Ser Val Glu Ala Asp Gly Leu Val Trp Glu Ser Leu
            290                 295                 300 gac ctt tac ctc agt gat cca gaa aat tac ctg ctc aag aac ggc acc        960
Asp Leu Tyr Leu Ser Asp Pro Glu Asn Tyr Leu Leu Lys Asn Gly Thr
305                 310                 315                 320 tct gat gtg tta ctg tgt ggg aac agc tct gac gct ggg aca tgt ccg       1008
Ser Asp Val Leu Leu Cys Gly Asn Ser Ser Asp Ala Gly Thr Cys Pro
                325                 330                 335 gag ggc tac cgg tgc cta aag gca ggg gag aac ccc gac cac ggc tac       1056
Glu Gly Tyr Arg Cys Leu Lys Ala Gly Glu Asn Pro Asp His Gly Tyr
                340                 345                 350 acc agc ttc gat tcc ttt gcc tgg gcc ttt ctt gca ctc ttc cgc ctg       1104
```

```
                Thr Ser Phe Asp Ser Phe Ala Trp Ala Phe Leu Ala Leu Phe Arg Leu
                            355                 360                 365 atg acg cag gac tgc tgg gag cgc ctc tat cag cag acc ctc agg tcc        1152
Met Thr Gln Asp Cys Trp Glu Arg Leu Tyr Gln Gln Thr Leu Arg Ser
    370                 375                 380 gca ggg aag atc tac atg atc ttc ttc atg ctt gtc atc ttc ctg ggg        1200
Ala Gly Lys Ile Tyr Met Ile Phe Phe Met Leu Val Ile Phe Leu Gly
385                 390                 395                 400 tcc ttc tac ctg gtg aac ctg atc ctg gcc gtg gtc gca atg gcc tat        1248
Ser Phe Tyr Leu Val Asn Leu Ile Leu Ala Val Val Ala Met Ala Tyr
                405                 410                 415 gag gag caa aac caa gcc acc atc gct gag acc gag gag aag gaa aag        1296
Glu Glu Gln Asn Gln Ala Thr Ile Ala Glu Thr Glu Glu Lys Glu Lys
            420                 425                 430 cgc ttc cag gag gcc atg gaa atg ctc aag aaa gaa cac gag gcc ctc        1344
Arg Phe Gln Glu Ala Met Glu Met Leu Lys Lys Glu His Glu Ala Leu
        435                 440                 445 acc atc agg ggt gtg gat acc gtg tcc cgt agc tcc ttg gag atg tcc        1392
Thr Ile Arg Gly Val Asp Thr Val Ser Arg Ser Ser Leu Glu Met Ser
    450                 455                 460 cct ttg gcc cca gta aac agc cat gag aga aga agc aag agg aga aaa        1440
Pro Leu Ala Pro Val Asn Ser His Glu Arg Arg Ser Lys Arg Arg Lys
465                 470                 475                 480 cgg atg tct tca gga act gag gag tgt ggg gag gac agg ctc ccc aag        1488
Arg Met Ser Ser Gly Thr Glu Glu Cys Gly Glu Asp Arg Leu Pro Lys
                485                 490                 495 tct gac tca gaa gat ggt ccc aga gca atg aat cat ctc agc ctc acc        1536
Ser Asp Ser Glu Asp Gly Pro Arg Ala Met Asn His Leu Ser Leu Thr
                500                 505                 510 cgt ggc ctc agc agg act tct atg aag cca cgt tcc agc cgc ggg agc        1584
Arg Gly Leu Ser Arg Thr Ser Met Lys Pro Arg Ser Ser Arg Gly Ser
            515                 520                 525 att ttc acc ttt cgc agg cga gac ctg ggt tct gaa gca gat ttt gca        1632
Ile Phe Thr Phe Arg Arg Arg Asp Leu Gly Ser Glu Ala Asp Phe Ala
        530                 535                 540 gat gat gaa aac agc aca gcg ggg gag agc gag agc cac cgc aca tca        1680
Asp Asp Glu Asn Ser Thr Ala Gly Glu Ser Glu Ser His Arg Thr Ser
545                 550                 555                 560 ctg ctg gtg ccc tgg ccc ctg cgc cgg acc agt gcc cag gga cag ccc        1728
Leu Leu Val Pro Trp Pro Leu Arg Arg Thr Ser Ala Gln Gly Gln Pro
                565                 570                 575 agt ccc gga acc tcg gct cct ggc cac gcc ctc cat ggc aaa aag aac        1776
Ser Pro Gly Thr Ser Ala Pro Gly His Ala Leu His Gly Lys Lys Asn
            580                 585                 590 agc act gtg gac tgc aat ggg gtg gtc tca tta ctg ggg gca ggc gac        1824
Ser Thr Val Asp Cys Asn Gly Val Val Ser Leu Leu Gly Ala Gly Asp
        595                 600                 605 cca gag gcc aca tcc cca gga agc cac ctc ctc cgc cct gtg atg cta        1872
Pro Glu Ala Thr Ser Pro Gly Ser His Leu Leu Arg Pro Val Met Leu
    610                 615                 620 gag cac ccg cca gac acg acc acg cca tcg gag gag cca ggc ggg ccc        1920
Glu His Pro Pro Asp Thr Thr Thr Pro Ser Glu Glu Pro Gly Gly Pro
625                 630                 635                 640 cag atg ctg acc tcc cag gct ccg tgt gta gat ggc ttc gag gag cca        1968
Gln Met Leu Thr Ser Gln Ala Pro Cys Val Asp Gly Phe Glu Glu Pro
                645                 650                 655 gga gca cgg cag cgg gcc ctc agc gca gtc agc gtc ctc acc agc gca        2016
Gly Ala Arg Gln Arg Ala Leu Ser Ala Val Ser Val Leu Thr Ser Ala
                660                 665                 670
```

```
ctg gaa gag tta gag gag tct cgc cac aag tgt cca cca tgc tgg aac    2064
Leu Glu Glu Leu Glu Glu Ser Arg His Lys Cys Pro Pro Cys Trp Asn
            675                 680                 685 cgt ctc gcc cag cgc tac ctg atc tgg gag tgc tgc ccg ctg tgg atg    2112
Arg Leu Ala Gln Arg Tyr Leu Ile Trp Glu Cys Cys Pro Leu Trp Met
        690                 695                 700 tcc atc aag cag gga gtg aag ttg gtg gtc atg gac ccg ttt act gac    2160
Ser Ile Lys Gln Gly Val Lys Leu Val Val Met Asp Pro Phe Thr Asp
705                 710                 715                 720 ctc acc atc act atg tgc atc gta ctc aac aca ctc ttc atg gcg ctg    2208
Leu Thr Ile Thr Met Cys Ile Val Leu Asn Thr Leu Phe Met Ala Leu
                725                 730                 735 gag cac tac aac atg aca agt gaa ttc gag gag atg ctg cag gtc gga    2256
Glu His Tyr Asn Met Thr Ser Glu Phe Glu Glu Met Leu Gln Val Gly
            740                 745                 750 aac ctg gtc ttc aca ggg att ttc aca gca gag atg acc ttc aag atc    2304
Asn Leu Val Phe Thr Gly Ile Phe Thr Ala Glu Met Thr Phe Lys Ile
        755                 760                 765 att gcc ctc gac ccc tac tac tac ttc caa cag ggc tgg aac atc ttc    2352
Ile Ala Leu Asp Pro Tyr Tyr Tyr Phe Gln Gln Gly Trp Asn Ile Phe
770                 775                 780 gac agc atc atc gtc atc ctt agc ctc atg gag ctg ggc ctg tcc cgc    2400
Asp Ser Ile Ile Val Ile Leu Ser Leu Met Glu Leu Gly Leu Ser Arg
785                 790                 795                 800 atg agc aac ttg tcg gtg ctg cgc tcc ttc cgc ctg ctg cgg gtc ttc    2448
Met Ser Asn Leu Ser Val Leu Arg Ser Phe Arg Leu Leu Arg Val Phe
                805                 810                 815 aag ctg gcc aaa tca tgg ccc acc ctg aac aca ctc atc aag atc atc    2496
Lys Leu Ala Lys Ser Trp Pro Thr Leu Asn Thr Leu Ile Lys Ile Ile
            820                 825                 830 ggg aac tca gtg ggg gca ctg ggg aac ctg aca ctg gtg cta gcc atc    2544
Gly Asn Ser Val Gly Ala Leu Gly Asn Leu Thr Leu Val Leu Ala Ile
        835                 840                 845 atc gtg ttc atc ttt gct gtg gtg ggc atg cag ctc ttt ggc aag aac    2592
Ile Val Phe Ile Phe Ala Val Val Gly Met Gln Leu Phe Gly Lys Asn
850                 855                 860 tac tcg gag ctg agg gac agc gac tca ggc ctg ctg cct cgc tgg cac    2640
Tyr Ser Glu Leu Arg Asp Ser Asp Ser Gly Leu Leu Pro Arg Trp His
865                 870                 875                 880 atg atg gac ttc ttt cat gcc ttc ctc atc atc ttc cgc atc ctc tgt    2688
Met Met Asp Phe Phe His Ala Phe Leu Ile Ile Phe Arg Ile Leu Cys
                885                 890                 895 gga gag tgg atc gag acc atg tgg gac tgc atg gag gtg tcg ggg cag    2736
Gly Glu Trp Ile Glu Thr Met Trp Asp Cys Met Glu Val Ser Gly Gln
            900                 905                 910 tca tta tgc ctg ctg gtc ttc ttg ctt gtt atg gtc att ggc aac ctt    2784
Ser Leu Cys Leu Leu Val Phe Leu Leu Val Met Val Ile Gly Asn Leu
        915                 920                 925 gtg gtc ctg aat ctc ttc ctg gcc ttg ctg ctc agc tcc ttc agt gca    2832
Val Val Leu Asn Leu Phe Leu Ala Leu Leu Leu Ser Ser Phe Ser Ala
930                 935                 940 gac aac ctc aca gcc cct gat gag gac aga gag atg aac aac ctc cag    2880
Asp Asn Leu Thr Ala Pro Asp Glu Asp Arg Glu Met Asn Asn Leu Gln
945                 950                 955                 960 ctg gcc ctg gcc cgc atc cag agg ggc ctg cgc ttt gtc aag cgg acc    2928
Leu Ala Leu Ala Arg Ile Gln Arg Gly Leu Arg Phe Val Lys Arg Thr
                965                 970                 975 acc tgg gat ttc tgc tgt ggt ctc ctg cgg cag cgg cct cag aag ccc    2976
Thr Trp Asp Phe Cys Cys Gly Leu Leu Arg Gln Arg Pro Gln Lys Pro
            980                 985                 990
```

```
gca gcc ctt gcc gcc cag ggc cag ctg ccc agc tgc att gcc acc ccc    3024
Ala Ala Leu Ala Ala Gln Gly Gln Leu Pro Ser Cys Ile Ala Thr Pro
        995                 1000                1005 tac tcc ccg cca ccc cca gag acg gag aag gtg cct ccc acc cgc        3069
Tyr Ser Pro Pro Pro Pro Glu Thr Glu Lys Val Pro Pro Thr Arg
    1010                1015                1020 aag gaa aca cgg ttt gag gaa ggc gag caa cca ggc cag ggc acc        3114
Lys Glu Thr Arg Phe Glu Glu Gly Glu Gln Pro Gly Gln Gly Thr
1025                1030                1035 ccc ggg gat cca gag ccc gtg tgt gtg ccc atc gct gtg gcc gag        3159
Pro Gly Asp Pro Glu Pro Val Cys Val Pro Ile Ala Val Ala Glu
    1040                1045                1050 tca gac aca gat gac caa gaa gaa gat gag gag aac agc ctg ggc        3204
Ser Asp Thr Asp Asp Gln Glu Glu Asp Glu Glu Asn Ser Leu Gly
1055                1060                1065 acg gag gag gag tcc agc aag cag gaa tcc cag cct gtg tcc ggt        3249
Thr Glu Glu Glu Ser Ser Lys Gln Glu Ser Gln Pro Val Ser Gly
    1070                1075                1080 ggc cca gag gcc cct ccg gat tcc agg acc tgg agc cag gtg tca        3294
Gly Pro Glu Ala Pro Pro Asp Ser Arg Thr Trp Ser Gln Val Ser
1085                1090                1095 gcg act gcc tcc tct gag gcc gag gcc agt gca tct cag gcc gac        3339
Ala Thr Ala Ser Ser Glu Ala Glu Ala Ser Ala Ser Gln Ala Asp
    1100                1105                1110 tgg cgg cag cag tgg aaa gcg gaa ccc cag gcc cca ggg tgc ggt        3384
Trp Arg Gln Gln Trp Lys Ala Glu Pro Gln Ala Pro Gly Cys Gly
1115                1120                1125 gag acc cca gag gac agt tgc tcc gag ggc agc aca gca gac atg        3429
Glu Thr Pro Glu Asp Ser Cys Ser Glu Gly Ser Thr Ala Asp Met
    1130                1135                1140 acc aac acc gct gag ctc ctg gag cag atc cct gac ctc ggc cag        3474
Thr Asn Thr Ala Glu Leu Leu Glu Gln Ile Pro Asp Leu Gly Gln
1145                1150                1155 gat gtc aag gac cca gag gac tgc ttc act gaa ggc tgt gtc cgg        3519
Asp Val Lys Asp Pro Glu Asp Cys Phe Thr Glu Gly Cys Val Arg
    1160                1165                1170 cgc tgt ccc tgc tgt gcg gtg gac acc aca cag gcc cca ggg aag        3564
Arg Cys Pro Cys Cys Ala Val Asp Thr Thr Gln Ala Pro Gly Lys
1175                1180                1185 gtc tgg tgg cgg ttg cgc aag acc tgc tac cac atc gtg gag cac        3609
Val Trp Trp Arg Leu Arg Lys Thr Cys Tyr His Ile Val Glu His
    1190                1195                1200 agc tgg ttc gag aca ttc atc atc ttc atg atc cta ctc agc agt        3654
Ser Trp Phe Glu Thr Phe Ile Ile Phe Met Ile Leu Leu Ser Ser
1205                1210                1215 gga gcg ctg gcc ttc gag gac atc tac cta gag gag cgg aag acc        3699
Gly Ala Leu Ala Phe Glu Asp Ile Tyr Leu Glu Glu Arg Lys Thr
    1220                1225                1230 atc aag gtt ctg ctt gag tat gcc gac aag atg ttc aca tat gtc        3744
Ile Lys Val Leu Leu Glu Tyr Ala Asp Lys Met Phe Thr Tyr Val
1235                1240                1245 ttc gtg ctg gag atg ctg ctc aag tgg gtg gcc tac ggc ttc aag        3789
Phe Val Leu Glu Met Leu Leu Lys Trp Val Ala Tyr Gly Phe Lys
    1250                1255                1260 aag tac ttc acc aat gcc tgg tgc tgg ctc gac ttc ctc atc gta        3834
Lys Tyr Phe Thr Asn Ala Trp Cys Trp Leu Asp Phe Leu Ile Val
1265                1270                1275 gac gtc tct ctg gtc agc ctg gtg gcc aac acc ctg ggc ttt gcc        3879
Asp Val Ser Leu Val Ser Leu Val Ala Asn Thr Leu Gly Phe Ala
```

```
                        1280                1285                1290
gag atg ggt ccc atc aag tca ctg cgg acg ctg cgt gca ctc cgt        3924
Glu Met Gly Pro Ile Lys Ser Leu Arg Thr Leu Arg Ala Leu Arg
        1295                1300                1305 cct ctg aga gct ctg tca cga ttt gag ggc atg agg gtg gtg gtc        3969
Pro Leu Arg Ala Leu Ser Arg Phe Glu Gly Met Arg Val Val Val
        1310                1315                1320 aat gcc ctg gtg ggc gcc atc ccg tcc atc atg aac gtc ctc ctc        4014
Asn Ala Leu Val Gly Ala Ile Pro Ser Ile Met Asn Val Leu Leu
        1325                1330                1335 gtc tgc ctc atc ttc tgg ctc atc ttc agc atc atg ggc gtg aac        4059
Val Cys Leu Ile Phe Trp Leu Ile Phe Ser Ile Met Gly Val Asn
        1340                1345                1350 ctc ttt gcg ggg aag ttt ggg agg tgc atc aac cag aca gag gga        4104
Leu Phe Ala Gly Lys Phe Gly Arg Cys Ile Asn Gln Thr Glu Gly
        1355                1360                1365 gac ttg cct ttg aac tac acc atc gtg aac aac aag agc cag tgt        4149
Asp Leu Pro Leu Asn Tyr Thr Ile Val Asn Asn Lys Ser Gln Cys
        1370                1375                1380 gag tcc ttg aac ttg acc gga gaa ttg tac tgg acc aag gtg aaa        4194
Glu Ser Leu Asn Leu Thr Gly Glu Leu Tyr Trp Thr Lys Val Lys
        1385                1390                1395 gtc aac ttt gac aac gtg ggg gcc ggg tac ctg gcc ctt ctg cag        4239
Val Asn Phe Asp Asn Val Gly Ala Gly Tyr Leu Ala Leu Leu Gln
        1400                1405                1410 gtg gca aca ttt aaa ggc tgg atg gac att atg tat gca gct gtg        4284
Val Ala Thr Phe Lys Gly Trp Met Asp Ile Met Tyr Ala Ala Val
        1415                1420                1425 gac tcc agg ggg tat gaa gag cag cct cag tgg gaa tac aac ctc        4329
Asp Ser Arg Gly Tyr Glu Glu Gln Pro Gln Trp Glu Tyr Asn Leu
        1430                1435                1440 tac atg tac atc tat ttt gtc att ttc atc atc ttt ggg tct ttc        4374
Tyr Met Tyr Ile Tyr Phe Val Ile Phe Ile Ile Phe Gly Ser Phe
        1445                1450                1455 ttc acc ctg aac ctc ttt att ggt gtc atc att gac aac ttc aac        4419
Phe Thr Leu Asn Leu Phe Ile Gly Val Ile Ile Asp Asn Phe Asn
        1460                1465                1470 caa cag aag aaa aag tta ggg ggc cag gac atc ttc atg aca gag        4464
Gln Gln Lys Lys Lys Leu Gly Gly Gln Asp Ile Phe Met Thr Glu
        1475                1480                1485 gag cag aag aag tac tac aat gcc atg aag aag ctg ggc tcc aag        4509
Glu Gln Lys Lys Tyr Tyr Asn Ala Met Lys Lys Leu Gly Ser Lys
        1490                1495                1500 aag ccc cag aag ccc atc cca cgg ccc ctg aac aag tac cag ggc        4554
Lys Pro Gln Lys Pro Ile Pro Arg Pro Leu Asn Lys Tyr Gln Gly
        1505                1510                1515 ttc ata ttc gac att gtg acc aag cag gcc ttt gac gtc acc atc        4599
Phe Ile Phe Asp Ile Val Thr Lys Gln Ala Phe Asp Val Thr Ile
        1520                1525                1530 atg ttt ctg atc tgc ttg aat atg gtg acc atg atg gtg gag aca        4644
Met Phe Leu Ile Cys Leu Asn Met Val Thr Met Met Val Glu Thr
        1535                1540                1545 gat gac caa agt cct gag aaa atc aac atc ttg gcc aag atc aac        4689
Asp Asp Gln Ser Pro Glu Lys Ile Asn Ile Leu Ala Lys Ile Asn
        1550                1555                1560 ctg ctc ttt gtg gcc atc ttc aca ggc gag tgt att gtc aag ctg        4734
Leu Leu Phe Val Ala Ile Phe Thr Gly Glu Cys Ile Val Lys Leu
        1565                1570                1575 gct gcc ctg cgc cac tac tac ttc acc aac agc tgg aat atc ttc        4779
```

|     |     |     |     |     |     |     |     |     |     |     |     |     |     |      |
| --- | --- | --- | --- | --- | --- | --- | --- | --- | --- | --- | --- | --- | --- | ---- |
| Ala | Ala | Leu | Arg | His | Tyr | Tyr | Phe | Thr | Asn | Ser | Trp | Asn | Ile | Phe  |
| 1580 |    |    |    |    | 1585 |    |    |    |    | 1590 |    |    |    |      |

| gac | ttc | gtg | gtt | gtc | atc | ctc | tcc | atc | gtg | ggc | act | gtg | ctc | tcg | 4824 |
| --- | --- | --- | --- | --- | --- | --- | --- | --- | --- | --- | --- | --- | --- | --- | ---- |
| Asp | Phe | Val | Val | Val | Ile | Leu | Ser | Ile | Val | Gly | Thr | Val | Leu | Ser |      |
| 1595 |    |    |    |    | 1600 |    |    |    |    | 1605 |    |    |    |    |      |

| gac | atc | atc | cag | aag | tac | ttc | ttc | tcc | ccg | acg | ctc | ttc | cga | gtc | 4869 |
| --- | --- | --- | --- | --- | --- | --- | --- | --- | --- | --- | --- | --- | --- | --- | ---- |
| Asp | Ile | Ile | Gln | Lys | Tyr | Phe | Phe | Ser | Pro | Thr | Leu | Phe | Arg | Val |      |
| 1610 |    |    |    |    | 1615 |    |    |    |    | 1620 |    |    |    |    |      |

| atc | cgc | ctg | gcc | cga | ata | ggc | cgc | atc | ctc | aga | ctg | atc | cga | ggg | 4914 |
| --- | --- | --- | --- | --- | --- | --- | --- | --- | --- | --- | --- | --- | --- | --- | ---- |
| Ile | Arg | Leu | Ala | Arg | Ile | Gly | Arg | Ile | Leu | Arg | Leu | Ile | Arg | Gly |      |
| 1625 |    |    |    |    | 1630 |    |    |    |    | 1635 |    |    |    |    |      |

| gcc | aag | ggg | atc | cgc | acg | ctg | ctc | ttt | gcc | ctc | atg | atg | tcc | ctg | 4959 |
| --- | --- | --- | --- | --- | --- | --- | --- | --- | --- | --- | --- | --- | --- | --- | ---- |
| Ala | Lys | Gly | Ile | Arg | Thr | Leu | Leu | Phe | Ala | Leu | Met | Met | Ser | Leu |      |
| 1640 |    |    |    |    | 1645 |    |    |    |    | 1650 |    |    |    |    |      |

| cct | gcc | ctc | ttc | aac | atc | ggg | ctg | ctc | ttc | ctc | gtc | atg | ttc | 5004 |
| --- | --- | --- | --- | --- | --- | --- | --- | --- | --- | --- | --- | --- | --- | ---- |
| Pro | Ala | Leu | Phe | Asn | Ile | Gly | Leu | Leu | Phe | Leu | Val | Met | Phe |      |
| 1655 |    |    |    |    | 1660 |    |    |    |    | 1665 |    |    |    |      |

| atc | tac | tcc | atc | ttt | ggc | atg | gcc | aac | ttc | gct | tat | gtc | aag | tgg | 5049 |
| --- | --- | --- | --- | --- | --- | --- | --- | --- | --- | --- | --- | --- | --- | --- | ---- |
| Ile | Tyr | Ser | Ile | Phe | Gly | Met | Ala | Asn | Phe | Ala | Tyr | Val | Lys | Trp |      |
| 1670 |    |    |    |    | 1675 |    |    |    |    | 1680 |    |    |    |    |      |

| gag | gct | ggc | atc | gac | gac | atg | ttc | aac | ttc | cag | acc | ttc | gcc | aac | 5094 |
| --- | --- | --- | --- | --- | --- | --- | --- | --- | --- | --- | --- | --- | --- | --- | ---- |
| Glu | Ala | Gly | Ile | Asp | Asp | Met | Phe | Asn | Phe | Gln | Thr | Phe | Ala | Asn |      |
| 1685 |    |    |    |    | 1690 |    |    |    |    | 1695 |    |    |    |    |      |

| agc | atg | ctg | tgc | ctc | ttc | cag | atc | acc | acg | tcg | gcc | ggc | tgg | gat | 5139 |
| --- | --- | --- | --- | --- | --- | --- | --- | --- | --- | --- | --- | --- | --- | --- | ---- |
| Ser | Met | Leu | Cys | Leu | Phe | Gln | Ile | Thr | Thr | Ser | Ala | Gly | Trp | Asp |      |
| 1700 |    |    |    |    | 1705 |    |    |    |    | 1710 |    |    |    |    |      |

| ggc | ctc | ctc | agc | ccc | atc | ctc | aac | act | ggg | ccg | ccc | tac | tgc | gac | 5184 |
| --- | --- | --- | --- | --- | --- | --- | --- | --- | --- | --- | --- | --- | --- | --- | ---- |
| Gly | Leu | Leu | Ser | Pro | Ile | Leu | Asn | Thr | Gly | Pro | Pro | Tyr | Cys | Asp |      |
| 1715 |    |    |    |    | 1720 |    |    |    |    | 1725 |    |    |    |    |      |

| ccc | act | ctg | ccc | aac | agc | aat | ggc | tct | cgg | ggg | gac | tgc | ggg | agc | 5229 |
| --- | --- | --- | --- | --- | --- | --- | --- | --- | --- | --- | --- | --- | --- | --- | ---- |
| Pro | Thr | Leu | Pro | Asn | Ser | Asn | Gly | Ser | Arg | Gly | Asp | Cys | Gly | Ser |      |
| 1730 |    |    |    |    | 1735 |    |    |    |    | 1740 |    |    |    |    |      |

| cca | gcc | gtg | ggc | atc | ctc | ttc | ttc | acc | acc | tac | atc | atc | atc | tcc | 5274 |
| --- | --- | --- | --- | --- | --- | --- | --- | --- | --- | --- | --- | --- | --- | --- | ---- |
| Pro | Ala | Val | Gly | Ile | Leu | Phe | Phe | Thr | Thr | Tyr | Ile | Ile | Ile | Ser |      |
| 1745 |    |    |    |    | 1750 |    |    |    |    | 1755 |    |    |    |    |      |

| ttc | ctc | atc | gtg | gtc | aac | atg | tac | att | gcc | atc | atc | ctg | gag | aac | 5319 |
| --- | --- | --- | --- | --- | --- | --- | --- | --- | --- | --- | --- | --- | --- | --- | ---- |
| Phe | Leu | Ile | Val | Val | Asn | Met | Tyr | Ile | Ala | Ile | Ile | Leu | Glu | Asn |      |
| 1760 |    |    |    |    | 1765 |    |    |    |    | 1770 |    |    |    |    |      |

| ttc | agc | gtg | gcc | acg | gag | gag | agc | acc | gag | ccc | ctg | agt | gag | gac | 5364 |
| --- | --- | --- | --- | --- | --- | --- | --- | --- | --- | --- | --- | --- | --- | --- | ---- |
| Phe | Ser | Val | Ala | Thr | Glu | Glu | Ser | Thr | Glu | Pro | Leu | Ser | Glu | Asp |      |
| 1775 |    |    |    |    | 1780 |    |    |    |    | 1785 |    |    |    |    |      |

| gac | ttc | gat | atg | ttc | tat | gag | atc | tgg | gag | aaa | ttt | gac | cca | gag | 5409 |
| --- | --- | --- | --- | --- | --- | --- | --- | --- | --- | --- | --- | --- | --- | --- | ---- |
| Asp | Phe | Asp | Met | Phe | Tyr | Glu | Ile | Trp | Glu | Lys | Phe | Asp | Pro | Glu |      |
| 1790 |    |    |    |    | 1795 |    |    |    |    | 1800 |    |    |    |    |      |

| gcc | act | cag | ttt | att | gag | tat | tcg | gtc | ctg | tct | gac | ttt | gcc | gat | 5454 |
| --- | --- | --- | --- | --- | --- | --- | --- | --- | --- | --- | --- | --- | --- | --- | ---- |
| Ala | Thr | Gln | Phe | Ile | Glu | Tyr | Ser | Val | Leu | Ser | Asp | Phe | Ala | Asp |      |
| 1805 |    |    |    |    | 1810 |    |    |    |    | 1815 |    |    |    |    |      |

| gcc | ctg | tct | gag | cca | ctc | cgt | atc | gcc | aag | ccc | aac | cag | ata | agc | 5499 |
| --- | --- | --- | --- | --- | --- | --- | --- | --- | --- | --- | --- | --- | --- | --- | ---- |
| Ala | Leu | Ser | Glu | Pro | Leu | Arg | Ile | Ala | Lys | Pro | Asn | Gln | Ile | Ser |      |
| 1820 |    |    |    |    | 1825 |    |    |    |    | 1830 |    |    |    |    |      |

| ctc | atc | aac | atg | gac | ctg | ccc | atg | gtg | agt | ggg | gac | cgc | atc | cat | 5544 |
| --- | --- | --- | --- | --- | --- | --- | --- | --- | --- | --- | --- | --- | --- | --- | ---- |
| Leu | Ile | Asn | Met | Asp | Leu | Pro | Met | Val | Ser | Gly | Asp | Arg | Ile | His |      |
| 1835 |    |    |    |    | 1840 |    |    |    |    | 1845 |    |    |    |    |      |

| tgc | atg | gac | att | ctc | ttt | gcc | ttc | acc | aaa | agg | gtc | ctg | ggg | gag | 5589 |
| --- | --- | --- | --- | --- | --- | --- | --- | --- | --- | --- | --- | --- | --- | --- | ---- |
| Cys | Met | Asp | Ile | Leu | Phe | Ala | Phe | Thr | Lys | Arg | Val | Leu | Gly | Glu |      |
| 1850 |    |    |    |    | 1855 |    |    |    |    | 1860 |    |    |    |    |      |

| tct | ggg | gag | atg | gac | gcc | ctg | aag | atc | cag | atg | gag | gag | aag | ttc | 5634 |
| --- | --- | --- | --- | --- | --- | --- | --- | --- | --- | --- | --- | --- | --- | --- | ---- |
| Ser | Gly | Glu | Met | Asp | Ala | Leu | Lys | Ile | Gln | Met | Glu | Glu | Lys | Phe |      |
| 1865 |    |    |    |    | 1870 |    |    |    |    | 1875 |    |    |    |    |      |

-continued

| | |
|---|---|
| atg gca gcc aac cca tcc aag atc tcc tac gag ccc atc acc acc<br>Met Ala Ala Asn Pro Ser Lys Ile Ser Tyr Glu Pro Ile Thr Thr<br>1880            1885            1890 | 5679 |
| aca ctc cgg cgc aag cac gaa gag gtg tcg gcc atg gtt atc cag<br>Thr Leu Arg Arg Lys His Glu Glu Val Ser Ala Met Val Ile Gln<br>1895            1900            1905 | 5724 |
| aga gcc ttc cgc agg cac ctg ctg caa cgc tct ttg aag cat gcc<br>Arg Ala Phe Arg Arg His Leu Leu Gln Arg Ser Leu Lys His Ala<br>1910            1915            1920 | 5769 |
| tcc ttc ctc ttc cgt cag cag gcg ggc agc ggc ctc tcc gaa gag<br>Ser Phe Leu Phe Arg Gln Gln Ala Gly Ser Gly Leu Ser Glu Glu<br>1925            1930            1935 | 5814 |
| gat gcc cct gag cga gag ggc ctc atc gcc tac gtg atg agt gag<br>Asp Ala Pro Glu Arg Glu Gly Leu Ile Ala Tyr Val Met Ser Glu<br>1940            1945            1950 | 5859 |
| aac ttc tcc cga ccc ctt ggc cca ccc tcc agc tcc tcc atc tcc<br>Asn Phe Ser Arg Pro Leu Gly Pro Pro Ser Ser Ser Ser Ile Ser<br>1955            1960            1965 | 5904 |
| tcc act tcc ttc cca ccc tcc tat gac agt gtc act aga gcc acc<br>Ser Thr Ser Phe Pro Pro Ser Tyr Asp Ser Val Thr Arg Ala Thr<br>1970            1975            1980 | 5949 |
| agc gat aac ctc cag gtg cgg ggg tct gac tac agc cac agt gaa<br>Ser Asp Asn Leu Gln Val Arg Gly Ser Asp Tyr Ser His Ser Glu<br>1985            1990            1995 | 5994 |
| gat ctc gcc gac ttc ccc cct tct ccg gac agg gac cgt gag tcc<br>Asp Leu Ala Asp Phe Pro Pro Ser Pro Asp Arg Asp Arg Glu Ser<br>2000            2005            2010 | 6039 |
| atc gtg tgagcctcgg cctggctggc caggacacac tgaaaagcag ccttttttcac<br>Ile Val<br>2015 | 6095 |
| catggcaaac ctaaatgcag tcagtcamaa accagcctgg ggccttcctg gctttgggag | 6155 |
| taagaaatgg gcct | 6169 |

<210> SEQ ID NO 8
<211> LENGTH: 2015
<212> TYPE: PRT
<213> ORGANISM: Homo sapiens

<400> SEQUENCE: 8

Met Ala Asn Phe Leu Leu Pro Arg Gly Thr Ser Ser Phe Arg Arg Phe
1                 5                10                15

Thr Arg Glu Ser Leu Ala Ala Ile Glu Lys Arg Met Ala Glu Lys Gln
          20                25                30

Ala Arg Gly Ser Thr Thr Leu Gln Glu Ser Arg Glu Gly Leu Pro Glu
              35              40              45

Glu Glu Ala Pro Arg Pro Gln Leu Asp Leu Gln Ala Ser Lys Lys Leu
    50               55              60

Pro Asp Leu Tyr Gly Asn Pro Pro Gln Glu Leu Ile Gly Glu Pro Leu
65                70              75              80

Glu Asp Leu Asp Pro Phe Tyr Ser Thr Gln Lys Thr Phe Ile Val Leu
                85              90              95

Asn Lys Gly Lys Thr Ile Phe Arg Phe Ser Ala Thr Asn Ala Leu Tyr
             100             105             110

Val Leu Ser Pro Phe His Pro Ile Arg Arg Ala Ala Val Lys Ile Leu
          115              120             125

Val His Ser Leu Phe Asn Met Leu Ile Met Cys Thr Ile Leu Thr Asn
   130              135             140

-continued

```
Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
                260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser Glu Ser His Arg Thr Ser
545                 550                 555                 560

Leu Leu Val Pro Trp Pro Leu Arg Arg Thr Ser Ala Gln Gly Gln Pro
```

```
                565                 570                 575
Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
            595                 600                 605

Pro Glu Ala Thr Ser Pro Gly Ser His Leu Leu Arg Pro Val Met Leu
            610                 615                 620

Glu His Pro Pro Asp Thr Thr Pro Ser Glu Pro Gly Gly Pro
625                 630                 635                 640

Gln Met Leu Thr Ser Gln Ala Pro Cys Val Asp Gly Phe Glu Glu Pro
            645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
            675                 680                 685

Arg Leu Ala Gln Arg Tyr Leu Ile Trp Glu Cys Cys Pro Leu Trp Met
            690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
            725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
            770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
            805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
            850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
            885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Ser Ser Phe Ser Ala
            930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
            980                 985                 990
```

-continued

Ala Ala Leu Ala Ala Gln Gly Gln Leu Pro Ser Cys Ile Ala Thr Pro
        995                 1000                1005

Tyr Ser Pro Pro Pro Glu Thr Glu Lys Val Pro Pro Thr Arg
    1010            1015             1020

Lys Glu Thr Arg Phe Glu Glu Gly Gln Pro Gly Gln Gly Thr
    1025            1030             1035

Pro Gly Asp Pro Glu Pro Val Cys Val Pro Ile Ala Val Ala Glu
    1040             1045              1050

Ser Asp Thr Asp Asp Gln Glu Glu Asp Glu Glu Asn Ser Leu Gly
    1055             1060              1065

Thr Glu Glu Glu Ser Ser Lys Gln Glu Ser Gln Pro Val Ser Gly
    1070            1075             1080

Gly Pro Glu Ala Pro Pro Asp Ser Arg Thr Trp Ser Gln Val Ser
    1085            1090             1095

Ala Thr Ala Ser Ser Glu Ala Glu Ala Ser Ala Ser Gln Ala Asp
    1100             1105              1110

Trp Arg Gln Gln Trp Lys Ala Glu Pro Gln Ala Pro Gly Cys Gly
    1115            1120             1125

Glu Thr Pro Glu Asp Ser Cys Ser Glu Gly Ser Thr Ala Asp Met
    1130            1135             1140

Thr Asn Thr Ala Glu Leu Leu Glu Gln Ile Pro Asp Leu Gly Gln
    1145            1150             1155

Asp Val Lys Asp Pro Glu Asp Cys Phe Thr Glu Gly Cys Val Arg
    1160            1165             1170

Arg Cys Pro Cys Cys Ala Val Asp Thr Thr Gln Ala Pro Gly Lys
    1175            1180             1185

Val Trp Trp Arg Leu Arg Lys Thr Cys Tyr His Ile Val Glu His
    1190            1195             1200

Ser Trp Phe Glu Thr Phe Ile Ile Phe Met Ile Leu Leu Ser Ser
    1205            1210             1215

Gly Ala Leu Ala Phe Glu Asp Ile Tyr Leu Glu Glu Arg Lys Thr
    1220            1225             1230

Ile Lys Val Leu Leu Glu Tyr Ala Asp Lys Met Phe Thr Tyr Val
    1235            1240             1245

Phe Val Leu Glu Met Leu Leu Lys Trp Val Ala Tyr Gly Phe Lys
    1250            1255             1260

Lys Tyr Phe Thr Asn Ala Trp Cys Trp Leu Asp Phe Leu Ile Val
    1265            1270             1275

Asp Val Ser Leu Val Ser Leu Val Ala Asn Thr Leu Gly Phe Ala
    1280            1285             1290

Glu Met Gly Pro Ile Lys Ser Leu Arg Thr Leu Arg Ala Leu Arg
    1295            1300             1305

Pro Leu Arg Ala Leu Ser Arg Phe Glu Gly Met Arg Val Val Val
    1310            1315             1320

Asn Ala Leu Val Gly Ala Ile Pro Ser Ile Met Asn Val Leu Leu
    1325            1330             1335

Val Cys Leu Ile Phe Trp Leu Ile Phe Ser Ile Met Gly Val Asn
    1340            1345             1350

Leu Phe Ala Gly Lys Phe Gly Arg Cys Ile Asn Gln Thr Glu Gly
    1355            1360             1365

Asp Leu Pro Leu Asn Tyr Thr Ile Val Asn Asn Lys Ser Gln Cys
    1370            1375             1380

-continued

Glu Ser Leu Asn Leu Thr Gly Glu Leu Tyr Trp Thr Lys Val Lys
1385            1390            1395

Val Asn Phe Asp Asn Val Gly Ala Gly Tyr Leu Ala Leu Leu Gln
1400            1405            1410

Val Ala Thr Phe Lys Gly Trp Met Asp Ile Met Tyr Ala Ala Val
1415            1420            1425

Asp Ser Arg Gly Tyr Glu Glu Gln Pro Gln Trp Glu Tyr Asn Leu
1430            1435            1440

Tyr Met Tyr Ile Tyr Phe Val Ile Phe Ile Ile Phe Gly Ser Phe
1445            1450            1455

Phe Thr Leu Asn Leu Phe Ile Gly Val Ile Ile Asp Asn Phe Asn
1460            1465            1470

Gln Gln Lys Lys Lys Leu Gly Gly Gln Asp Ile Phe Met Thr Glu
1475            1480            1485

Glu Gln Lys Lys Tyr Tyr Asn Ala Met Lys Lys Leu Gly Ser Lys
1490            1495            1500

Lys Pro Gln Lys Pro Ile Pro Arg Pro Leu Asn Lys Tyr Gln Gly
1505            1510            1515

Phe Ile Phe Asp Ile Val Thr Lys Gln Ala Phe Asp Val Thr Ile
1520            1525            1530

Met Phe Leu Ile Cys Leu Asn Met Val Thr Met Met Val Glu Thr
1535            1540            1545

Asp Asp Gln Ser Pro Glu Lys Ile Asn Ile Leu Ala Lys Ile Asn
1550            1555            1560

Leu Leu Phe Val Ala Ile Phe Thr Gly Glu Cys Ile Val Lys Leu
1565            1570            1575

Ala Ala Leu Arg His Tyr Tyr Phe Thr Asn Ser Trp Asn Ile Phe
1580            1585            1590

Asp Phe Val Val Val Ile Leu Ser Ile Val Gly Thr Val Leu Ser
1595            1600            1605

Asp Ile Ile Gln Lys Tyr Phe Phe Ser Pro Thr Leu Phe Arg Val
1610            1615            1620

Ile Arg Leu Ala Arg Ile Gly Arg Ile Leu Arg Leu Ile Arg Gly
1625            1630            1635

Ala Lys Gly Ile Arg Thr Leu Leu Phe Ala Leu Met Met Ser Leu
1640            1645            1650

Pro Ala Leu Phe Asn Ile Gly Leu Leu Leu Phe Leu Val Met Phe
1655            1660            1665

Ile Tyr Ser Ile Phe Gly Met Ala Asn Phe Ala Tyr Val Lys Trp
1670            1675            1680

Glu Ala Gly Ile Asp Asp Met Phe Asn Phe Gln Thr Phe Ala Asn
1685            1690            1695

Ser Met Leu Cys Leu Phe Gln Ile Thr Thr Ser Ala Gly Trp Asp
1700            1705            1710

Gly Leu Leu Ser Pro Ile Leu Asn Thr Gly Pro Pro Tyr Cys Asp
1715            1720            1725

Pro Thr Leu Pro Asn Ser Asn Gly Ser Arg Gly Asp Cys Gly Ser
1730            1735            1740

Pro Ala Val Gly Ile Leu Phe Phe Thr Thr Tyr Ile Ile Ile Ser
1745            1750            1755

Phe Leu Ile Val Val Asn Met Tyr Ile Ala Ile Ile Leu Glu Asn
1760            1765            1770

Phe Ser Val Ala Thr Glu Glu Ser Thr Glu Pro Leu Ser Glu Asp

```
              1775                1780                1785

Asp Phe Asp Met Phe Tyr Glu Ile Trp Glu Lys Phe Asp Pro Glu
    1790                1795                1800

Ala Thr Gln Phe Ile Glu Tyr Ser Val Leu Ser Asp Phe Ala Asp
    1805                1810                1815

Ala Leu Ser Glu Pro Leu Arg Ile Ala Lys Pro Asn Gln Ile Ser
    1820                1825                1830

Leu Ile Asn Met Asp Leu Pro Met Val Ser Gly Asp Arg Ile His
    1835                1840                1845

Cys Met Asp Ile Leu Phe Ala Phe Thr Lys Arg Val Leu Gly Glu
    1850                1855                1860

Ser Gly Glu Met Asp Ala Leu Lys Ile Gln Met Glu Glu Lys Phe
    1865                1870                1875

Met Ala Ala Asn Pro Ser Lys Ile Ser Tyr Glu Pro Ile Thr Thr
    1880                1885                1890

Thr Leu Arg Arg Lys His Glu Glu Val Ser Ala Met Val Ile Gln
    1895                1900                1905

Arg Ala Phe Arg Arg His Leu Leu Gln Arg Ser Leu Lys His Ala
    1910                1915                1920

Ser Phe Leu Phe Arg Gln Gln Ala Gly Ser Gly Leu Ser Glu Glu
    1925                1930                1935

Asp Ala Pro Glu Arg Glu Gly Leu Ile Ala Tyr Val Met Ser Glu
    1940                1945                1950

Asn Phe Ser Arg Pro Leu Gly Pro Pro Ser Ser Ser Ile Ser
    1955                1960                1965

Ser Thr Ser Phe Pro Pro Ser Tyr Asp Ser Val Thr Arg Ala Thr
    1970                1975                1980

Ser Asp Asn Leu Gln Val Arg Gly Ser Asp Tyr Ser His Ser Glu
    1985                1990                1995

Asp Leu Ala Asp Phe Pro Pro Ser Pro Asp Arg Asp Arg Glu Ser
    2000                2005                2010

Ile Val
    2015

<210> SEQ ID NO 9
<211> LENGTH: 23
<212> TYPE: DNA
<213> ORGANISM: Artificial
<220> FEATURE:
<223> OTHER INFORMATION: PCR primer

<400> SEQUENCE: 9
gccagtggct caaaagacag gct                                            23

<210> SEQ ID NO 10
<211> LENGTH: 21
<212> TYPE: DNA
<213> ORGANISM: Artificial
<220> FEATURE:
<223> OTHER INFORMATION: PCR primer

<400> SEQUENCE: 10
cctgggcact ggtccggcgc a                                              21

<210> SEQ ID NO 11
<211> LENGTH: 22
<212> TYPE: DNA
<213> ORGANISM: Artificial
```

-continued

```
<220> FEATURE:
<223> OTHER INFORMATION: PCR primer

<400> SEQUENCE: 11
caccacacat cactgctggt gc                                              22

<210> SEQ ID NO 12
<211> LENGTH: 24
<212> TYPE: DNA
<213> ORGANISM: Artificial
<220> FEATURE:
<223> OTHER INFORMATION: PCR primer

<400> SEQUENCE: 12
ggaactgctg atcagtttgg gaga                                            24

<210> SEQ ID NO 13
<211> LENGTH: 22
<212> TYPE: DNA
<213> ORGANISM: Artificial
<220> FEATURE:
<223> OTHER INFORMATION: PCR primer

<400> SEQUENCE: 13
gcccagggcc agctgcccag ct                                              22

<210> SEQ ID NO 14
<211> LENGTH: 26
<212> TYPE: DNA
<213> ORGANISM: Artificial
<220> FEATURE:
<223> OTHER INFORMATION: PCR primer

<400> SEQUENCE: 14
ctgtatatgt aggtgcctta tacatg                                          26

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
ccaagaagag gatgaggaga                                                 20

<210> SEQ ID NO 16
<211> LENGTH: 18
<212> TYPE: DNA
<213> ORGANISM: Artificial
<220> FEATURE:
<223> OTHER INFORMATION: PCR primer

<400> SEQUENCE: 16
gaggcagtcg ctgacacc                                                   18

<210> SEQ ID NO 17
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Acceptor site sequence for exon 18 of SCN5A

<400> SEQUENCE: 17
```

-continued ggggtcttttt cagcaggaat cc                                              22

<210> SEQ ID NO 18
<211> LENGTH: 31
<212> TYPE: DNA
<213> ORGANISM: Homo sapiens
<220> FEATURE:
<221> NAME/KEY: Unsure
<222> LOCATION: (20)..(20)
<223> OTHER INFORMATION: Unsure about the exact nucleotide from
      sequencing data
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: Unsure
<222> LOCATION: (22)..(23)
<223> OTHER INFORMATION: Unsure about the exact nucleotide from
      sequencing data
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: Unsure
<222> LOCATION: (31)..(31)
<223> OTHER INFORMATION: Unsure about the exact nucleotide from
      sequencing data
<220> FEATURE:
<221> NAME/KEY: misc_feature
<222> LOCATION: (31)..(31)
<223> OTHER INFORMATION: n is a, c, g, or t

<400> SEQUENCE: 18
ggagtccagc aagcaggaan annaccatgc n                                     31

<210> SEQ ID NO 19
<211> LENGTH: 45
<212> TYPE: DNA
<213> ORGANISM: Homo sapiens
<220> FEATURE:
<221> NAME/KEY: exon
<222> LOCATION: (1)..(27)
<223> OTHER INFORMATION: Patial sequence of Exon 17 of SCN5A
<220> FEATURE:
<221> NAME/KEY: exon
<222> LOCATION: (28)..(45)
<223> OTHER INFORMATION: Patial sequence of Exon 18 of SCN5A

<400> SEQUENCE: 19 tgg gca cgg agg gag tcc agc aag cag gaa tcc cag cct gtg tcc          45
Trp Ala Arg Arg Glu Ser Ser Lys Gln Glu Ser Gln Pro Val Ser
1               5                   10                  15

<210> SEQ ID NO 20
<211> LENGTH: 48
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Patial sequence of Exon 17 of SCN5A
<220> FEATURE:
<221> NAME/KEY: misc_feature
<222> LOCATION: (27)..(48)
<223> OTHER INFORMATION: Patial sequence of Exon 18 of SCN5A

<400> SEQUENCE: 20
tgggcacgga gggagtccag caagcagcag gaatcccagc ctgtgtcc                   48

<210> SEQ ID NO 21

-continued

```
<211> LENGTH: 57
<212> TYPE: DNA
<213> ORGANISM: Homo sapiens
<220> FEATURE:
<221> NAME/KEY: misc_feature
<222> LOCATION: (1)..(57)
<223> OTHER INFORMATION: Partial genomic DNA sequence of SCN5A

<400> SEQUENCE: 21
gagtccagca agcaggtggg ccctgggtct tttcagcagg aatcccagcc tgtgtcc       57
```